US009422359B2

(12) United States Patent
Kobilka et al.

(10) Patent No.: US 9,422,359 B2
(45) Date of Patent: Aug. 23, 2016

(54) GPCR FUSION PROTEIN CONTAINING AN N-TERMINAL AUTONOMOUSLY FOLDING STABLE DOMAIN, AND CRYSTALS OF THE SAME

(71) Applicant: The Board of Trustees of the Leland Stanford Junior University, Palo Alto, CA (US)

(72) Inventors: Brian K. Kobilka, Palo Alto, CA (US); Yaozhong Zou, Sunnyvale, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/280,384

(22) Filed: May 16, 2014

(65) Prior Publication Data

US 2014/0303345 A1 Oct. 9, 2014

Related U.S. Application Data

(62) Division of application No. 13/420,329, filed on Mar. 14, 2012, now Pat. No. 8,765,414.

(60) Provisional application No. 61/453,020, filed on Mar. 15, 2011, provisional application No. 61/507,425, filed on Jul. 13, 2011.

(51) Int. Cl.
| | |
|---|---|
| *C07K 14/70* | (2006.01) |
| *C07K 14/72* | (2006.01) |
| *C12N 9/24* | (2006.01) |
| *G06F 19/16* | (2011.01) |
| *C07K 14/705* | (2006.01) |
| *C12N 9/36* | (2006.01) |

(52) U.S. Cl.
CPC .......... *C07K 14/705* (2013.01); *C07K 14/70571* (2013.01); *C07K 14/723* (2013.01); *C12N 9/2462* (2013.01); *G06F 19/16* (2013.01); *C07K 2319/00* (2013.01); *C07K 2319/43* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 2003/0198976 A1 | 10/2003 | Feder et al. | |
| 2005/0196851 A1* | 9/2005 | Uckun ............... | C12N 9/1205 435/194 |
| 2006/0188964 A1 | 8/2006 | Mancia et al. | |
| 2007/0031832 A1 | 2/2007 | Watt et al. | |
| 2007/0122881 A1 | 5/2007 | Surber | |
| 2009/0118474 A1 | 5/2009 | Kobilka et al. | |
| 2009/0148510 A1 | 6/2009 | Kobilka et al. | |
| 2011/0031438 A1 | 2/2011 | Stevens et al. | |
| 2011/0130543 A1 | 6/2011 | Stevens et al. | |
| 2012/0219992 A1 | 8/2012 | Kobilka | |

FOREIGN PATENT DOCUMENTS

| | | |
|---|---|---|
| WO | 03/000855 | 1/2003 |
| WO | 2008/068534 | 6/2008 |
| WO | 2009/055509 | 4/2009 |
| WO | 2009/055512 | 4/2009 |

OTHER PUBLICATIONS

Böhm et al., "The computer program LUDI: A new method for the de novo design of enzyme inhibitors", Journal of Computer-Aided Molecular Design, 1992, vol. 6, pp. 61-78.*
Morris et al. "Distributed automated docking of flexible ligands to proteins: Parallel applications of AutoDock 2.4*", J. of Computer-Aided Molecular Design. 1996. vol. 10, pp. 293-304.*
Bell; et al., "Comparison of the Crystal Structure of Bacteriophase T4 Lysozyme at Low, Medium, and High Ionic Strengths", Proteins: Structure, Function, and Genetics (1991), 10:10-21.
Byrne; et al., "Fusion protein approach to improve the crystal quality of cytochrome b03 ubiquinol oxidase from *Esscherichia coli*", Bioenergetics (Aug. 2000), 1459(2-3):449-455.
Chun; et al., "Fusion Partner Toolchest for the Stabilization and Crystallization of G Protein-Coupled Receptors", Structure (Jun. 2012), 20:967-976.
Cheng; et al., "Kinetics and Equilibria of Lysozyme Precipitation and Crystallization in Concentrated Ammonium Sulfate Solutions", Biotechnology and Bioengineering (May 2006), 94(1):177-188.
Cherezov; et al., "High-Resolution Crystal Structure of an Engineered Human beta2-Adrenergic G Protein Coupled Receptor", Science (Nov. 2007), 318(5854):1258-65.
Donahue; et al., "Three-dimensional structure of the platelet integrin recognition segment of the fibrinogen y chain obtained by carrier protein-driven crystallization", PNAS (Dec. 1994), 91:12178-12182.
Engel; et al., "Insertion of carrier proteins into hydrophilic loops of the *Escherichia coli* lactose permease", Biochemica et Biophysica Acta (Aug. 2002), 1564:38-46.
Espitalier; et al., "Mechanism of formation of lysozyme crystals in concentrated ammonium sulfate solution from concentration profiles and equilibria: Influence of the 2nd osmotic virial coefficient", Powder Technology (2009), 190:112-117.
Evrard; et al., "Crystal Structure of the Lysozyme from Bacteriophage Lambda and its Relationship with V and C-type Lysozymes", J. Mol. Biol. (Feb. 1998), 276:151-164.

(Continued)

*Primary Examiner* — Suzanne M Noakes
(74) *Attorney, Agent, or Firm* — James S. Keddie; Bozicevic, Field & Francis LLP

(57) ABSTRACT

Certain embodiments provide a GPCR fusion protein. In particular embodiments, the GPCR fusion protein comprises: a) a G-protein coupled receptor (GPCR); and b) an autonomously folding stable domain, where the autonomously folding stable domain is N-terminal to the GPCR and is heterologous to the GPCR. The GPCR fusion protein is characterized in that is crystallizable under lipidic cubic phase crystallization conditions. In certain embodiments, the GPCR fusion protein may be crystallizable in a complex with a G-protein or in a complex with an antibody that binds to the IC3 loop of the GPCR.

17 Claims, 31 Drawing Sheets

(56) References Cited

OTHER PUBLICATIONS

Forsythe; et al., "Crystallization of chicken egg-white lysozyme from ammonium sulfate", Acta Cryst. (Nov. 1997), D53:795-797.

Geiser; et al., "Bacteriorhodopsin chimeras containing the third cytoplasmic loop of bovine rhodopsin activate transducin for GTP/GDP exchange Protein", Science (Jul. 2006),15:1679-90.

Harada; et al., "Preliminary X-ray Crystallographic Study of Lysozyme Produced by Streptomyces globisporus", J. Mol. Biol. (Jun. 1989), 207:851-852.

Hills; et al., "Subdomain competition, cooperativity and topological frustration in the folding of CheY", J. Mol. Biol. (Oct. 2008), 382(2):485-95.

Hoffman; et al., "A FLAsH-based FRET approach to determine G protein-coupled receptor activation in living cells", Nature Methods (Mar. 2005), 2(3):171-6.

Hunte; et al., "Lipids and membrane protein structures", Current Opinion in Structural Biology (2008), 18:406-411.

Jaakola; et al., "The 2.6 angstrom crystal structure of a human A2A adenosine receptor bound to an antagonist", Science (Nov. 2008), 322:1211-1217.

Kim; et al., Light-driven activation of beta 2-adrenergic receptor signaling by a chimeric rhodopsin containing the beta 2-adrenergic receptor cytoplasmic loops, Biochemistry (Feb. 2005), 44:2284-92.

Kobilka; et al., "Conformational complexity of G-protein-coupled receptors", Trends in Pharmacological Sciences (Aug. 2007),28(8):397-406.

Landau; et al., "Lipidic cubic phases: A novel concept for the crystallization of membrane proteins", PNAS (Dec. 1996), 93:14532-14535.

Lapinsh; et al., "Classification of G-protein coupled receptors by alignment-independent extraction of principal chemical properties of primary amino acid sequences", Protein Science (Apr. 2002), 11:795-805.

Lyne; et al., "Preliminary Crystallographic Examination of a Novel Fungal Lysozyme from Chalaropsis", The Journal of Biological Chemistry (Apr. 1990), 265(12):6928-6930.

Marana; et al., "Crystallization, data collection and phasing of two digestive lysozymes from *Musca domestica*", Acta Cryst. (Aug. 2006), F62:750-752.

Newby; et al., "A general protocol for the crystallization of membrane proteins for X-ray structural investigation", Nature Protocols (2009), 4:619-637.

Petrovskaya; et al., "Expression of G-Protein Coupled Receptors in *Escherichia coli* for Structural Studies", Biochemistry (Mosscow) (Jul. 2010), 75(7):881-891.

Prive, "Fusion Proteins as Tools for Crystallization: the Lactose Permease from *Escherichia coli*", Acta Cryst. (Jul. 1994), D50:375-379.

Prive; et al., "Engineering the Lac Permease for Purification and Crystallization", Journal of Bioenergetics and Biomembranes (Feb. 1996), 28(1):29-34.

Rasmussen; et al., "Crystal structure of the beta2 adrenergic receptor-Gs protein complex", Nature (Jul. 2011), 477 (7366):549-55.

Rasmussen; et al., "Crystal structure of the human beta2 adrenergic G-protein-coupled receptor", Nature (Nov. 2007), 450(7168):383-7.

Remington; et al., "Structure of the Lysozyme from Bacteriophage T4: An Electron Density Map at 2 4 A Resolution", J. Mol. Biol. (Jan. 1978), 118:81-98.

Ries-Kautt; et al., "Crystallization of Previously Desalted Lysozyme in the Presence of Sulfate Ions", Acta Cryst. (Jul. 1994), D50:366-369.

Ries-Kautt; et al., "Relative Effectiveness of Various Ions on the Solubility and Crystal Growth of Lysozyme", The Journal of Biological Chemistry (Jan. 1989), 264(2):745-748.

Rosenbaum; et al., "GPCR Engineering Yields High-Resolution Structural Insights into beta2-Adrenergic Receptor Function", Science (Nov. 2007), 318:(5854):1266-73.

Strynadka; et al., "Lysozyme: A model enzyme in protein crystallography", EXS. (1996), 75:185-222.

Thompson; et al., "Structure of the nociceptin/orphanin FQ receptor in complex with a peptide mimetic", Nature (May 2012), 485:395-401.

Topiol; et al., "X-ray structure breakthroughs in the GPCR transmembrane region", Biochemical Pharmacology (Jul. 2009),78(1):11-20.

Tumova et al., "Insight into the mechanism of dopamine D1-like receptor activation. Evidence for a molecular interplay between the third extracellular loop and the cytoplasmic tail", J. Biol. Chem. (Mar. 2003),278:8146-53.

U.S. Appl. No. 60/999,951, filed Oct. 22, 2007, 79 pgs.
U.S. Appl. No. 61/000,325, filed Oct. 24, 2007, 89 pgs.
U.S. Appl. No. 61/060,107, filed Jun. 9, 2008, 108 pgs.
U.S. Appl. No. 61/194,961, filed Oct. 1, 2008, 173 pgs.

Vilardaga; et al., "Differential Conformational Requirements for Activation of G Proteins and the Regulatory Proteins Arrestin and G Protein-coupled Receptor Kinase in the G Protein-coupled Receptor for Parathyroid Hormone (PTH)/PTH-related Protein", The Journal of Biological Chemistry (Sep. 2001), 276(36):33435-33443.

Vilardaga; et al., "Measurement of the millisecond activation switch of G protein-coupled receptors in living cells", Nature Biotechnology (Jul. 2003), 21(7):807-812.

Wang; et al., "Identification of a domain in the angiotensin II type 1 receptor determining G-q coupling by the use of receptor chimeras", Journal of Biological Chemistry (Jul. 1995), 270(28):16677-16682.

Wess et al., "Identification of a small intracellular region of the muscarinic m3 receptor as a determinant of selective coupling to PI turnover", FEBS Lett. (Nov. 1989), 258:133-6.

Wong et al., "Chimeric muscarinic cholinergic: beta-adrenergic receptors that activate Gs in response to muscarinic agonists", J. Biol. Chem. (Apr. 1990), 265:6219-24.

Yamashita et al., "Distinct roles of the second and third cytoplasmic loops of bovine rhodopsin in G protein activation", J. Biol. Chem. (Nov. 2000), 275:34272-9.

Yao; et al., "Crystallization and Preliminary X-Ray Structure Analysis of Pigeon Egg-White Lysozyme", J. Biochem. (Jan. 1992), 111:1-3.

Yu; et al., "Global chimeric exchanges within the intracellular face of the bradykinin B2 receptor with correspondingangiotensin II type Ia receptor regions: Generation of fully functional hybrids showing characteristic signaling of theATIa receptor", Journal of Cellular Biochemistry (2002),85(4):809-819.

Zhang; et al., "Structure modeling of all identified G protein-coupled receptors in the human genome", PLOS Computational Biology (Mar.-Apr. 2006), 2(2):0088-0099.

\* cited by examiner

Bovine Pancreatic Trypsin Inhibitor (SEQ ID NO:2)
RPDFCLEPPYTGPCKARIIRYFYNAKAGLCQTFVYGGCRAKRNNFKSAEDCMRTCGGA Bovine Calbindin D9K (SEQ ID NO:3)
MKSPEELKGIFEKYAAKEGDPNQLSKEELKLLLQTEFPSLLKGPSTLDELFEELDKNGDGEVSFEEFQV
LVKKISQ Barnase (SEQ ID NO:4)
MAQVINTFDGVADYLQTYHKLPDNYITKSEAQALGWVASKGNLADVAPGKSIGGDIFSNREGKLPGKS
GRTWREADINYTSGFRNSDRILYSSDWLIYKTTDHYQTFTKIR Xylanase II from Trichoderma reesei (SEQ ID NO:5)
ETIQPGTGYNNGYFYSYWNDGHGGVTYTNGPGGQFSVNWSNSGNFVGGKGWQPGTKNKVINFSGS
YNPNGNSYLSVYGWSRNPLIEYYIVENFGTYNPSTGATKLGEVTSDGSVYDIYRTQRVNQPSIIGTATF
YQYWSVRRNHRSSGSVNTANHFNAWAQQGLTLGTMDYQIVAVEGYFSSSGSASITVS Thermostable Glucokinase from Pyrococcus furiosus (SEQ ID NO:6)
MPTWEELYKNAIEKAIKSVPKVKGVLLGYNTNIDAIKYLDSKDLEERIIKAGKEEVIKYSEELPDKINTVSQ
LLGSILWSIRRGKAAELFVESCPVRFYMKRWGWNELRMGGQAGIMANLLGGVYGVPVIVHVPQLSRL
QANLFLDGPIYVPTLENGEVKLIHPKEFSGDEENCIHYIYEFPRGFRVFEFEAPRENRFIGSADDYNTTLF
IREEFRESFSEVIKNVQLAILSGLQALTKENYKEPFEIVKSNLEVLNEREIPVHLEFAFTPDEKVREEILNV
LGMFYSVGLNEVELASIMEILGEKKLAKELLAHDPVDPIAVTEAMLKLAKKTGVKRIHFHTYGYYLALTEY
KGEHVRDALLFAALAAAAKAMKGNITSLEEIREATSVPVNEKATQVEEKLRAEYGIKEGIGEVEGYQIAFI
PTKIVAKPKSTVGIGDTISSSAFIGEFSFTL

FIG. 4

MKTIIALSYIFCLVFADYKDDDDAENLYFQ*GNIFEMLRIDEGLRLKIYKDTEGY
YTIGIGHLLTKSPSLNAAKSELDKAIGRNTNGVITKDEAEKLFNQDVDAAVR
GILRNAKLKPVYDSLDAVRRAALINMVFQMGETGVAGFTNSLRMLQQKR
WDEAAVNLAKSRWYNQTPNRAKRVITTFRTGTWDAYAADEVWVVGMGI
VMSLIVLAIVFGNVLVITAIAKFERLQTVTNYFITSLACADLVMGLAVPFGA
AHILTKTWTFGNFVVCEFWTSIDVLCVTASIETLCVIAVDRYFAITSPFKYQSLL
TKNKARVIILMVWIVSGLTSFLPIQMHWYRATHQEAINCYAEETCCDFFTN
QAYAIASSIVSFYVPLVIMVFVYSRVFQEAKRQLQKIDKSEGRFHVQNLSQVE
QDGRTGHGLRRSSKFCLKEHKALKTLGIIMGTFTLCWLPFFIVNIVHVIQDNL
IRKEVYILLNWIGYVNSGFNPLIYCRSPDFRIAFQELLCLRRSSLKAYGNGYSS
NGNTGEOSG (SEQ ID NO:1)

FIG. 5

Human histamine H2 receptor isoform 1:

*MKTIIALSYIFCLVFA*DYKDDDDA ENLYFQ*G NIFEMLRIDEGLRLKIYKDTEGYYTIGIGHLLTKSPSL
NAAKSELDKAIGRNTNGVITKDEAEKLFNQDVDAAVRGILRNAKLKPVYDSLDAVRRAALINMVF
QMGETGVAGFTNSLRMLQQKRWDEAAVNLAKSRWYNQTPNRAKRVITTFRTGTWDAYAA*TA
CKITITVVLAVLILITVAGNVVVCLAVGLNRRLRNLTNCFIVSLAITDLLGLLVLPFSAIYQLSCKWSF
GKVFCNIYTSLDVMLCTASILNLFMISLDRYCAVMDPLRYPVLVTPVRVAISLVLIWVISITLSFLSIHL
GWNSRNETSKGNHTTSKCKVQVNEVYGLVDGLVTFYLPLLIMCITYYRIFKVARDQAKRINHISSW
KAATIREHKATVTLAAVMGAFIICWFPYFTAFVYRGLRGDDAINEVLEAIVLWLGYANSALNPILY
AALNRDFRTGYQQLFCCRLANRNSHKTSLRSNASQLSRTQSREPRQQEEKPLKLQVWSGTEVTAP
QGATDRPWLCLPECWSVELTHSFIHLFIHSFANIHPIPTTCQEL* (SEQ ID NO: 7)

Human 5-hydroxytryptamine (serotonin) receptor 2A:

*MKTIIALSYIFCLVFA*DYKDDDDA ENLYFQ*G NIFEMLRIDEGLRLKIYKDTEGYYTIGIGHLLTKSPSL
NAAKSELDKAIGRNTNGVITKDEAEKLFNQDVDAAVRGILRNAKLKPVYDSLDAVRRAALINMVF
QMGETGVAGFTNSLRMLQQKRWDEAAVNLAKSRWYNQTPNRAKRVITTFRTGTWDAYAA*LQ
EKNWSALLTAVVIILTIAGNILVIMAVSLEKKLQNATNYFLMSLAIADMLLGFLVMPVSMLTILYGY
RWPLPSKLCAVWIYLDVLFSTASIMHLCAISLDRYVAIQNPIHHSRFNSRTKAFLKIIAVWTISVGIS
MPIPVFGLQDDSKVFKEGSCLLADDNFVLIGSFVSFFIPLTIMVITYFLTIKSLQKEATLCVSDLGTRA
KLASFSFLPQSSLSSEKLFQRSIHREPGSYTGRRTMQSISNEQKACKVLGIVFFLFVVMWCPFFITNI
MAVICKESCNEDVIGALLNVFVWIGYLSSAVNPLVYTLFNKTYRSAFSRYIQCQYKENKKPLQLILV
NTIPALAYKSSQLQMGQKKNSKQDAKTTDNDCSMVALGKQHSEEASKDNSDGVNEKVSCV*
(SEQ ID NO: 8)

Human angiotensin II type-1 receptor:

*MKTIIALSYIFCLVFA*DYKDDDDA ENLYFQ*G NIFEMLRIDEGLRLKIYKDTEGYYTIGIGHLLTKSPSL
NAAKSELDKAIGRNTNGVITKDEAEKLFNQDVDAAVRGILRNAKLKPVYDSLDAVRRAALINMVF
QMGETGVAGFTNSLRMLQQKRWDEAAVNLAKSRWYNQTPNRAKRVITTFRTGTWDAYAA*RH
NYIFVMIPTLYSIIFVVGIFGNSLVVIVIYFYMKLKTVASVFLLNLALADLCFLLTLPLWAVYTAMEYR
WPFGNYLCKIASASVSFNLYASVFLLTCLSIDRYLAIVHPMKSRLRRTMLVAKVTCIIWLLAGLASL
PAIIHRNVFFIENTNITVCAFHYESQNSTLPIGLGLTKNILGFLFPFLIILTSYTLIWKALKKAYEIQKNK
PRNDDIFKIIMAIVLFFFFSWIPHQIFTFLDVLIQLGIIRDCRIADIVDTAMPITICIAYFNNCLNPLFYG
FLGKKFKRYFLQLLKYIPPKAKSHSNLSTKMSTLSYRPSDNVSSSTKKPAPCFEVE* (SEQ ID NO: 9)

Human opioid receptor:

*MKTIIALSYIFCLVFA*DYKDDDDA ENLYFQ*G NIFEMLRIDEGLRLKIYKDTEGYYTIGIGHLLTKSPSL
NAAKSELDKAIGRNTNGVITKDEAEKLFNQDVDAAVRGILRNAKLKPVYDSLDAVRRAALINMVF
QMGETGVAGFTNSLRMLQQKRWDEAAVNLAKSRWYNQTPNRAKRVITTFRTGTWDAYAA*S
MITATTIMALYSIVCVVGLFGNFLVMYVIVRYTKMKTATNIYIFNLALADALATSTLPFQSVNYLM
GTWPFGTILCKIVISIDYYNMFTSIFTLCTMSVDRYIAVCHPVKALDFRTPRNAKIINVCNWILSSAI*

FIG. 6

GLPVMFMATTKYRQGSIDCTLTFSHPTWYWENLLKICVFIFAFIMPVLIITVCYGLMILRLKSVRML
SGSKEKDRNLRRITRMVLVVVAVFIVCWTPIHIYVIIKALVTIPETTFQTVSWHFCIALGYTNSCLNP
VLYAFLDENFKRCFREFCIPTSSNIEQQNSTRIRQNTRDHPSTANTVDRTNHQLENLEAETAPLP
(SEQ ID NO: 10)

Human neuropeptide Y receptor:

MKTIIALSYIFCLVFADYKDDDDA|ENLYFQ*G|NIFEMLRIDEGLRLKIYKDTEGYYTIGIGHLLTKSPSL
NAAKSELDKAIGRNTNGVITKDEAEKLFNQDVDAAVRGILRNAKLKPVYDSLDAVRRAALINMVF
QMGETGVAGFTNSLRMLQQKRWDEAAVNLAKSRWYNQTPNRAKRVITTFRTGTWDAYAA*LP*
*LAMIFTLALAYGAVIILGVSGNLALIIIILKQKEMRNVTNILIVNLSFSDLLVAIMCLPLTFVYTLMDH
WVFGEAMCKLNPFVQCVSITVSIFSLVLIAVERHQLIINPRGWRPNNRHAYVGIAVIWVLAVASSL
PFLIYQVMTDEPFQNVTLDAYKDKYVCFDQFPSDSHRLSYTTLLLVLQYFGPLCFIFICYFKIYIRLKR
RNNMMDKMRDNKYRSSETKRINIMLLSIVVAFAVCWLPLTIFNTVFDWNHQIIATCNHNLLFLLC
HLTAMISTCVNPIFYGFLNKNFQRDLQFFFNFCDFRSRDDDYETIAMSTMHTDVSKTSLKQASPV
AFKKINNNDDNEKI* (SEQ ID NO: 11)

Human Olfactory receptor:

MKTIIALSYIFCLVFADYKDDDDA|ENLYFQ*G|NIFEMLRIDEGLRLKIYKDTEGYYTIGIGHLLTKSPSL
NAAKSELDKAIGRNTNGVITKDEAEKLFNQDVDAAVRGILRNAKLKPVYDSLDAVRRAALINMVF
QMGETGVAGFTNSLRMLQQKRWDEAAVNLAKSRWYNQTPNRAKRVITTFRTGTWDAYAA*W*
*PHLEVVIFVVVLIFYLMTLIGNLFIIILSYLDSHLHTPMYFFLSNLSFLDLCYTTSSIPQLLVNLWGPEKT
ISYAGCMIQLYFVLALGTAECVLLVVMSYDRYAAVCRPLHYTVLMHPRFCHLLAVASWVSGFTNS
ALHSSFTFWVPLCGHRQVDHFFCEVPALLRLSCVDTHVNELTLMITSSIFVLIPLILILTSYGAIVQAV
LRMQSTTGLQKVFGTCGAHLMAVSLFFIPAMCIYLQPPSGNSQDQGKFIALFYTVVTPSLNPLIYTL
RNKVVRGAVKRLMGWE* (SEQ ID NO: 12)

Human thyrotropin-releasing hormone receptor:

MKTIIALSYIFCLVFADYKDDDDA|ENLYFQ*G|NIFEMLRIDEGLRLKIYKDTEGYYTIGIGHLLTKSPSL
NAAKSELDKAIGRNTNGVITKDEAEKLFNQDVDAAVRGILRNAKLKPVYDSLDAVRRAALINMVF
QMGETGVAGFTNSLRMLQQKRWDEAAVNLAKSRWYNQTPNRAKRVITTFRTGTWDAYAA*LE*
*YQVVTILLVLIICGLGIVGNIMVVLVVMRTKHMRTPTNCYLVSLAVADLMVLVAAGLPNITDSIYG
SWVYGYVGCLCITYLQYLGINASSCSITAFTIERYIAICHPIKAQFLCTFSRAKKIIIFVWAFTSLYCML
WFFLLDLNISTYKDAIVISCGYKISRNYYSPIYLMDFGVFYVVPMILATVLYGFIARILFLNPIPSDPKE
NSKTWKNDSTHQNTNLNVNTSNRCFNSTVSSRKQVTKMLAVVVILFALLWMPYRTLVVVNSFLS
SPFQENWFLLFCRICIYLNSAINPVIYNLMSQKFRAAFRKLCNCKQKPTEKPANYSVALNYSVIKES
DHFSTELDDITVTDTYLSATKVSFDDTCLASEVSFSQS* (SEQ ID NO: 13)

FIG. 6 (Cont.)

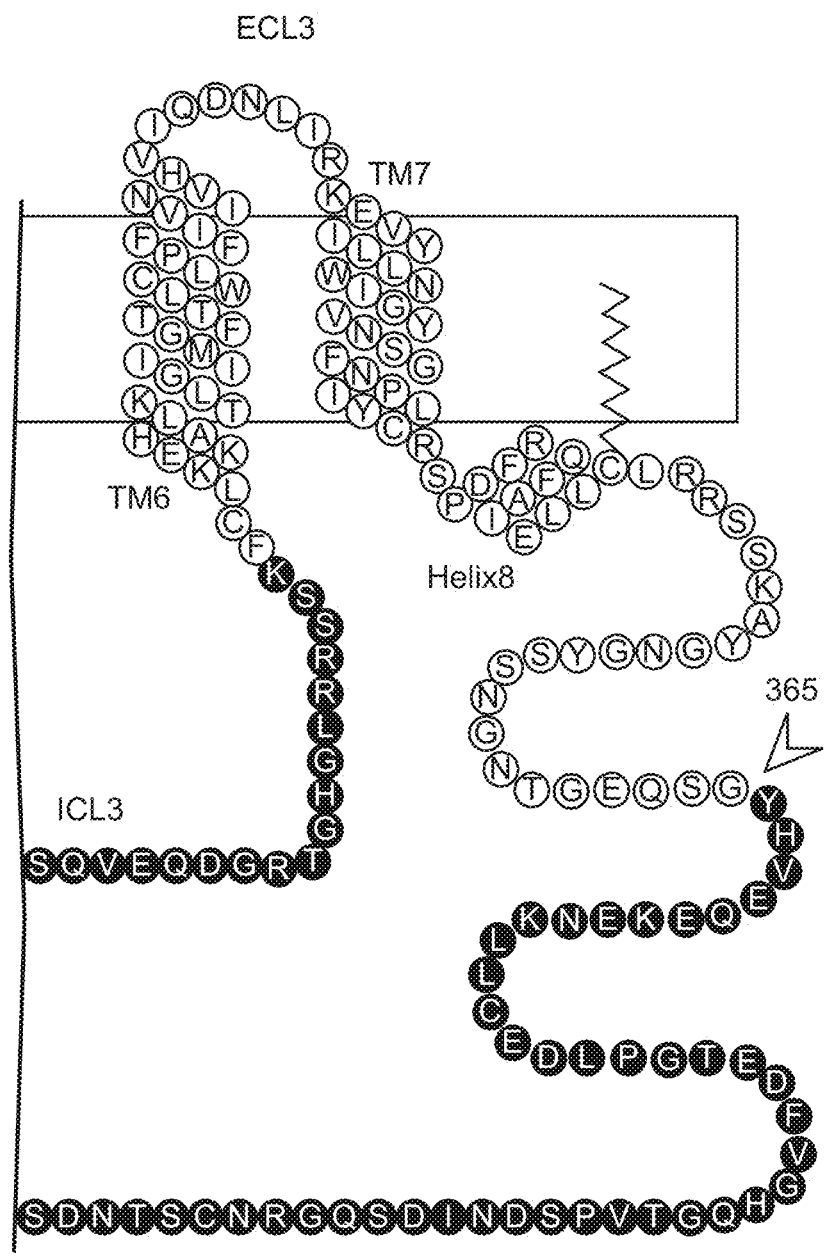
FIG. 22 (Cont. 1)

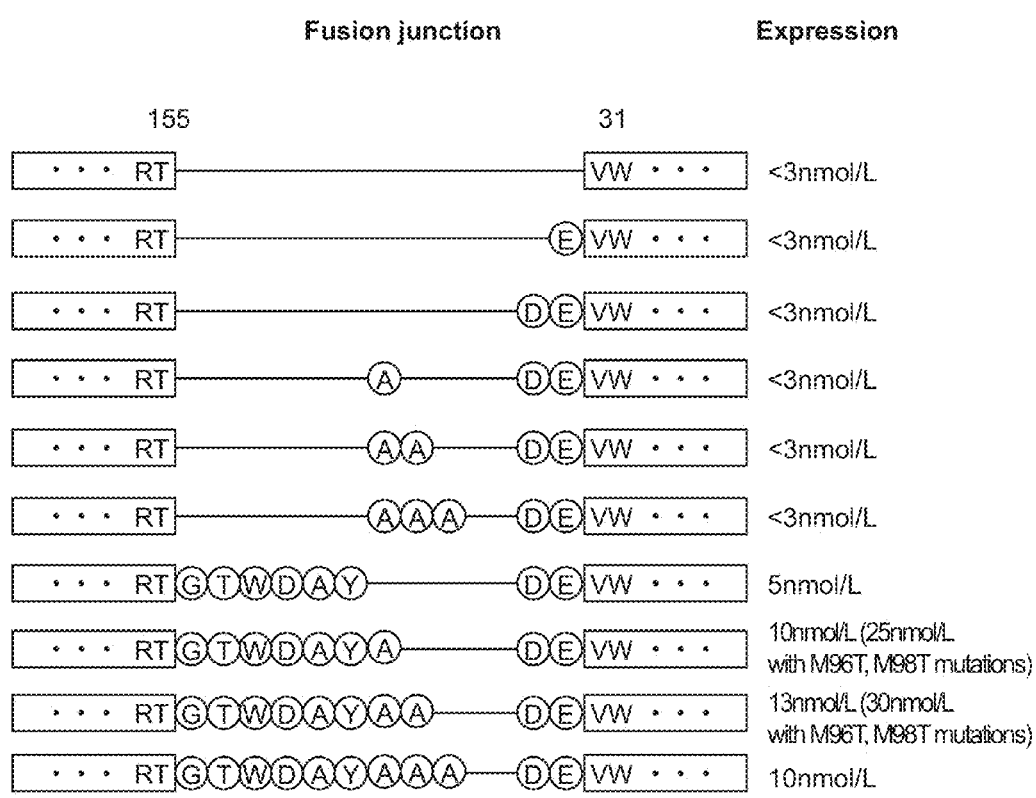
FIG. 22 (Cont. 2)

SEQUENCE LISTING

<160> NUMBER OF SEQ ID NOS: 29

<210> SEQ ID NO 1
<211> LENGTH: 530
<212> TYPE: PRT
<213> ORGANISM: Artificial Sequence
<220> FEATURE:
<223> OTHER INFORMATION: synthetic fusion protein

<400> SEQUENCE: 1

```
Met Lys Thr Ile Ile Ala Leu Ser Tyr Ile Phe Cys Leu Val Phe Ala
1               5                   10                  15

Asp Tyr Lys Asp Asp Asp Asp Ala Glu Asn Leu Tyr Phe Gln Gly Asn
            20                  25                  30

Ile Phe Glu Met Leu Arg Ile Asp Glu Gly Leu Arg Leu Lys Ile Tyr
        35                  40                  45

Lys Asp Thr Glu Gly Tyr Tyr Thr Ile Gly Ile Gly His Leu Leu Thr
    50                  55                  60

Lys Ser Pro Ser Leu Asn Ala Ala Lys Ser Glu Leu Asp Lys Ala Ile
65                  70                  75                  80

Gly Arg Asn Thr Asn Gly Val Ile Thr Lys Asp Glu Ala Glu Lys Leu
                85                  90                  95

Phe Asn Gln Asp Val Asp Ala Ala Val Arg Gly Ile Leu Arg Asn Ala
            100                 105                 110

Lys Leu Lys Pro Val Tyr Asp Ser Leu Asp Ala Val Arg Arg Ala Ala
        115                 120                 125

Leu Ile Asn Met Val Phe Gln Met Gly Glu Thr Gly Val Ala Gly Phe
    130                 135                 140

Thr Asn Ser Leu Arg Met Leu Gln Gln Lys Arg Trp Asp Glu Ala Ala
145                 150                 155                 160

Val Asn Leu Ala Lys Ser Arg Trp Tyr Asn Gln Thr Pro Asn Arg Ala
                165                 170                 175

Lys Arg Val Ile Thr Thr Phe Arg Thr Gly Thr Trp Asp Ala Tyr Ala
            180                 185                 190

Ala Asp Glu Val Trp Val Val Gly Met Gly Ile Val Met Ser Leu Ile
        195                 200                 205

Val Leu Ala Ile Val Phe Gly Asn Val Leu Val Ile Thr Ala Ile Ala
    210                 215                 220

Lys Phe Glu Arg Leu Gln Thr Val Thr Asn Tyr Phe Ile Thr Ser Leu
225                 230                 235                 240

Ala Cys Ala Asp Leu Val Met Gly Leu Ala Val Val Pro Phe Gly Ala
                245                 250                 255
```

```
Ala His Ile Leu Thr Lys Thr Trp Thr Phe Gly Asn Phe Trp Cys Glu
            260                 265                 270

Phe Trp Thr Ser Ile Asp Val Leu Cys Val Thr Ala Ser Ile Glu Thr
            275                 280                 285

Leu Cys Val Ile Ala Val Asp Arg Tyr Phe Ala Ile Thr Ser Pro Phe
            290                 295                 300

Lys Tyr Gln Ser Leu Leu Thr Lys Asn Lys Ala Arg Val Ile Ile Leu
305                 310                 315                 320

Met Val Trp Ile Val Ser Gly Leu Thr Ser Phe Leu Pro Ile Gln Met
                    325                 330                 335

His Trp Tyr Arg Ala Thr His Gln Glu Ala Ile Asn Cys Tyr Ala Glu
            340                 345                 350

Glu Thr Cys Cys Asp Phe Phe Thr Asn Gln Ala Tyr Ala Ile Ala Ser
            355                 360                 365

Ser Ile Val Ser Phe Tyr Val Pro Leu Val Ile Met Val Phe Val Tyr
            370                 375                 380

Ser Arg Val Phe Gln Glu Ala Lys Arg Gln Leu Gln Lys Ile Asp Lys
385                 390                 395                 400

Ser Glu Gly Arg Phe His Val Gln Asn Leu Ser Gln Val Glu Gln Asp
            405                 410                 415

Gly Arg Thr Gly His Gly Leu Arg Arg Ser Ser Lys Phe Cys Leu Lys
            420                 425                 430

Glu His Lys Ala Leu Lys Thr Leu Gly Ile Ile Met Gly Thr Phe Thr
            435                 440                 445

Leu Cys Trp Leu Pro Phe Phe Ile Val Asn Ile Val His Val Ile Gln
450                 455                 460

Asp Asn Leu Ile Arg Lys Glu Val Tyr Ile Leu Leu Asn Trp Ile Gly
465                 470                 475                 480

Tyr Val Asn Ser Gly Phe Asn Pro Leu Ile Tyr Cys Arg Ser Pro Asp
                    485                 490                 495

Phe Arg Ile Ala Phe Gln Glu Leu Leu Cys Leu Arg Arg Ser Ser Leu
            500                 505                 510

Lys Ala Tyr Gly Asn Gly Tyr Ser Ser Asn Gly Asn Thr Gly Glu Gln
            515                 520                 525

Ser Gly
    530

<210> SEQ ID NO 2
<211> LENGTH: 58
<212> TYPE: PRT
<213> ORGANISM: Bos taurus

<400> SEQUENCE: 2

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
            35                  40                  45

Glu Asp Cys Met Arg Thr Cys Gly Gly Ala
50                  55

<210> SEQ ID NO 3
<211> LENGTH: 76
<212> TYPE: PRT
<213> ORGANISM: Bos taurus
```

<400> SEQUENCE: 3

Met Lys Ser Pro Glu Glu Leu Lys Gly Ile Phe Glu Lys Tyr Ala Ala
1               5                   10                  15

Lys Glu Gly Asp Pro Asn Gln Leu Ser Lys Glu Glu Leu Lys Leu Leu
            20                  25                  30

Leu Gln Thr Glu Phe Pro Ser Leu Leu Lys Gly Pro Ser Thr Leu Asp
        35                  40                  45

Glu Leu Phe Glu Glu Leu Asp Lys Asn Gly Asp Gly Glu Val Ser Phe
    50                  55                  60

Glu Glu Phe Gln Val Leu Val Lys Lys Ile Ser Gln
65                  70                  75

<210> SEQ ID NO 4
<211> LENGTH: 111
<212> TYPE: PRT
<213> ORGANISM: Bacillus amyloliquefaciens

<400> SEQUENCE: 4

Met Ala Gln Val Ile Asn Thr Phe Asp Gly Val Ala Asp Tyr Leu Gln
1               5                   10                  15

Thr Tyr His Lys Leu Pro Asp Asn Tyr Ile Thr Lys Ser Glu Ala Gln
            20                  25                  30

Ala Leu Gly Trp Val Ala Ser Lys Gly Asn Leu Ala Asp Val Ala Pro
        35                  40                  45

Gly Lys Ser Ile Gly Gly Asp Ile Phe Ser Asn Arg Glu Gly Lys Leu
    50                  55                  60

Pro Gly Lys Ser Gly Arg Thr Trp Arg Glu Ala Asp Ile Asn Tyr Thr
65                  70                  75                  80

Ser Gly Phe Arg Asn Ser Asp Arg Ile Leu Tyr Ser Ser Asp Trp Leu
                85                  90                  95

Ile Tyr Lys Thr Thr Asp His Tyr Gln Thr Phe Thr Lys Ile Arg
            100                 105                 110

<210> SEQ ID NO 5
<211> LENGTH: 190
<212> TYPE: PRT
<213> ORGANISM: Trichoderma reesei

<400> SEQUENCE: 5

Glu Thr Ile Gln Pro Gly Thr Gly Tyr Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
            115                 120                 125

```
Ile Gly Thr Ala Thr Phe Tyr Gln Tyr Trp Ser Val Arg Arg Asn His
        130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 6
<211> LENGTH: 455
<212> TYPE: PRT
<213> ORGANISM: Pyrococcus furiosus

<400> SEQUENCE: 6

Met Pro Thr Trp Glu Glu Leu Tyr Lys Asn Ala Ile Glu Lys Ala Ile
1               5                   10                  15

Lys Ser Val Pro Lys Val Lys Gly Val Leu Leu Gly Tyr Asn Thr Asn
            20                  25                  30

Ile Asp Ala Ile Lys Tyr Leu Asp Ser Lys Asp Leu Glu Glu Arg Ile
        35                  40                  45

Ile Lys Ala Gly Lys Glu Glu Val Ile Lys Tyr Ser Glu Glu Leu Pro
50                  55                  60

Asp Lys Ile Asn Thr Val Ser Gln Leu Leu Gly Ser Ile Leu Trp Ser
65                  70                  75                  80

Ile Arg Arg Gly Lys Ala Ala Glu Leu Phe Val Glu Ser Cys Pro Val
                85                  90                  95

Arg Phe Tyr Met Lys Arg Trp Gly Trp Asn Glu Leu Arg Met Gly Gly
            100                 105                 110

Gln Ala Gly Ile Met Ala Asn Leu Leu Gly Gly Val Tyr Gly Val Pro
        115                 120                 125

Val Ile Val His Val Pro Gln Leu Ser Arg Leu Gln Ala Asn Leu Phe
130                 135                 140

Leu Asp Gly Pro Ile Tyr Val Pro Thr Leu Glu Asn Gly Glu Val Lys
145                 150                 155                 160

Leu Ile His Pro Lys Glu Phe Ser Gly Asp Glu Asn Cys Ile His
                165                 170                 175

Tyr Ile Tyr Glu Phe Pro Arg Gly Phe Arg Val Phe Glu Phe Glu Ala
            180                 185                 190

Pro Arg Glu Asn Arg Phe Ile Gly Ser Ala Asp Asp Tyr Asn Thr Thr
        195                 200                 205

Leu Phe Ile Arg Glu Glu Phe Arg Glu Ser Phe Ser Glu Val Ile Lys
210                 215                 220

Asn Val Gln Leu Ala Ile Leu Ser Gly Leu Gln Ala Leu Thr Lys Glu
225                 230                 235                 240

Asn Tyr Lys Glu Pro Phe Glu Ile Val Lys Ser Asn Leu Glu Val Leu
                245                 250                 255

Asn Glu Arg Glu Ile Pro Val His Leu Glu Phe Ala Phe Thr Pro Asp
            260                 265                 270

Glu Lys Val Arg Glu Glu Ile Leu Asn Val Leu Gly Met Phe Tyr Ser
        275                 280                 285

Val Gly Leu Asn Glu Val Glu Leu Ala Ser Ile Met Glu Ile Leu Gly
290                 295                 300

Glu Lys Lys Leu Ala Lys Glu Leu Leu Ala His Asp Pro Val Asp Pro
305                 310                 315                 320
```

```
Ile Ala Val Thr Glu Ala Met Leu Lys Leu Ala Lys Lys Thr Gly Val
                325                 330                 335

Lys Arg Ile His Phe His Thr Tyr Gly Tyr Tyr Leu Ala Leu Thr Glu
            340                 345                 350

Tyr Lys Gly Glu His Val Arg Asp Ala Leu Leu Phe Ala Ala Leu Ala
        355                 360                 365

Ala Ala Ala Lys Ala Met Lys Gly Asn Ile Thr Ser Leu Glu Glu Ile
    370                 375                 380

Arg Glu Ala Thr Ser Val Pro Val Asn Glu Lys Ala Thr Gln Val Glu
385                 390                 395                 400

Glu Lys Leu Arg Ala Glu Tyr Gly Ile Lys Glu Gly Ile Gly Glu Val
                405                 410                 415

Glu Gly Tyr Gln Ile Ala Phe Ile Pro Thr Lys Ile Val Ala Lys Pro
            420                 425                 430

Lys Ser Thr Val Gly Ile Gly Asp Thr Ile Ser Ser Ser Ala Phe Ile
        435                 440                 445

Gly Glu Phe Ser Phe Thr Leu
    450                 455

<210> SEQ ID NO 7
<211> LENGTH: 576
<212> TYPE: PRT
<213> ORGANISM: Artificial Sequence
<220> FEATURE:
<223> OTHER INFORMATION: synthetic fusion protein

<400> SEQUENCE: 7

Met Lys Thr Ile Ile Ala Leu Ser Tyr Ile Phe Cys Leu Val Phe Ala
1               5                   10                  15

Asp Tyr Lys Asp Asp Asp Asp Ala Glu Asn Leu Tyr Phe Gln Gly Asn
                20                  25                  30

Ile Phe Glu Met Leu Arg Ile Asp Glu Gly Leu Arg Leu Lys Ile Tyr
            35                  40                  45

Lys Asp Thr Glu Gly Tyr Tyr Thr Ile Gly Ile Gly His Leu Leu Thr
50                  55                  60

Lys Ser Pro Ser Leu Asn Ala Ala Lys Ser Glu Leu Asp Lys Ala Ile
65                  70                  75                  80

Gly Arg Asn Thr Asn Gly Val Ile Thr Lys Asp Glu Ala Glu Lys Leu
                85                  90                  95

Phe Asn Gln Asp Val Asp Ala Ala Val Arg Gly Ile Leu Arg Asn Ala
            100                 105                 110

Lys Leu Lys Pro Val Tyr Asp Ser Leu Asp Ala Val Arg Arg Ala Ala
        115                 120                 125

Leu Ile Asn Met Val Phe Gln Met Gly Glu Thr Gly Val Ala Gly Phe
    130                 135                 140

Thr Asn Ser Leu Arg Met Leu Gln Gln Lys Arg Trp Asp Glu Ala Ala
145                 150                 155                 160

Val Asn Leu Ala Lys Ser Arg Trp Tyr Asn Gln Thr Pro Asn Arg Ala
                165                 170                 175

Lys Arg Val Ile Thr Thr Phe Arg Thr Gly Thr Trp Asp Ala Tyr Ala
            180                 185                 190

Ala Thr Ala Cys Lys Ile Thr Ile Thr Val Val Leu Ala Val Leu Ile
        195                 200                 205

Leu Ile Thr Val Ala Gly Asn Val Val Val Cys Leu Ala Val Gly Leu
    210                 215                 220
```

```
Asn Arg Arg Leu Arg Asn Leu Thr Asn Cys Phe Ile Val Ser Leu Ala
225                 230                 235                 240

Ile Thr Asp Leu Leu Leu Gly Leu Leu Val Leu Pro Phe Ser Ala Ile
            245                 250                 255

Tyr Gln Leu Ser Cys Lys Trp Ser Phe Gly Lys Val Phe Cys Asn Ile
        260                 265                 270

Tyr Thr Ser Leu Asp Val Met Leu Cys Thr Ala Ser Ile Leu Asn Leu
    275                 280                 285

Phe Met Ile Ser Leu Asp Arg Tyr Cys Ala Val Met Asp Pro Leu Arg
290                 295                 300

Tyr Pro Val Leu Val Thr Pro Val Arg Val Ala Ile Ser Leu Val Leu
305                 310                 315                 320

Ile Trp Val Ile Ser Ile Thr Leu Ser Phe Leu Ser Ile His Leu Gly
                325                 330                 335

Trp Asn Ser Arg Asn Glu Thr Ser Lys Gly Asn His Thr Thr Ser Lys
                340                 345                 350

Cys Lys Val Gln Val Asn Glu Val Tyr Gly Leu Val Asp Gly Leu Val
                355                 360                 365

Thr Phe Tyr Leu Pro Leu Leu Ile Met Cys Ile Thr Tyr Tyr Arg Ile
370                 375                 380

Phe Lys Val Ala Arg Asp Gln Ala Lys Arg Ile Asn His Ile Ser Ser
385                 390                 395                 400

Trp Lys Ala Ala Thr Ile Arg Glu His Lys Ala Thr Val Thr Leu Ala
                405                 410                 415

Ala Val Met Gly Ala Phe Ile Ile Cys Trp Phe Pro Tyr Phe Thr Ala
                420                 425                 430

Phe Val Tyr Arg Gly Leu Arg Gly Asp Asp Ala Ile Asn Glu Val Leu
                435                 440                 445

Glu Ala Ile Val Leu Trp Leu Gly Tyr Ala Asn Ser Ala Leu Asn Pro
450                 455                 460

Ile Leu Tyr Ala Ala Leu Asn Arg Asp Phe Arg Thr Gly Tyr Gln Gln
465                 470                 475                 480

Leu Phe Cys Cys Arg Leu Ala Asn Arg Asn Ser His Lys Thr Ser Leu
                485                 490                 495

Arg Ser Asn Ala Ser Gln Leu Ser Arg Thr Gln Ser Arg Glu Pro Arg
                500                 505                 510

Gln Gln Glu Glu Lys Pro Leu Lys Leu Gln Val Trp Ser Gly Thr Glu
                515                 520                 525

Val Thr Ala Pro Gln Gly Ala Thr Asp Arg Pro Trp Leu Cys Leu Pro
                530                 535                 540

Glu Cys Trp Ser Val Glu Leu Thr His Ser Phe Ile His Leu Phe Ile
545                 550                 555                 560

His Ser Phe Ala Asn Ile His Pro Ile Pro Thr Thr Cys Gln Glu Leu
                565                 570                 575
```

<210> SEQ ID NO 8
<211> LENGTH: 594
<212> TYPE: PRT
<213> ORGANISM: Artificial Sequence
<220> FEATURE:
<223> OTHER INFORMATION: synthetic fusion protein

<400> SEQUENCE: 8

```
Met Lys Thr Ile Ile Ala Leu Ser Tyr Ile Phe Cys Leu Val Phe Ala
1               5                   10                  15
```

```
Asp Tyr Lys Asp Asp Asp Ala Glu Asn Leu Tyr Phe Gln Gly Asn
            20                  25                  30

Ile Phe Glu Met Leu Arg Ile Asp Glu Gly Leu Arg Leu Lys Ile Tyr
        35                  40                  45

Lys Asp Thr Glu Gly Tyr Tyr Thr Ile Gly Ile Gly His Leu Leu Thr
 50                      55                  60

Lys Ser Pro Ser Leu Asn Ala Ala Lys Ser Glu Leu Asp Lys Ala Ile
 65                  70                  75                  80

Gly Arg Asn Thr Asn Gly Val Ile Thr Lys Asp Glu Ala Glu Lys Leu
                 85                  90                  95

Phe Asn Gln Asp Val Asp Ala Ala Val Arg Gly Ile Leu Arg Asn Ala
            100                 105                 110

Lys Leu Lys Pro Val Tyr Asp Ser Leu Asp Ala Val Arg Arg Ala Ala
        115                 120                 125

Leu Ile Asn Met Val Phe Gln Met Gly Glu Thr Gly Val Ala Gly Phe
130                 135                 140

Thr Asn Ser Leu Arg Met Leu Gln Gln Lys Arg Trp Asp Glu Ala Ala
145                 150                 155                 160

Val Asn Leu Ala Lys Ser Arg Trp Tyr Asn Gln Thr Pro Asn Arg Ala
                165                 170                 175

Lys Arg Val Ile Thr Thr Phe Arg Thr Gly Thr Trp Asp Ala Tyr Ala
            180                 185                 190

Ala Leu Gln Glu Lys Asn Trp Ser Ala Leu Leu Thr Ala Val Val Ile
        195                 200                 205

Ile Leu Thr Ile Ala Gly Asn Ile Leu Val Ile Met Ala Val Ser Leu
    210                 215                 220

Glu Lys Lys Leu Gln Asn Ala Thr Asn Tyr Phe Leu Met Ser Leu Ala
225                 230                 235                 240

Ile Ala Asp Met Leu Leu Gly Phe Leu Val Met Pro Val Ser Met Leu
                245                 250                 255

Thr Ile Leu Tyr Gly Tyr Arg Trp Pro Leu Pro Ser Lys Leu Cys Ala
            260                 265                 270

Val Trp Ile Tyr Leu Asp Val Leu Phe Ser Thr Ala Ser Ile Met His
        275                 280                 285

Leu Cys Ala Ile Ser Leu Asp Arg Tyr Val Ala Ile Gln Asn Pro Ile
    290                 295                 300

His His Ser Arg Phe Asn Ser Arg Thr Lys Ala Phe Leu Lys Ile Ile
305                 310                 315                 320

Ala Val Trp Thr Ile Ser Val Gly Ile Ser Met Pro Ile Pro Val Phe
                325                 330                 335

Gly Leu Gln Asp Asp Ser Lys Val Phe Lys Glu Gly Ser Cys Leu Leu
            340                 345                 350

Ala Asp Asp Asn Phe Val Leu Ile Gly Ser Phe Val Ser Phe Phe Ile
        355                 360                 365

Pro Leu Thr Ile Met Val Ile Thr Tyr Phe Leu Thr Ile Lys Ser Leu
    370                 375                 380

Gln Lys Glu Ala Thr Leu Cys Val Ser Asp Leu Gly Thr Arg Ala Lys
385                 390                 395                 400

Leu Ala Ser Phe Ser Phe Leu Pro Gln Ser Ser Leu Ser Ser Glu Lys
                405                 410                 415

Leu Phe Gln Arg Ser Ile His Arg Glu Pro Gly Ser Tyr Thr Gly Arg
            420                 425                 430
```

```
Arg Thr Met Gln Ser Ile Ser Asn Glu Gln Lys Ala Cys Lys Val Leu
            435                 440                 445

Gly Ile Val Phe Phe Leu Phe Val Val Met Trp Cys Pro Phe Phe Ile
        450                 455                 460

Thr Asn Ile Met Ala Val Ile Cys Lys Glu Ser Cys Asn Glu Asp Val
465                 470                 475                 480

Ile Gly Ala Leu Leu Asn Val Phe Val Trp Ile Gly Tyr Leu Ser Ser
                485                 490                 495

Ala Val Asn Pro Leu Val Tyr Thr Leu Phe Asn Lys Thr Tyr Arg Ser
            500                 505                 510

Ala Phe Ser Arg Tyr Ile Gln Cys Gln Tyr Lys Glu Asn Lys Lys Pro
        515                 520                 525

Leu Gln Leu Ile Leu Val Asn Thr Ile Pro Ala Leu Ala Tyr Lys Ser
    530                 535                 540

Ser Gln Leu Gln Met Gly Gln Lys Asn Ser Lys Gln Asp Ala Lys
545                 550                 555                 560

Thr Thr Asp Asn Asp Cys Ser Met Val Ala Leu Gly Lys Gln His Ser
                565                 570                 575

Glu Glu Ala Ser Lys Asp Asn Ser Asp Gly Val Asn Glu Lys Val Ser
            580                 585                 590

Cys Val

<210> SEQ ID NO 9
<211> LENGTH: 530
<212> TYPE: PRT
<213> ORGANISM: Artificial Sequence
<220> FEATURE:
<223> OTHER INFORMATION: synthetic fusion protein

<400> SEQUENCE: 9

Met Lys Thr Ile Ile Ala Leu Ser Tyr Ile Phe Cys Leu Val Phe Ala
1               5                   10                  15

Asp Tyr Lys Asp Asp Asp Ala Glu Asn Leu Tyr Phe Gln Gly Asn
            20                  25                  30

Ile Phe Glu Met Leu Arg Ile Asp Glu Gly Leu Arg Leu Lys Ile Tyr
        35                  40                  45

Lys Asp Thr Glu Gly Tyr Tyr Thr Ile Gly Ile Gly His Leu Leu Thr
    50                  55                  60

Lys Ser Pro Ser Leu Asn Ala Ala Lys Ser Glu Leu Asp Lys Ala Ile
65                  70                  75                  80

Gly Arg Asn Thr Asn Gly Val Ile Thr Lys Asp Glu Ala Glu Lys Leu
                85                  90                  95

Phe Asn Gln Asp Val Asp Ala Ala Val Arg Gly Ile Leu Arg Asn Ala
            100                 105                 110

Lys Leu Lys Pro Val Tyr Asp Ser Leu Asp Ala Val Arg Arg Ala Ala
        115                 120                 125

Leu Ile Asn Met Val Phe Gln Met Gly Glu Thr Gly Val Ala Gly Phe
    130                 135                 140

Thr Asn Ser Leu Arg Met Leu Gln Gln Lys Arg Trp Asp Glu Ala Ala
145                 150                 155                 160

Val Asn Leu Ala Lys Ser Arg Trp Tyr Asn Gln Thr Pro Asn Arg Ala
                165                 170                 175

Lys Arg Val Ile Thr Thr Phe Arg Thr Gly Thr Trp Asp Ala Tyr Ala
            180                 185                 190
```

Ala Arg His Asn Tyr Ile Phe Val Met Ile Pro Thr Leu Tyr Ser Ile
        195                 200                 205

Ile Phe Val Val Gly Ile Phe Gly Asn Ser Leu Val Val Ile Val Ile
210                 215                 220

Tyr Phe Tyr Met Lys Leu Lys Thr Val Ala Ser Val Phe Leu Leu Asn
225                 230                 235                 240

Leu Ala Leu Ala Asp Leu Cys Phe Leu Leu Thr Leu Pro Leu Trp Ala
                245                 250                 255

Val Tyr Thr Ala Met Glu Tyr Arg Trp Pro Phe Gly Asn Tyr Leu Cys
            260                 265                 270

Lys Ile Ala Ser Ala Ser Val Ser Phe Asn Leu Tyr Ala Ser Val Phe
        275                 280                 285

Leu Leu Thr Cys Leu Ser Ile Asp Arg Tyr Leu Ala Ile Val His Pro
    290                 295                 300

Met Lys Ser Arg Leu Arg Arg Thr Met Leu Val Ala Lys Val Thr Cys
305                 310                 315                 320

Ile Ile Ile Trp Leu Leu Ala Gly Leu Ala Ser Leu Pro Ala Ile Ile
                325                 330                 335

His Arg Asn Val Phe Phe Ile Glu Asn Thr Asn Ile Thr Val Cys Ala
            340                 345                 350

Phe His Tyr Glu Ser Gln Asn Ser Thr Leu Pro Ile Gly Leu Gly Leu
        355                 360                 365

Thr Lys Asn Ile Leu Gly Phe Leu Phe Pro Phe Leu Ile Ile Leu Thr
    370                 375                 380

Ser Tyr Thr Leu Ile Trp Lys Ala Leu Lys Lys Ala Tyr Glu Ile Gln
385                 390                 395                 400

Lys Asn Lys Pro Arg Asn Asp Asp Ile Phe Lys Ile Ile Met Ala Ile
                405                 410                 415

Val Leu Phe Phe Phe Phe Ser Trp Ile Pro His Gln Ile Phe Thr Phe
            420                 425                 430

Leu Asp Val Leu Ile Gln Leu Gly Ile Ile Arg Asp Cys Arg Ile Ala
        435                 440                 445

Asp Ile Val Asp Thr Ala Met Pro Ile Thr Ile Cys Ile Ala Tyr Phe
    450                 455                 460

Asn Asn Cys Leu Asn Pro Leu Phe Tyr Gly Phe Leu Gly Lys Lys Phe
465                 470                 475                 480

Lys Arg Tyr Phe Leu Gln Leu Leu Lys Tyr Ile Pro Pro Lys Ala Lys
                485                 490                 495

Ser His Ser Asn Leu Ser Thr Lys Met Ser Thr Leu Ser Tyr Arg Pro
            500                 505                 510

Ser Asp Asn Val Ser Ser Ser Thr Lys Lys Pro Ala Pro Cys Phe Glu
        515                 520                 525

Val Glu
530

<210> SEQ ID NO 10
<211> LENGTH: 528
<212> TYPE: PRT
<213> ORGANISM: Artificial Sequence
<220> FEATURE:
<223> OTHER INFORMATION: synthetic fusion protein

<400> SEQUENCE: 10

Met Lys Thr Ile Ile Ala Leu Ser Tyr Ile Phe Cys Leu Val Phe Ala
1               5                   10                  15

```
Asp Tyr Lys Asp Asp Asp Ala Glu Asn Leu Tyr Phe Gln Gly Asn
         20                  25                  30
Ile Phe Glu Met Leu Arg Ile Asp Glu Gly Leu Arg Leu Lys Ile Tyr
         35                  40                  45
Lys Asp Thr Glu Gly Tyr Tyr Thr Ile Gly Ile Gly His Leu Leu Thr
 50                      55                  60
Lys Ser Pro Ser Leu Asn Ala Ala Lys Ser Glu Leu Asp Lys Ala Ile
 65                  70                  75                  80
Gly Arg Asn Thr Asn Gly Val Ile Thr Lys Asp Glu Ala Glu Lys Leu
                 85                  90                  95
Phe Asn Gln Asp Val Asp Ala Ala Val Arg Gly Ile Leu Arg Asn Ala
             100                 105                 110
Lys Leu Lys Pro Val Tyr Asp Ser Leu Asp Ala Val Arg Arg Ala Ala
         115                 120                 125
Leu Ile Asn Met Val Phe Gln Met Gly Glu Thr Gly Val Ala Gly Phe
     130                 135                 140
Thr Asn Ser Leu Arg Met Leu Gln Gln Lys Arg Trp Asp Glu Ala Ala
145                 150                 155                 160
Val Asn Leu Ala Lys Ser Arg Trp Tyr Asn Gln Thr Pro Asn Arg Ala
                 165                 170                 175
Lys Arg Val Ile Thr Thr Phe Arg Thr Gly Thr Trp Asp Ala Tyr Ala
             180                 185                 190
Ala Ser Met Ile Thr Ala Thr Thr Ile Met Ala Leu Tyr Ser Ile Val
         195                 200                 205
Cys Val Val Gly Leu Phe Gly Asn Phe Leu Val Met Tyr Val Ile Val
     210                 215                 220
Arg Tyr Thr Lys Met Lys Thr Ala Thr Asn Ile Tyr Ile Phe Asn Leu
225                 230                 235                 240
Ala Leu Ala Asp Ala Leu Ala Thr Ser Thr Leu Pro Phe Gln Ser Val
                 245                 250                 255
Asn Tyr Leu Met Gly Thr Trp Pro Phe Gly Thr Ile Leu Cys Lys Ile
             260                 265                 270
Val Ile Ser Ile Asp Tyr Tyr Asn Met Phe Thr Ser Ile Phe Thr Leu
         275                 280                 285
Cys Thr Met Ser Val Asp Arg Tyr Ile Ala Val Cys His Pro Val Lys
     290                 295                 300
Ala Leu Asp Phe Arg Thr Pro Arg Asn Ala Lys Ile Ile Asn Val Cys
305                 310                 315                 320
Asn Trp Ile Leu Ser Ser Ala Ile Gly Leu Pro Val Met Phe Met Ala
                 325                 330                 335
Thr Thr Lys Tyr Arg Gln Gly Ser Ile Asp Cys Thr Leu Thr Phe Ser
             340                 345                 350
His Pro Thr Trp Tyr Trp Glu Asn Leu Leu Lys Ile Cys Val Phe Ile
         355                 360                 365
Phe Ala Phe Ile Met Pro Val Leu Ile Ile Thr Val Cys Tyr Gly Leu
     370                 375                 380
Met Ile Leu Arg Leu Lys Ser Val Arg Met Leu Ser Gly Ser Lys Glu
385                 390                 395                 400
Lys Asp Arg Asn Leu Arg Arg Ile Thr Arg Met Val Leu Val Val Val
                 405                 410                 415
Ala Val Phe Ile Val Cys Trp Thr Pro Ile His Ile Tyr Val Ile Ile
             420                 425                 430
```

```
Lys Ala Leu Val Thr Ile Pro Glu Thr Thr Phe Gln Thr Val Ser Trp
            435                 440                 445

His Phe Cys Ile Ala Leu Gly Tyr Thr Asn Ser Cys Leu Asn Pro Val
    450                 455                 460

Leu Tyr Ala Phe Leu Asp Glu Asn Phe Lys Arg Cys Phe Arg Glu Phe
465                 470                 475                 480

Cys Ile Pro Thr Ser Ser Asn Ile Glu Gln Gln Asn Ser Thr Arg Ile
                485                 490                 495

Arg Gln Asn Thr Arg Asp His Pro Ser Thr Ala Asn Thr Val Asp Arg
            500                 505                 510

Thr Asn His Gln Leu Glu Asn Leu Glu Ala Gly Thr Ala Pro Leu Pro
            515                 520                 525
```

<210> SEQ ID NO 11
<211> LENGTH: 543
<212> TYPE: PRT
<213> ORGANISM: Artificial Sequence
<220> FEATURE:
<223> OTHER INFORMATION: synthetic fusion protein

<400> SEQUENCE: 11

```
Met Lys Thr Ile Ile Ala Leu Ser Tyr Ile Phe Cys Leu Val Phe Ala
1               5                   10                  15

Asp Tyr Lys Asp Asp Asp Ala Glu Asn Leu Tyr Phe Gln Gly Asn
            20                  25                  30

Ile Phe Glu Met Leu Arg Ile Asp Glu Gly Leu Arg Leu Lys Ile Tyr
                35                  40                  45

Lys Asp Thr Glu Gly Tyr Tyr Thr Ile Gly Ile Gly His Leu Leu Thr
50                  55                  60

Lys Ser Pro Ser Leu Asn Ala Ala Lys Ser Glu Leu Asp Lys Ala Ile
65                  70                  75                  80

Gly Arg Asn Thr Asn Gly Val Ile Thr Lys Asp Glu Ala Glu Lys Leu
                85                  90                  95

Phe Asn Gln Asp Val Asp Ala Ala Val Arg Gly Ile Leu Arg Asn Ala
            100                 105                 110

Lys Leu Lys Pro Val Tyr Asp Ser Leu Asp Ala Val Arg Arg Ala Ala
        115                 120                 125

Leu Ile Asn Met Val Phe Gln Met Gly Glu Thr Gly Val Ala Gly Phe
130                 135                 140

Thr Asn Ser Leu Arg Met Leu Gln Gln Lys Arg Trp Asp Glu Ala Ala
145                 150                 155                 160

Val Asn Leu Ala Lys Ser Arg Trp Tyr Asn Gln Thr Pro Asn Arg Ala
                165                 170                 175

Lys Arg Val Ile Thr Thr Phe Arg Thr Gly Thr Trp Asp Ala Tyr Ala
            180                 185                 190

Ala Leu Pro Leu Ala Met Ile Phe Thr Leu Ala Leu Ala Tyr Gly Ala
        195                 200                 205

Val Ile Ile Leu Gly Val Ser Gly Asn Leu Ala Leu Ile Ile Ile Ile
210                 215                 220

Leu Lys Gln Lys Glu Met Arg Asn Val Thr Asn Ile Leu Ile Val Asn
225                 230                 235                 240

Leu Ser Phe Ser Asp Leu Leu Val Ala Ile Met Cys Leu Pro Leu Thr
                245                 250                 255

Phe Val Tyr Thr Leu Met Asp His Trp Val Phe Gly Glu Ala Met Cys
            260                 265                 270
```

-continued

```
Lys Leu Asn Pro Phe Val Gln Cys Val Ser Ile Thr Val Ser Ile Phe
            275                 280                 285

Ser Leu Val Leu Ile Ala Val Glu Arg His Gln Leu Ile Ile Asn Pro
        290                 295                 300

Arg Gly Trp Arg Pro Asn Asn Arg His Ala Tyr Val Gly Ile Ala Val
305                 310                 315                 320

Ile Trp Val Leu Ala Val Ala Ser Ser Leu Pro Phe Leu Ile Tyr Gln
                325                 330                 335

Val Met Thr Asp Glu Pro Phe Gln Asn Val Thr Leu Asp Ala Tyr Lys
                    340                 345                 350

Asp Lys Tyr Val Cys Phe Asp Gln Phe Pro Ser Asp Ser His Arg Leu
                355                 360                 365

Ser Tyr Thr Thr Leu Leu Leu Val Leu Gln Tyr Phe Gly Pro Leu Cys
        370                 375                 380

Phe Ile Phe Ile Cys Tyr Phe Lys Ile Tyr Ile Arg Leu Lys Arg Arg
385                 390                 395                 400

Asn Asn Met Met Asp Lys Met Arg Asp Asn Lys Tyr Arg Ser Ser Glu
                405                 410                 415

Thr Lys Arg Ile Asn Ile Met Leu Leu Ser Ile Val Val Ala Phe Ala
                    420                 425                 430

Val Cys Trp Leu Pro Leu Thr Ile Phe Asn Thr Val Phe Asp Trp Asn
        435                 440                 445

His Gln Ile Ile Ala Thr Cys Asn His Asn Leu Leu Phe Leu Leu Cys
    450                 455                 460

His Leu Thr Ala Met Ile Ser Thr Cys Val Asn Pro Ile Phe Tyr Gly
465                 470                 475                 480

Phe Leu Asn Lys Asn Phe Gln Arg Asp Leu Gln Phe Phe Asn Phe
                485                 490                 495

Cys Asp Phe Arg Ser Arg Asp Asp Tyr Glu Thr Ile Ala Met Ser
                500                 505                 510

Thr Met His Thr Asp Val Ser Lys Thr Ser Leu Lys Gln Ala Ser Pro
                515                 520                 525

Val Ala Phe Lys Lys Ile Asn Asn Asn Asp Asp Asn Glu Lys Ile
530                 535                 540

<210> SEQ ID NO 12
<211> LENGTH: 482
<212> TYPE: PRT
<213> ORGANISM: Artificial Sequence
<220> FEATURE:
<223> OTHER INFORMATION: synthetic fusion protein

<400> SEQUENCE: 12

Met Lys Thr Ile Ile Ala Leu Ser Tyr Ile Phe Cys Leu Val Phe Ala
1               5                   10                  15

Asp Tyr Lys Asp Asp Asp Asp Ala Glu Asn Leu Tyr Phe Gln Gly Asn
                20                  25                  30

Ile Phe Glu Met Leu Arg Ile Asp Glu Gly Leu Arg Leu Lys Ile Tyr
            35                  40                  45

Lys Asp Thr Glu Gly Tyr Tyr Thr Ile Gly Ile Gly His Leu Leu Thr
50                  55                  60

Lys Ser Pro Ser Leu Asn Ala Ala Lys Ser Glu Leu Asp Lys Ala Ile
65                  70                  75                  80

Gly Arg Asn Thr Asn Gly Val Ile Thr Lys Asp Glu Ala Glu Lys Leu
                85                  90                  95
```

Phe Asn Gln Asp Val Asp Ala Ala Val Arg Gly Ile Leu Arg Asn Ala
            100                 105                 110
Lys Leu Lys Pro Val Tyr Asp Ser Leu Asp Ala Val Arg Arg Ala Ala
        115                 120                 125
Leu Ile Asn Met Val Phe Gln Met Gly Glu Thr Gly Val Ala Gly Phe
    130                 135                 140
Thr Asn Ser Leu Arg Met Leu Gln Gln Lys Arg Trp Asp Glu Ala Ala
145                 150                 155                 160
Val Asn Leu Ala Lys Ser Arg Trp Tyr Asn Gln Thr Pro Asn Arg Ala
                165                 170                 175
Lys Arg Val Ile Thr Thr Phe Arg Thr Gly Thr Trp Asp Ala Tyr Ala
            180                 185                 190
Ala Trp Pro His Leu Glu Val Val Ile Phe Val Val Leu Ile Phe
        195                 200                 205
Tyr Leu Met Thr Leu Ile Gly Asn Leu Phe Ile Ile Ile Leu Ser Tyr
    210                 215                 220
Leu Asp Ser His Leu His Thr Pro Met Tyr Phe Phe Leu Ser Asn Leu
225                 230                 235                 240
Ser Phe Leu Asp Leu Cys Tyr Thr Thr Ser Ser Ile Pro Gln Leu Leu
                245                 250                 255
Val Asn Leu Trp Gly Pro Glu Lys Thr Ile Ser Tyr Ala Gly Cys Met
            260                 265                 270
Ile Gln Leu Tyr Phe Val Leu Ala Leu Gly Thr Ala Glu Cys Val Leu
        275                 280                 285
Leu Val Val Met Ser Tyr Asp Arg Tyr Ala Ala Val Cys Arg Pro Leu
    290                 295                 300
His Tyr Thr Val Leu Met His Pro Arg Phe Cys His Leu Leu Ala Val
305                 310                 315                 320
Ala Ser Trp Val Ser Gly Phe Thr Asn Ser Ala Leu His Ser Ser Phe
                325                 330                 335
Thr Phe Trp Val Pro Leu Cys Gly His Arg Gln Val Asp His Phe Phe
            340                 345                 350
Cys Glu Val Pro Ala Leu Leu Arg Leu Ser Cys Val Asp Thr His Val
        355                 360                 365
Asn Glu Leu Thr Leu Met Ile Thr Ser Ser Ile Phe Val Leu Ile Pro
    370                 375                 380
Leu Ile Leu Ile Leu Thr Ser Tyr Gly Ala Ile Val Gln Ala Val Leu
385                 390                 395                 400
Arg Met Gln Ser Thr Thr Gly Leu Gln Lys Val Phe Gly Thr Cys Gly
                405                 410                 415
Ala His Leu Met Ala Val Ser Leu Phe Phe Ile Pro Ala Met Cys Ile
            420                 425                 430
Tyr Leu Gln Pro Pro Ser Gly Asn Ser Gln Asp Gln Gly Lys Phe Ile
        435                 440                 445
Ala Leu Phe Tyr Thr Val Val Thr Pro Ser Leu Asn Pro Leu Ile Tyr
    450                 455                 460
Thr Leu Arg Asn Lys Val Val Arg Gly Ala Val Lys Arg Leu Met Gly
465                 470                 475                 480
Trp Glu

<210> SEQ ID NO 13
<211> LENGTH: 570
<212> TYPE: PRT
<213> ORGANISM: Artificial Sequence
<220> FEATURE:
<223> OTHER INFORMATION: synthetic fusion protein

<400> SEQUENCE: 13

```
Met Lys Thr Ile Ile Ala Leu Ser Tyr Ile Phe Cys Leu Val Phe Ala
1               5                   10                  15

Asp Tyr Lys Asp Asp Asp Ala Glu Asn Leu Tyr Phe Gln Gly Asn
            20              25                  30

Ile Phe Glu Met Leu Arg Ile Asp Glu Gly Leu Arg Leu Lys Ile Tyr
                35                  40                  45

Lys Asp Thr Glu Gly Tyr Tyr Thr Ile Gly Ile Gly His Leu Leu Thr
        50                  55                  60

Lys Ser Pro Ser Leu Asn Ala Ala Lys Ser Glu Leu Asp Lys Ala Ile
65                  70                  75                  80

Gly Arg Asn Thr Asn Gly Val Ile Thr Lys Asp Glu Ala Glu Lys Leu
                85                  90                  95

Phe Asn Gln Asp Val Asp Ala Ala Val Arg Gly Ile Leu Arg Asn Ala
                100                 105                 110

Lys Leu Lys Pro Val Tyr Asp Ser Leu Asp Ala Val Arg Arg Ala Ala
            115                 120                 125

Leu Ile Asn Met Val Phe Gln Met Gly Glu Thr Gly Val Ala Gly Phe
        130                 135                 140

Thr Asn Ser Leu Arg Met Leu Gln Gln Lys Arg Trp Asp Glu Ala Ala
145                 150                 155                 160

Val Asn Leu Ala Lys Ser Arg Trp Tyr Asn Gln Thr Pro Asn Arg Ala
                165                 170                 175

Lys Arg Val Ile Thr Thr Phe Arg Thr Gly Thr Trp Asp Ala Tyr Ala
            180                 185                 190

Ala Leu Glu Tyr Gln Val Val Thr Ile Leu Leu Val Leu Ile Ile Cys
        195                 200                 205

Gly Leu Gly Ile Val Gly Asn Ile Met Val Val Leu Val Val Met Arg
        210                 215                 220

Thr Lys His Met Arg Thr Pro Thr Asn Cys Tyr Leu Val Ser Leu Ala
225                 230                 235                 240

Val Ala Asp Leu Met Val Leu Val Ala Ala Gly Leu Pro Asn Ile Thr
                245                 250                 255

Asp Ser Ile Tyr Gly Ser Trp Val Tyr Gly Tyr Val Gly Cys Leu Cys
            260                 265                 270

Ile Thr Tyr Leu Gln Tyr Leu Gly Ile Asn Ala Ser Ser Cys Ser Ile
        275                 280                 285

Thr Ala Phe Thr Ile Glu Arg Tyr Ile Ala Ile Cys His Pro Ile Lys
        290                 295                 300

Ala Gln Phe Leu Cys Thr Phe Ser Arg Ala Lys Lys Ile Ile Ile Phe
305                 310                 315                 320

Val Trp Ala Phe Thr Ser Leu Tyr Cys Met Leu Trp Phe Phe Leu Leu
                325                 330                 335

Asp Leu Asn Ile Ser Thr Tyr Lys Asp Ala Ile Val Ile Ser Cys Gly
            340                 345                 350

Tyr Lys Ile Ser Arg Asn Tyr Tyr Ser Pro Ile Tyr Leu Met Asp Phe
        355                 360                 365

Gly Val Phe Tyr Val Val Pro Met Ile Leu Ala Thr Val Leu Tyr Gly
    370                 375                 380

Phe Ile Ala Arg Ile Leu Phe Leu Asn Pro Ile Pro Ser Asp Pro Lys
385                 390                 395                 400
```

```
Glu Asn Ser Lys Thr Trp Lys Asn Asp Ser Thr His Gln Asn Thr Asn
                405                 410                 415
Leu Asn Val Asn Thr Ser Asn Arg Cys Phe Asn Ser Thr Val Ser Ser
            420                 425                 430
Arg Lys Gln Val Thr Lys Met Leu Ala Val Val Ile Leu Phe Ala
        435                 440                 445
Leu Leu Trp Met Pro Tyr Arg Thr Leu Val Val Asn Ser Phe Leu
    450                 455                 460
Ser Ser Pro Phe Gln Glu Asn Trp Phe Leu Phe Cys Arg Ile Cys
465             470                 475                 480
Ile Tyr Leu Asn Ser Ala Ile Asn Pro Val Ile Tyr Asn Leu Met Ser
                485                 490                 495
Gln Lys Phe Arg Ala Ala Phe Arg Lys Leu Cys Asn Cys Lys Gln Lys
            500                 505                 510
Pro Thr Glu Lys Pro Ala Asn Tyr Ser Val Ala Leu Asn Tyr Ser Val
            515                 520                 525
Ile Lys Glu Ser Asp His Phe Ser Thr Glu Leu Asp Asp Ile Thr Val
        530                 535                 540
Thr Asp Thr Tyr Leu Ser Ala Thr Lys Val Ser Phe Asp Asp Thr Cys
545             550                 555                 560
Leu Ala Ser Glu Val Ser Phe Ser Gln Ser
                565                 570

<210> SEQ ID NO 14
<211> LENGTH: 8
<212> TYPE: PRT
<213> ORGANISM: Artificial Sequence
<220> FEATURE:
<223> OTHER INFORMATION: synthetic peptide

<400> SEQUENCE: 14

Asp Tyr Lys Asp Asp Asp Asp Ala
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic peptide

<400> SEQUENCE: 15

Glu Asn Leu Tyr Phe Gln Gly
1               5

<210> SEQ ID NO 16
<211> LENGTH: 9
<212> TYPE: PRT
<213> ORGANISM: Artificial Sequence
<220> FEATURE:
<223> OTHER INFORMATION: synthetic peptide

<400> SEQUENCE: 16

Ser Glu Asn Leu Tyr Phe Gln Gly Ser
1               5

<210> SEQ ID NO 17
<211> LENGTH: 502
<212> TYPE: PRT
<213> ORGANISM: Artificial Sequence
<220> FEATURE:
```

<223> OTHER INFORMATION: synthetic fusion protein

<400> SEQUENCE: 17

| | | | | | | | | | | | | | | | |
|---|---|---|---|---|---|---|---|---|---|---|---|---|---|---|---|
| Met | Lys | Thr | Ile | Ile | Ala | Leu | Ser | Tyr | Ile | Phe | Cys | Leu | Val | Phe | Ala |
| 1 | | | | 5 | | | | | 10 | | | | | 15 | |
| Asp | Tyr | Lys | Asp | Asp | Asp | Ala | Glu | Asn | Leu | Tyr | Phe | Gln | Gly | Asn | |
| | | | 20 | | | | | 25 | | | | | 30 | | |
| Ile | Phe | Glu | Met | Leu | Arg | Ile | Asp | Glu | Gly | Leu | Arg | Leu | Lys | Ile | Tyr |
| | | | 35 | | | | | 40 | | | | | 45 | | |
| Lys | Asp | Thr | Glu | Gly | Tyr | Tyr | Thr | Ile | Gly | Ile | Gly | His | Leu | Leu | Thr |
| 50 | | | | | 55 | | | | | 60 | | | | | |
| Lys | Ser | Pro | Ser | Leu | Asn | Ala | Ala | Lys | Ser | Glu | Leu | Asp | Lys | Ala | Ile |
| 65 | | | | | 70 | | | | | 75 | | | | | 80 |
| Gly | Arg | Asn | Thr | Asn | Gly | Val | Ile | Thr | Lys | Asp | Glu | Ala | Glu | Lys | Leu |
| | | | | 85 | | | | | 90 | | | | | 95 | |
| Phe | Asn | Gln | Asp | Val | Asp | Ala | Ala | Val | Arg | Gly | Ile | Leu | Arg | Asn | Ala |
| | | | 100 | | | | | 105 | | | | | 110 | | |
| Lys | Leu | Lys | Pro | Val | Tyr | Asp | Ser | Leu | Asp | Ala | Val | Arg | Arg | Ala | Ala |
| | | | | 115 | | | | | 120 | | | | | 125 | |
| Leu | Ile | Asn | Met | Val | Phe | Gln | Met | Gly | Glu | Thr | Gly | Val | Ala | Gly | Phe |
| 130 | | | | | 135 | | | | | 140 | | | | | |
| Thr | Asn | Ser | Leu | Arg | Met | Leu | Gln | Gln | Lys | Arg | Trp | Asp | Glu | Ala | Ala |
| 145 | | | | | 150 | | | | | 155 | | | | | 160 |
| Val | Asn | Leu | Ala | Lys | Ser | Arg | Trp | Tyr | Asn | Gln | Thr | Pro | Asn | Arg | Ala |
| | | | | 165 | | | | | 170 | | | | | 175 | |
| Lys | Arg | Val | Ile | Thr | Thr | Phe | Arg | Thr | Gly | Thr | Trp | Asp | Ala | Tyr | Ala |
| | | | 180 | | | | | 185 | | | | | 190 | | |
| Ala | Asp | Glu | Val | Trp | Val | Val | Gly | Met | Gly | Ile | Val | Met | Ser | Leu | Ile |
| | | | | 195 | | | | | 200 | | | | | 205 | |
| Val | Leu | Ala | Ile | Val | Phe | Gly | Asn | Val | Leu | Val | Ile | Thr | Ala | Ile | Ala |
| 210 | | | | | 215 | | | | | 220 | | | | | |
| Lys | Phe | Glu | Arg | Leu | Gln | Thr | Val | Thr | Asn | Tyr | Phe | Ile | Thr | Ser | Leu |
| 225 | | | | | 230 | | | | | 235 | | | | | 240 |
| Ala | Cys | Ala | Asp | Leu | Val | Met | Gly | Leu | Ala | Val | Val | Pro | Phe | Gly | Ala |
| | | | | 245 | | | | | 250 | | | | | 255 | |
| Ala | His | Ile | Leu | Thr | Lys | Thr | Trp | Thr | Phe | Gly | Asn | Phe | Trp | Cys | Glu |
| | | | 260 | | | | | 265 | | | | | 270 | | |
| Phe | Trp | Thr | Ser | Ile | Asp | Val | Leu | Cys | Val | Thr | Ala | Ser | Ile | Glu | Thr |
| | | | | 275 | | | | | 280 | | | | | 285 | |
| Leu | Cys | Val | Ile | Ala | Val | Asp | Arg | Tyr | Phe | Ala | Ile | Thr | Ser | Pro | Phe |
| | | | 290 | | | | | 295 | | | | | 300 | | |
| Lys | Tyr | Gln | Ser | Leu | Leu | Thr | Lys | Asn | Lys | Ala | Arg | Val | Ile | Ile | Leu |
| 305 | | | | | 310 | | | | | 315 | | | | | 320 |
| Met | Val | Trp | Ile | Val | Ser | Gly | Leu | Thr | Ser | Phe | Leu | Pro | Ile | Gln | Met |
| | | | | 325 | | | | | 330 | | | | | 335 | |
| His | Trp | Tyr | Arg | Ala | Thr | His | Gln | Glu | Ala | Ile | Asn | Cys | Tyr | Ala | Glu |
| | | | 340 | | | | | 345 | | | | | 350 | | |
| Glu | Thr | Cys | Cys | Asp | Phe | Phe | Thr | Asn | Gln | Ala | Tyr | Ala | Ile | Ala | Ser |
| | | | | 355 | | | | | 360 | | | | | 365 | |
| Ser | Ile | Val | Ser | Phe | Tyr | Val | Pro | Leu | Val | Ile | Met | Val | Phe | Val | Tyr |
| | | | 370 | | | | | 375 | | | | | 380 | | |
| Ser | Arg | Val | Phe | Gln | Glu | Ala | Lys | Arg | Gln | Leu | Gln | Lys | Ile | Asp | Lys |
| 385 | | | | | 390 | | | | | 395 | | | | | 400 |

```
Phe Cys Leu Lys Glu His Lys Ala Leu Lys Thr Leu Gly Ile Ile Met
                405                 410                 415

Gly Thr Phe Thr Leu Cys Trp Leu Pro Phe Phe Ile Val Asn Ile Val
            420                 425                 430

His Val Ile Gln Asp Asn Leu Ile Arg Lys Glu Val Tyr Ile Leu Leu
        435                 440                 445

Asn Trp Ile Gly Tyr Val Asn Ser Gly Phe Asn Pro Leu Ile Tyr Cys
    450                 455                 460

Arg Ser Pro Asp Phe Arg Ile Ala Phe Gln Glu Leu Leu Cys Leu Arg
465                 470                 475                 480

Arg Ser Ser Leu Lys Ala Tyr Gly Asn Gly Tyr Ser Ser Asn Gly Asn
                485                 490                 495

Thr Gly Glu Gln Ser Gly
            500

<210> SEQ ID NO 18
<211> LENGTH: 31
<212> TYPE: PRT
<213> ORGANISM: Artificial Sequence
<220> FEATURE:
<223> OTHER INFORMATION: synthetic peptide

<400> SEQUENCE: 18

Met Lys Thr Ile Ile Ala Leu Ser Tyr Ile Phe Cys Leu Val Phe Ala
1               5                   10                  15

Asp Tyr Lys Asp Asp Asp Ala Glu Asn Leu Tyr Phe Gln Gly
            20                  25                  30

<210> SEQ ID NO 19
<211> LENGTH: 413
<212> TYPE: PRT
<213> ORGANISM: Artificial Sequence
<220> FEATURE:
<223> OTHER INFORMATION: synthetic fusion protein

<400> SEQUENCE: 19

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
                20                  25                  30

Val Val Gly Met Gly Ile Val Met Ser Leu Ile Val Leu Ala Ile Val
            35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Thr
                85                  90                  95

Lys Thr Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175
```

```
Thr His Gln Glu Ala Ile Asn Cys Tyr Ala Glu Glu Thr Cys Cys Asp
            180                 185                 190

Phe Phe Thr Asn Gln Ala Tyr Ala Ile Ala Ser Ser Ile Val Ser Phe
            195                 200                 205

Tyr Val Pro Leu Val Ile Met Val Phe Val Tyr Ser Arg Val Phe Gln
210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
            245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
            275                 280                 285

Phe Phe Ile Val Asn Ile Val His Val Ile Gln Asp Asn Leu Ile Arg
            290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
            325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
            355                 360                 365

Glu Gln Glu Lys Glu Asn Lys Leu Leu Cys Glu Asp Leu Pro Gly Thr
370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410

<210> SEQ ID NO 20
<211> LENGTH: 4
<212> TYPE: PRT
<213> ORGANISM: Artificial Sequence
<220> FEATURE:
<223> OTHER INFORMATION: synthetic peptide

<400> SEQUENCE: 20

Arg Thr Val Trp
1

<210> SEQ ID NO 21
<211> LENGTH: 5
<212> TYPE: PRT
<213> ORGANISM: Artificial Sequence
<220> FEATURE:
<223> OTHER INFORMATION: synthetic peptide

<400> SEQUENCE: 21

Arg Thr Glu Val Trp
1               5

<210> SEQ ID NO 22
<211> LENGTH: 6
<212> TYPE: PRT
<213> ORGANISM: Artificial Sequence
<220> FEATURE:
<223> OTHER INFORMATION: synthetic peptide
```

<400> SEQUENCE: 22

Arg Thr Asp Glu Val Trp
1               5

<210> SEQ ID NO 23
<211> LENGTH: 7
<212> TYPE: PRT
<213> ORGANISM: Artificial Sequence
<220> FEATURE:
<223> OTHER INFORMATION: synthetic peptide

<400> SEQUENCE: 23

Arg Thr Ala Asp Glu Val Trp
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic peptide

<400> SEQUENCE: 24

Arg Thr Ala Ala Asp Glu Val Trp
1               5

<210> SEQ ID NO 25
<211> LENGTH: 9
<212> TYPE: PRT
<213> ORGANISM: Artificial Sequence
<220> FEATURE:
<223> OTHER INFORMATION: synthetic peptide

<400> SEQUENCE: 25

Arg Thr Ala Ala Ala Asp Glu Val Trp
1               5

<210> SEQ ID NO 26
<211> LENGTH: 12
<212> TYPE: PRT
<213> ORGANISM: Artificial Sequence
<220> FEATURE:
<223> OTHER INFORMATION: synthetic peptide

<400> SEQUENCE: 26

Arg Thr Gly Thr Trp Asp Ala Tyr Asp Glu Val Trp
1               5                   10

<210> SEQ ID NO 27
<211> LENGTH: 13
<212> TYPE: PRT
<213> ORGANISM: Artificial Sequence
<220> FEATURE:
<223> OTHER INFORMATION: synthetic peptide

<400> SEQUENCE: 27

Arg Thr Gly Thr Trp Asp Ala Tyr Ala Asp Glu Val Trp
1               5                   10

<210> SEQ ID NO 28
<211> LENGTH: 14
<212> TYPE: PRT
<213> ORGANISM: Artificial Sequence
<220> FEATURE:
<223> OTHER INFORMATION: synthetic peptide

```
<400> SEQUENCE: 28

Arg Thr Gly Thr Trp Asp Ala Tyr Ala Ala Asp Glu Val Trp
1               5                   10

<210> SEQ ID NO 29
<211> LENGTH: 15
<212> TYPE: PRT
<213> ORGANISM: Artificial Sequence
<220> FEATURE:
<223> OTHER INFORMATION: synthetic peptide

<400> SEQUENCE: 29

Arg Thr Gly Thr Trp Asp Ala Tyr Ala Ala Ala Asp Glu Val Trp
1               5                   10                  15
```

GPCR FUSION PROTEIN CONTAINING AN N-TERMINAL AUTONOMOUSLY FOLDING STABLE DOMAIN, AND CRYSTALS OF THE SAME

CROSS-REFERENCING

This application claims the benefit of U.S. provisional application Ser. Nos. 61/453,020, filed Mar. 15, 2011 and 61/507,425, filed Jul. 13, 2011, which are incorporated by reference in their entirety.

GOVERNMENT RIGHTS

This invention was made with Government support under contract GM083118 awarded by the National Institutes of Health. The Government has certain rights in this invention.

BACKGROUND

G protein-coupled receptor (GPCR) signaling plays a vital role in a number of physiological contexts including, but not limited to, metabolism, inflammation, neuronal function, and cardiovascular function. For instance, GPCRs include receptors for biogenic amines, e.g., dopamine, epinephrine, histamine, glutamate, acetylcholine, and serotonin; for purines such as ADP and ATP; for the vitamin niacin; for lipid mediators of inflammation such as prostaglandins, lipoxins, platelet activating factor, and leukotrienes; for peptide hormones such as calcitonin, follicle stimulating hormone, gonadotropin releasing hormone, ghrelin, motilin, neurokinin, and oxytocin; for non-hormone peptides such as beta-endorphin, dynorphin A, Leu-enkephalin, and Met-enkephalin; for the non-peptide hormone melatonin; for polypeptides such as C5a anaphylatoxin and chemokines; for proteases such as thrombin, trypsin, and factor Xa; and for sensory signal mediators, e.g., retinal photopigments and olfactory stimulatory molecules. GPCRs are of immense interest for drug development.

SUMMARY

A GPCR fusion protein is provided. In certain embodiments, the GPCR fusion protein comprises: a) a G-protein coupled receptor (GPCR); and b) an autonomously folding stable domain, where the autonomously folding stable domain is N-terminal to the GPCR and is heterologous to the GPCR. The GPCR fusion protein is characterized in that is crystallizable under lipidic cubic phase crystallization conditions. In certain embodiments, the GPCR fusion protein may be crystallizable in a complex with a G-protein or in a complex with an antibody that binds to the IC3 loop of the GPCR.

In particular embodiments, the GPCR fusion protein may further comprise an epitope tag N-terminal to the autonomously folding stable domain. In some cases, the GPCR fusion protein may further comprise a protease cleavage site between the epitope tag and the autonomously folding stable domain, thereby allowing the epitope tag to cleaved off.

In particular embodiments, the autonomously folding stable domain may comprises the amino acid sequence of lysozyme. In some cases, the GPCR fusion protein may also comprise a second autonomously folding stable domain between the TM5 and TM6 regions of the GPCR (i.e., in the IC3 loop of the GPCR).

In certain embodiments, the GPCR of the fusion protein may be active. The GPCR of the fusion protein may be naturally occurring or non-naturally occurring.

Also provided is a composition of matter comprising: a) a subject GPCR fusion protein; and b) a moiety complexed with the GPCR fusion protein. The moiety complexed with the GPCR fusion protein may be, for example, a G-protein or an antibody that is bound to the IC3 loop of the GPCR. The moiety may also be a ligand for the GPCR.

A nucleic acid encoding the subject GPCR fusion protein is also provided. In particular embodiments, the nucleic acid may encode, from 5' to 3': a) a signal sequence; b) an epitope tag; c) a protease cleavage site; d) an autonomously folding stable domain; and e) a GPCR. Also provided is a cell containing the nucleic acid. In particular cases, the fusion protein may be expressed in the cell, and disposed on the plasma membrane of the cell.

Also provided is a crystal comprising a crystalline form of the subject GPCR fusion protein. The crystal may further contain, for example, a G protein complexed with the GPCR fusion protein, a ligand for the GPCR, or an antibody that is bound to the IC3 loop of the GPCR. In particular embodiments, the crystallized GPCR fusion protein may comprise a second autonomously folding stable domain between the TM5 and TM6 regions of the GPCR.

Also provided is a method for producing the subject fusion protein. In some embodiments, this method may involve culturing the above-described cell to produce the GPCR fusion protein; and isolating the GPCR fusion protein from the cell. The may further comprises crystallizing the GPCR fusion protein to make crystals, e.g., using a bicelle crystallization method or a lipidic cubic phase crystallization method. Prior to crystallization, the isolated GPCR fusion protein may be combined with a moiety to which it complexes, e.g., the G protein to which it couples, a ligand or an antibody, for example, to produce a complexes. This method may further comprise obtaining atomic coordinates of the GPCR fusion protein from said crystal.

A method of determining a crystal structure is also provided. In certain cases this method comprises: receiving a subject GPCR fusion protein, crystallizing the fusion protein to produce a crystal; and obtaining atomic coordinates of the fusion protein from the crystal. Other embodiment include forwarding a subject GPCR fusion protein to a remote location, and receiving atomic coordinates for said GPCR fusion protein.

In particular embodiments, a composition comprising a fusion protein in crystalline form is provided in which the fusion protein comprises: a) a G-protein coupled receptor (GPCR); and b) a lysozyme domain, where the lysozyme domain is N-terminal to the GPCR.

In particular embodiments, the GPCR may comprise the amino acid sequence of a naturally occurring GPCR. In other embodiments, GPCR may comprise the amino acid sequence of a non-naturally occurring GPCR.

The domain, in certain cases, may comprise an amino acid sequence having at least 80% identity to the amino acid sequence of a wild-type lysozyme. For example, in certain cases, the domain may comprise an amino acid sequence that is at least 95% identical to the amino acid sequence of T4 lysozyme.

In particular embodiments, the GPCR may be a family A GPCR, a family B GPCR or a family C GCPR. In particular embodiments, the GPCR may be a receptor for a biogenic amine, a dopamine receptor, a seratonin receptor, an adrenergic receptor, a β2-adrenergic receptor, a melanocortin receptor subtype 4, a ghrelin receptor, a metabotropic glutamate receptor or a chemokine receptor. The crystallized GPCR fusion protein may comprise a second autonomously folding stable domain (e.g., another lysozyme domain) between the TM5 and TM6 regions of the GPCR.

In some embodiments, the fusion protein is bound to a ligand for the GPCR. In particular embodiments, the fusion protein may be co-crystallized with a G protein to which the GPCR couples (which may be composed of the Gα, β and γ subunits) or an antibody that binds the IC3 loop of the GPCR, for example.

In particular cases, a GPCR-G-protein complex may be crystallized in conjunction with an antibody that stabilizes the G-protein in the same way as the nanobody described below. Such an antibody may be from any species and, in certain cases, may be a single chain antibody.

BRIEF DESCRIPTION OF THE FIGURES

FIG. 4 shows exemplary sequences that may be employed in place of the lysozyme sequences of FIG. 5. From top to bottom, SEQ ID NOS: 2-6.

FIG. 5 shows the amino acid sequence of an exemplary fusion protein. SEQ ID NO:1. The HA signal peptide is shown in unbolded italic letters; the FLAG epitope tag is shown in underlined letters; the TEV recognition sequence is marked with non-underlined bold letters and the cleavage site is shown in asterisk. The full length T4L is shown by bold underlined letters and the $β_2AR$ sequence from Asp29 to Gly365 is shown by bold, underlined, italicized letters.

FIG. 6 shows the amino acid sequences of further exemplary fusion proteins. SEQ ID NOS: 7-13. The HA signal peptide is shown in unbolded italic letters; the FLAG epitope tag is shown in underlined letters; the TEV recognition sequence is marked with non-underlined bold letters and the cleavage site is shown in asterisk. The full length T4L is shown by bold underlined letters and the GPCR sequence is shown by bold, underlined, italicized letters.

Certain of the figures described above are shown in color in U.S. provisional application Ser. Nos. 61/453,020, filed Mar. 15, 2011 and 61/507,425, filed Jul. 13, 2011. Those color figures, the brief description of those figures, and all references to color figures in those applications are incorporated by reference herein.

DEFINITIONS

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with general dictionaries of many of the terms used in this disclosure. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Figure 1:
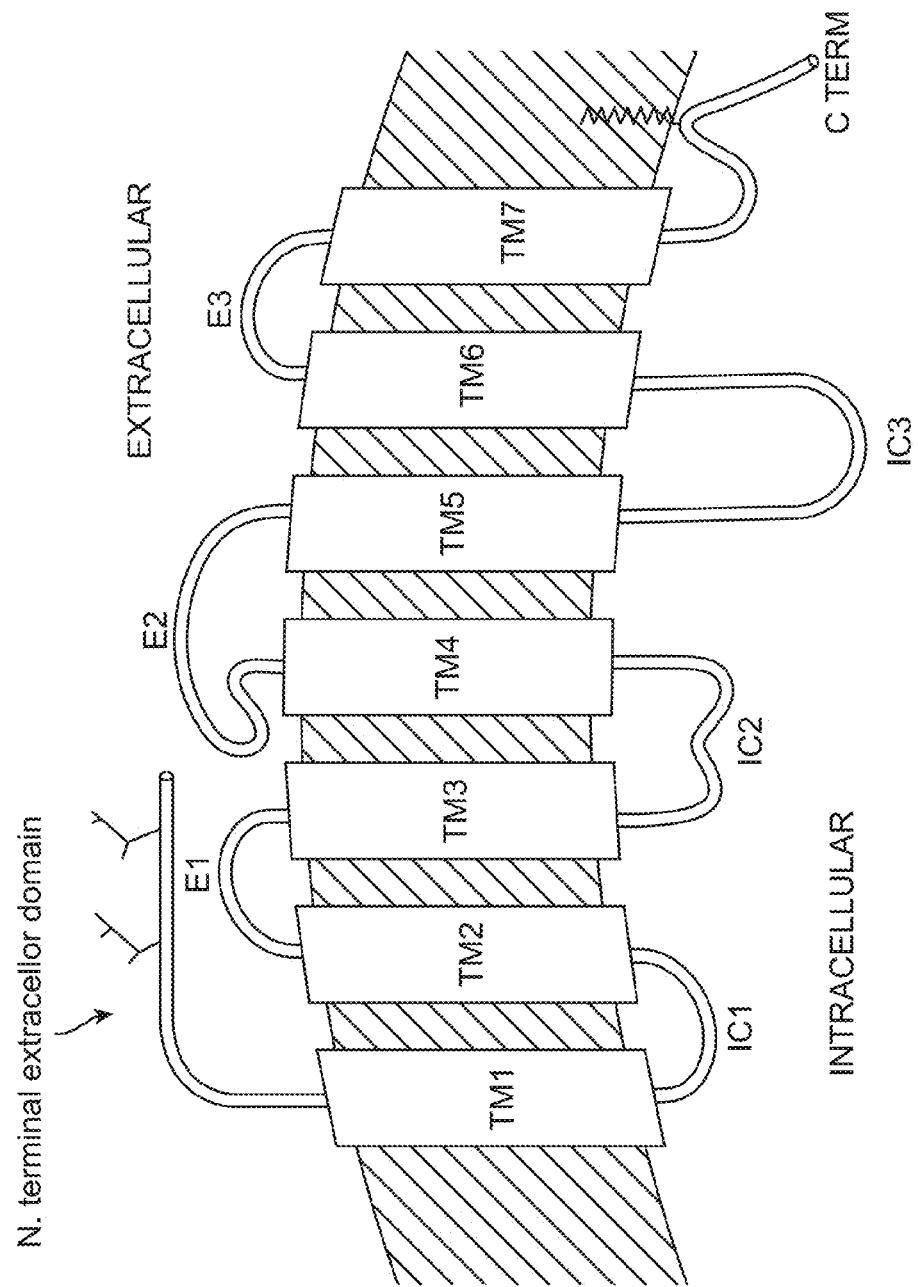
FIG. 1 is a schematic illustration of a GPCR, showing the canonical transmembrane regions (TM1, TM2, TM3, TM4, TM5, TM6, and TM7), intracellular regions (IC1, IC2, and IC3), and extracellular regions (EC1, EC2, and EC3).

"G-protein coupled receptors", or "GPCRs" are polypeptides that share a common structural motif, having seven regions of between 22 to 24 hydrophobic amino acids that form seven alpha helices, each of which spans a membrane. As illustrated in FIG. 1, each span is identified by number, i.e., transmembrane-1 (TM1), transmembrane-2 (TM2), etc. The transmembrane helices are joined by regions of amino acids between transmembrane-2 and transmembrane-3, transmembrane-4 and transmembrane-5, and transmembrane-6 and transmembrane-7 on the exterior, or "extracellular" side, of the cell membrane, referred to as "extracellular" regions 1, 2 and 3 (EC1, EC2 and EC3), respectively. The transmembrane helices are also joined by regions of amino acids between transmembrane-1 and transmembrane-2, transmembrane-3 and transmembrane-4, and transmembrane-5 and transmembrane-6 on the interior, or "intracellular" side, of the cell membrane, referred to as "intracellular" regions 1, 2 and 3 (IC1, IC2 and IC3), respectively. The "carboxy" ("C") terminus of the receptor lies in the intracellular space within the cell, and the "amino" ("N") terminus of the receptor lies in the extracellular space outside of the cell. GPCR structure and classification is generally well known in the art, and further discussion of GPCRs may be found in Probst, DNA Cell Biol. 1992 11:1-20; Marchese et al Genomics 23: 609-618, 1994; and the following books: Jürgen Wess (Ed) Structure-Function Analysis of G Protein-Coupled Receptors published by Wiley-Liss (1st edition; Oct. 15, 1999); Kevin R. Lynch (Ed) Identification and Expression of G Protein-Coupled Receptors published by John Wiley & Sons (March 1998) and Tatsuya Haga (Ed), G Protein-Coupled Receptors, published by CRC Press (Sep. 24, 1999); and Steve Watson (Ed) G-Protein Linked Receptor Factsbook, published by Academic Press (1st edition; 1994). A schematic representation of a typical GPCR is shown in FIG. 1.

The term "naturally-occurring" in reference to a GPCR means a GPCR that is naturally produced (for example and not limitation, by a mammal or by a human). Such GPCRs are found in nature. The term "non-naturally occurring" in reference to a GPCR means a GPCR that is not naturally-occurring. Wild-type GPCRs that have been made constitutively active through mutation, and variants of naturally-occurring GPCRs, e.g., epitope-tagged GPCR and GPCRs lacking their native N-terminus are examples of non-naturally occurring GPCRs. Non-naturally occurring versions of a naturally occurring GPCR are activated by the same ligand as the naturally-occurring GPCR.

The term "ligand" means a molecule that specifically binds to a GPCR. A ligand may be, for example a polypeptide, a lipid, a small molecule, an antibody. A "native ligand" is a ligand that is an endogenous, natural ligand for a native GPCR. A ligand may be a GPCR "antagonist", "agonist", "partial agonist" or "inverse agonist", or the like.

A "modulator" is a ligand that increases or decreases a GPCR intracellular response when it is in contact with, e.g., binds, to a GPCR that is expressed in a cell. This term includes agonists, including partial agonists and inverse agonists, and antagonists.

A "deletion" is defined as a change in either amino acid or nucleotide sequence in which one or more amino acid or nucleotide residues, respectively, are absent as compared to an amino acid sequence or nucleotide sequence of a parental GPCR polypeptide or nucleic acid. In the context of a GPCR or a fragment thereof, a deletion can involve deletion of about 2, about 5, about 10, up to about 20, up to about 30 or up to about 50 or more amino acids. A GPCR or a fragment thereof may contain more than one deletion.

An "insertion" or "addition" is that change in an amino acid or nucleotide sequence which has resulted in the addition of one or more amino acid or nucleotide residues, respectively, as compared to an amino acid sequence or nucleotide sequence of a parental GPCR. "Insertion" generally refers to addition to one or more amino acid residues within an amino acid sequence of a polypeptide, while "addition" can be an insertion or refer to amino acid residues added at an N- or C-terminus, or both termini. In the context of a GPCR or fragment thereof, an insertion or addition is usually of about 1, about 3, about 5, about 10, up to about 20, up to about 30 or up to about 50 or more amino acids. A GPCR or fragment thereof may contain more than one insertion. Reference to particular GPCR or group of GPCRs by name, e.g., reference to the serotonin or histamine receptor, is intended to refer to the wild type receptor as well as active variants of that receptor that can bind to the same ligand as the wild type receptor and/or transduce a signal in the same way as the wild type receptor.

A "substitution" results from the replacement of one or more amino acids or nucleotides by different amino acids or nucleotides, respectively, as compared to an amino acid sequence or nucleotide sequence of a parental GPCR or a fragment thereof. It is understood that a GPCR or a fragment thereof may have conservative amino acid substitutions which have substantially no effect on GPCR activity. By conservative substitutions is intended combinations such as gly, ala; val, ile, leu; asp, glu; asn, gln; ser, thr; lys, arg; and phe, tyr.

The term "biologically active", with respect to a GPCR, refers to a GPCR having a biochemical function (e.g., a binding function, a signal transduction function, or an ability to change conformation as a result of ligand binding) of a naturally occurring GPCR.

As used herein, the terms "determining," "measuring," "assessing," and "assaying" are used interchangeably and include both quantitative and qualitative determinations. Reference to an "amount" of a GPCR in these contexts is not intended to require quantitative assessment, and may be either qualitative or quantitative, unless specifically indicated otherwise.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones.

The term "fusion protein" or grammatical equivalents thereof is meant a protein composed of a plurality of polypeptide components, that while typically unjoined in their native state, are joined by their respective amino and carboxyl termini through a peptide linkage to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the terms are Fab', Fv, F(ab')$_2$, and or other antibody fragments that retain specific binding to antigen.

Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986),). This term also encompasses so-called "phage display" antibodies.

A "monovalent" antibody is an antibody that has a single antigen binding region. Fab fragments, scFv antibodies, and phage display antibodies are types of monovalent antibodies, although others are known. A "Fab" fragment of an antibody has a single binding region, and may be made by papain digestion of a full length monoclonal antibody. A single chain variable (or "scFv") fragment of an antibody is an antibody fragment containing the variable regions of the heavy and light chains of immunoglobulins, linked together with a short flexible linker.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, at least 75% free, or at least 90% free from other components with which it is naturally associated.

A "coding sequence" or a sequence that "encodes" a selected polypeptide, is a nucleic acid molecule which can be transcribed (in the case of DNA) and translated (in the case of mRNA) into a polypeptide, for example, in a host cell when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Operably linked" refers to an arrangement of elements wherein the components so described are configured so as to perform their usual function. In the case of a promoter, a promoter that is operably linked to a coding sequence will effect the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring gene sequences to a host cell. Typically, "vector construct," "expression vector," and "gene transfer vector," mean any nucleic acid construct capable of directing the expression of a gene of interest and which can transfer gene sequences to host cells, which can be accomplished by genomic integration of all or a portion of the vector, or transient or inheritable maintenance of the vector as an extrachromosomal element. Thus, the term includes cloning, and expression vehicles, as well as integrating vectors.

An "expression cassette" comprises any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into a host cell. Thus, the term includes cloning and expression vehicles, as well as viral vectors.

A first polynucleotide is "derived from" or "corresponds to" a second polynucleotide if it has the same or substantially the same nucleotide sequence as a region of the second polynucleotide, its cDNA, complements thereof, or if it displays sequence identity as described above.

A first polypeptide is "derived from" or "corresponds to" a second polypeptide if it is (i) encoded by a first polynucleotide derived from a second polynucleotide, or (ii) displays sequence identity to the second polypeptides as described above.

The term "autonomously folding stable domain" is intended to exclude the amino acid sequence of a reporter protein, e.g., an optically detectable protein such as a fluorescent protein (e.g., GFP, CFP or YFP) or luciferase, and also excludes amino acid sequences that are at least 90% identical to the extracellular of a naturally occurring GPCR.

The term "active form" or "native state" of a protein is a protein that is folded in a way so as to be active. A GPCR is in its active form if it can bind ligand, alter conformation in response to ligand binding, and/or transduce a signal which may or may not be induced by ligand binding. An active or native protein is not denatured.

The term "stable domain" is a polypeptide domain that, when folded in its active form, is stable, i.e., does not readily become inactive or denatured.

The term "folds autonomously" indicates a protein that folds into its active form in a cell, without biochemical denaturation and renaturation of the protein, and without chaperones.

The term "naturally-occurring" refers to an object that is found in nature.

The term "non-naturally-occurring" refers to an object that is not found in nature.

The term "heterologous", in the context of two things that are heterologous to one another, refers to two things that do not exist in the same arrangement in nature.

The term "signal sequence" or "signal peptide" refers to a sequence of amino acids at the N-terminal portion of a protein, which facilitates the secretion of the mature form of the protein through the plasma membrane. The mature form of the protein lacks the signal sequence which is cleaved off during the secretion process.

DETAILED DESCRIPTION OF EXEMPLARY EMBODIMENTS

In the following description, the fusion protein is described first, followed by a discussion of the crystallization method in which the fusion protein may be employed.

Fusion Proteins

As noted above, a subject fusion protein comprise: a) GPCR; and b) an autonomously folding stable domain, where the autonomously folding stable domain is N-terminal to the GPCR and is heterologous to the GPCR. The autonomously folding stable domain is believed to provide a polar surface for crystal lattice contacts on the extracellular surface of the protein, thereby allowing the fusion protein to be crystallized. In particular embodiments, the protein is characterized in that is crystallizable under lipidic cubic phase crystallization conditions, although other crystallization conditions may be employed. A polar surface for crystal lattice contacts on the extracellular surface of the protein provides several options for crystallizing the fusion protein. In one embodiment, the fusion protein may be crystallized as a complex with the G-protein to which the GPCR couples. In another embodiment, the protein may be crystallized as a complex with an monovalent antibody that binds to the IC3 loop of the GPCR, as described in published US patent application US20090148510 and by Rasmusson et al (Nature 2007 450: 383-388), which publications are incorporated by reference for disclosure of those methods. In another embodiment, the third intracellular loop of the GPCR may contain another autonomously folding stable domain (which may be the same as or different to the autonomously folding stable domain at the N-terminal end of the protein) as described in Rosenbaum et al (Science 2007 318: 1266-73) and published U.S. patent application US20090118474, which publications are incorporated by reference for disclosure of those methods In very general terms, such a fusion protein may be made by substituting the N-terminal extracellular region of a GPCR with an autonomously folding stable protein that is globular and readily crystallizable, e.g., lysozyme, chitinase, glucose isomerase, xylanase, trypsin inhibitor, crambin or ribonuclease, for example. During crystallization, the autonomously folding stable domain is thought to provides a polar surface for crystal lattice contacts on the extracellular surface of the protein, thereby facilitating crystallization of the protein.

As will be described in greater detail below, the GPCR fusion protein may be produced using a nucleic acid encoding a longer protein that, in order from N- to C-terminus, contains a signal peptide, an epitope tag and a protease cleavage site and the GPCR fusion protein. The longer protein is produced in the cell. During secretion, the signal peptide is cleaved from the protein and the resulting protein can be purified using the epitope tag. The epitope tag can be cleaved from the GPCR fusion protein prior use. Various signal peptides, epitope tags and protease cleavage sites and methods for their use are known in the art.

GPCRs

Any known GPCR is suitable for use in the subject method. A disclosure of the sequences and phylogenetic relationships between 277 GPCRs is provided in Joost et al. (Genome Biol. 2002 3:RESEARCH0063, the entire contents of which is incorporated by reference) and, as such, at least 277 GPCRs are suitable for the subject methods. A more recent disclosure of the sequences and phylogenetic relationships between 367 human and 392 mouse GPCRs is provided in Vassilatis et al. (Proc Natl Acad Sci 2003 100:4903-8 and www.primalinc.com, each of which is hereby incorporated by reference in its entirely) and, as such, at least 367 human and at least 392 mouse GPCRs are suitable for the subject methods. GPCR families are also described in Fredriksson et al (Mol. Pharmacol. 2003 63, 1256-72).

The methods may be used, by way of exemplification, for purinergic receptors, vitamin receptors, lipid receptors, peptide hormone receptors, non-hormone peptide receptors, nonpeptide hormone receptors, polypeptide receptors, protease receptors, receptors for sensory signal mediator, and biogenic amine receptors not including β2-adrenergic receptor. In certain embodiments, said biogenic amine receptor does not include an adrenoreceptor. α-type adrenoreceptors (e.g. $\alpha_{1A}$, $\alpha_{1B}$ or $\alpha_{1C}$ adrenoreceptors), and β-type adrenoreceptors (e.g. $\beta_1$, $\beta_2$, or $\beta_3$ adrenoreceptors) are discussed in Singh et al., J. Cell Phys. 189:257-265, 2001.

It is recognized that both native (naturally occurring) and altered native (non-naturally occurring) GPCRs may be used in the subject methods. In certain embodiments, therefore, an altered native GPCR (e.g. a native GPCR that is altered by an amino acid substitution, deletion and/or insertion) such that it binds the same ligand as a corresponding native GPCR, and/or couples to a G-protein as a result of the binding. In certain cases, a GPCR employed herein may have an amino acid sequence that is at least 80% identical to, e.g., at least 90% identical, at least 85% identical, at least 90% identical, at least 95% identical, or at least 98% identical, to at least the heptahelical domain of a naturally occurring GPCR. A GPCR employed herein may optionally contain the C-terminal domain of a GPCR. In certain embodiments, a native GPCR may be "trimmed back" from its N-terminus and/or its C-terminus to leave its heptahelical domain, prior to use.

As such, the following GPCRs (native or altered) find particular use as parental GPCRs in the subject methods: cholinergic receptor, muscarinic 3; melanin-concentrating hormone receptor 2; cholinergic receptor, muscarinic 4; niacin receptor; histamine 4 receptor; ghrelin receptor; CXCR3 chemokine receptor; motilin receptor; 5-hydroxytryptamine (serotonin) receptor 2A; 5-hydroxytryptamine (serotonin) receptor 2B; 5-hydroxytryptamine (serotonin) receptor 2C; dopamine receptor D3; dopamine receptor D4; dopamine receptor D1; histamine receptor H2; histamine receptor H3; galanin receptor 1; neuropeptide Y receptor Y1; angiotensin II receptor 1; neurotensin receptor 1; melanocortin 4 receptor; glucagon-like peptide 1 receptor; adenosine A1 receptor; cannabinoid receptor 1; and melanin-concentrating hormone receptor 1.

In particular embodiments, the GPCR may belong to one of the following GPCR families: amine, peptide, glycoprotein hormone, opsin, olfactory, prostanoid, nucleotide-like, cannabinoid, platelet activating factor, gonadotropin-releasing hormone, thyrotropin-releasing hormone or melatonin families, as defined by Lapinsh et al (Classification of G-protein coupled receptors by alignment-independent extraction of principle chemical properties of primary amino acid sequences. Prot. Sci. 2002 11:795-805). The subject GPCR may be a family A GPCR (rhodopsin-like), family B GPCR (secretin-like, which includes the PTH and glucagon receptors), or a family C GPCR (glutamate receptor-like, which includes the GABA glutamate receptors), or an "other" family GPCR (which includes adhesion, frizzled, taste type-2, and unclassified family members).

Figure 2:
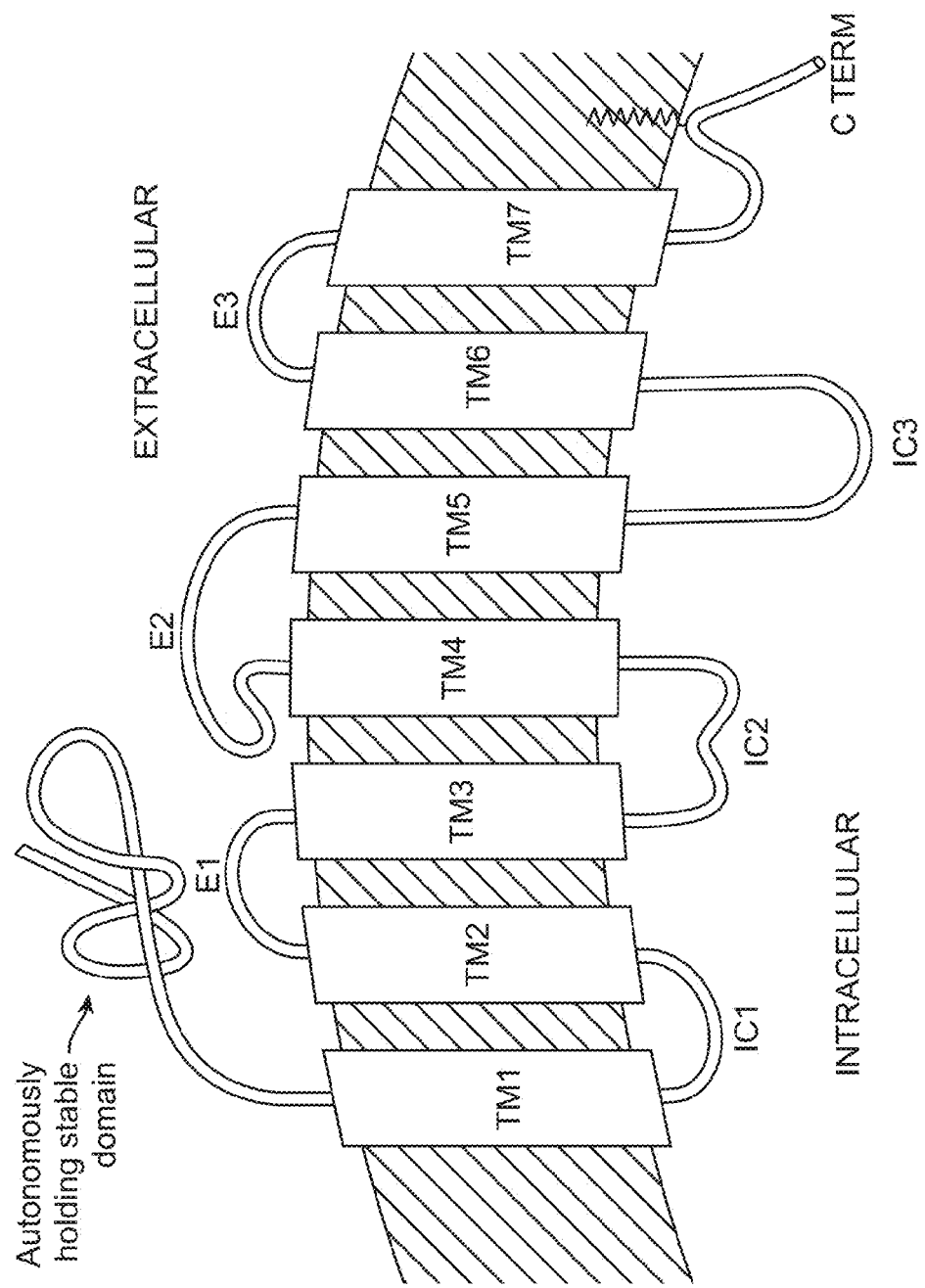
FIG. 2 is a schematic illustration of a subject fusion protein, showing an autonomously folding stable domain that is N-terminal to a GPCR.
Figure 3:
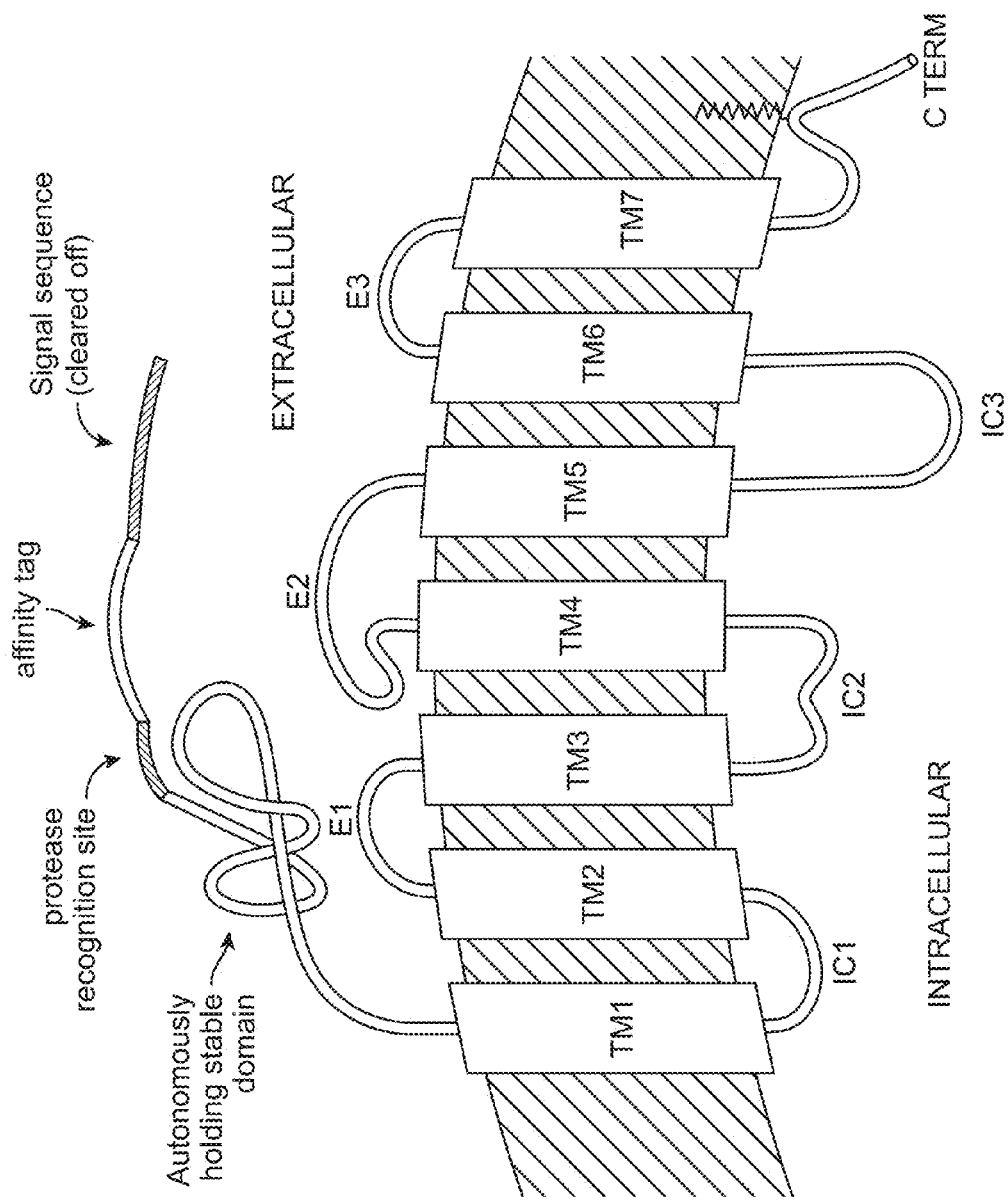
FIG. 3 is a schematic illustration of the fusion protein encoded by a subject nucleic acid. The encoded fusion protein contains an autonomously folding stable domain that is N-terminal to a GPCR. The protein further contains a signal sequence, an epitope tag and a protease cleavage site.

In the subject methods, the N-terminal extracellular region N-terminal to the TM1 region of a GPCR is usually identified, and replaced with an autonomously folding stable domain to produce a fusion protein. A schematic representation of the prototypical structure of a GPCR is provided in FIG. 1, where these regions, in the context of the entire structure of a GPCR, may be seen. A schematic representation of a subject fusion protein is shown in FIG. 2.

The N-terminal extracellular region is readily discernable by one of skill in the art using, for example, a program for identifying transmembrane regions: once transmembrane region TM1 is identified, the N-terminal extracellular region will be apparent. The N-terminal extracellular region may also be identified using such methods as pairwise or multiple sequence alignment (e.g. using the GAP or BESTFIT of the University of Wisconsin's GCG program, or CLUSTAL alignment programs, Higgins et al., Gene. 1988 73:237-44), using a target GPCR and, for example, GPCRs of known structure.

Suitable programs for identifying transmembrane regions include those described by Moller et al., (Bioinformatics, 17:646-653, 2001). A particularly suitable program is called "TMHMM" Krogh et al., (Journal of Molecular Biology, 305:567-580, 2001). To use these programs via a user interface, a sequence corresponding to a GPCR or a fragment thereof is entered into the user interface and the program run. Such programs are currently available over the world wide web, for example at the website of the Center for Biological Sequence Analysis at cbs.dtu.dk/services/. The output of these programs may be variable in terms its format, however they usually indicate transmembrane regions of a GPCR using amino acid coordinates of a GPCR.

When TM regions of a GPCR polypeptide are determined using TMHMM, the prototypical GPCR profile is usually obtained: an N-terminus that is extracellular, followed by a segment comprising seven TM regions, and further followed by a C-terminus that is intracellular. TM numbering for this prototypical GPCR profile begins with the most N-terminally disposed TM region (TM1) and concludes with the most C-terminally disposed TM region (TM7).

In certain cases, once the N-terminal extracellular region is identified in a GPCR, a suitable region of amino acids is chosen for substitution with the amino acid sequence of the autonomously folding stable domain. In certain embodiments, the C-terminus of the autonomously folding stable domain is linked to the amino acid that is within 50 residues (e.g., e.g., 1-5, 1-10, 1-20, 1-30, 1-40, etc. residues) N-terminal to the N-terminal amino acid of the TM 1 region of the GPCR, although linkages outside of this region are envisioned. In one exemplary embodiment, amino acids that are at the N-terminal end of the TM1 region (i.e., within what would be referred to as the TM1 region) may be replaced in addition the amino acids that are N-terminal to the TM region. In particular embodiments, this junction may be optimized to provide for maximal expression and receptor activity.

In addition to substituting N-terminal extracellular region of a GPCR with a autonomously folding stable domain, as described above, in certain cases, the intracellular C-terminal region of the GPCR (which may C-terminal to the cysteine palmitoylation site that is approximately 10 to 25 amino acid residues downstream of a conserved NPXXY motif), may be deleted. In certain cases, the 20-30 amino acids immediately C-terminal to the cysteine palmitoylation site are not deleted. In particular embodiments, this position may be optimized to provide for maximal expression and receptor activity.

Autonomously Folding Stable Domains

In particular embodiments, the autonomously folding stable domain is a polypeptide than can fold autonomously in a variety of cellular expression hosts, and is resistant to chemical and thermal denaturation. In particular embodiments, the autonomously folding stable domains may be derived from a protein that is known to be highly crystallizable in a variety of space groups and crystal packing arrangements. In certain cases, the stable, folded protein insertion may also shield the fusion protein from proteolysis, and may itself be protease resistant. Lysozyme is one such polypeptide, however many others are known.

In certain embodiments, a autonomously folding stable domain of a subject fusion protein may be a soluble, stable protein (e.g., a protein displaying resistance to thermal and chemical denaturation) that folds autonomously of the GPCR portion of the fusion protein, in a cell. In certain cases, the stable, autonomously folding stable domain may have no cysteine residues (or may be engineered to have no cysteine residues) in order to avoid potential disulphide bonds between the autonomously folding stable domain and a GPCR portion of the fusion protein, or internal disulphide bonds. Autonomously folding stable domains are conformationally restrained, and are resistant to protease cleavage.

In certain cases, the autonomously folding stable domain may contain most or all of the amino acid sequence of a polypeptide that is readily crystallized. Such proteins may be characterized by a large number of deposits in the protein data bank (www.rcsb.org) in a variety of space groups and crystal packing arrangements. While examples that employ lysozyme as stable, folded protein insertion are discussed below, the general principles may be used to employ any of a number of polypeptides that have the characteristics discussed above. Autonomously folding stable domain candidates include those containing the amino acid sequence of proteins that are readily crystallized including, but not limited to: lysozyme, chitinase, glucose isomerase, xylanase, trypsin inhibitor, crambin, ribonuclease. Other suitable polypeptides may be found at the BMCD database (Gilliland et al 1994. The Biological Macromolecule Crystallization Database, Version 3.0: New Features, Data, and the NASA Archive for Protein Crystal Growth Data. Acta Crystallogr. D50 408-413), as published to the world wide web.

In certain embodiments, the autonomously folding stable domain used may be at least 80% identical (e.g., at least 85% identical, at least 90% identical, at least 95% identical or at least 98% identical to a wild type protein. Many suitable wild type proteins, including non-naturally occurring variants thereof, are readily crystalizable.

In one embodiment, the autonomously folding stable domain may be of the lysozyme superfamily, which share a common structure and are readily crystallized. Such proteins are described in, e.g., Wohlkönig et al (Structural Relationships in the Lysozyme Superfamily: Significant Evidence for Glycoside Hydrolase Signature Motifs. PLoS ONE 2010 5: e15388).

As noted above, one such autonomously folding stable domain that may be employed in a subject fusion protein is lysozyme. Lysozyme is a highly crystallizable protein (see, e.g., Strynadka et al Lysozyme: a model enzyme in protein crystallography EXS 1996 75: 185-222) and at present over 200 atomic coordinates for various lysozymes, including many wild-type lysozymes and variants thereof, including lysozymes from phage T4, human, swan, rainbow trout, guinea fowl, soft-shelled turtle, tapes japonica, nurse shark, mouse sperm, dog and phage P1, as well as man-made variants thereof, have been deposited in NCBI's structure database. A subject fusion protein may contain any of a wide variety of lysozyme sequences. See, e.g., Strynadka et al (*Lysozyme: a model enzyme in protein crystallography* (EXS. 1996; 75:185-222), Evrard et al (*Crystal structure of the lysozyme from bacteriophage lambda and its relationship with V and C-type lysozymes*) J. Mol. Biol. 1998 276:151-64), Forsythe et al (*Crystallization of chicken egg-white lysozyme from ammonium sulfate*. Acta Crystallogr D Biol Crystallogr. 1997 53:795-7), Remington et al (*Structure of the Lysozyme from Bacteriophage T4: An Electron Density Map at 2.4A Resolution*), Lyne et al (*Preliminary crystallographic examination of a novel fungal lysozyme from Chalaropsis*. J Biol Chem. 1990 265:6928-30), Marana et al. (*Crystallization, data collection and phasing of two digestive lysozymes from Musca domestica*. Acta Crystallogr Sect F Struct Biol Cryst Commun. 2006 62:750-2), Harada et al (*Preliminary X-ray crystallographic study of lysozyme produced by Streptomyces globisporus*. J Mol Biol. 1989 207:851-2) and Yao et al (*Crystallization and preliminary X-ray structure analysis of pigeon egg-white lysozyme*). J. Biochem. 1992 111:1-3).

The length of the autonomously folding stable domain may be in the range of 50-500 amino acids, e.g., 80-200 amino acids in length, although autonomously folding stable domain having lengths outside of this range are also envisioned.

As noted above, the autonomously folding stable domain is not fluorescent or light-emitting. As such, the autonomously folding stable domain is not CFP, GFP, YFP, luciferase, or other light emitting, fluorescent variants thereof. In certain cases, a autonomously folding stable domain does not contain a flexible linker (e.g., a flexible polyglycine linker) or other such conformationally unrestrained regions. In certain cases, the autonomously folding stable domain contains a sequence of amino acids from a protein that has a crystal structure that has been solved. In certain cases, the stable, folded protein insertion should not have highly flexible loop region characterized by high cyrstallographic temperature factors (i.e., high B-factors).

An exemplary amino acid sequence for exemplary lysozyme fusion protein is set forth in FIG. 5, and the amino acid sequences of exemplary alternative additions (which may be substituted into any of the sequences of FIG. 5 in place of the lysozyme sequence) are shown in FIG. 4. These sequences include the sequences of trypsin inhibitor, calbindin, barnase, xylanase, glucokinase or a cytochrome, e.g., cytochrome a, b or c, although other sequences can be readily used. In particular embodiments, any of the proteins listed in table 1 of Papandreou et al (Eur. J. Biochem. 271, 4762-4768 (2004) FEBS 2004) or any of the 674 globular proteins listed by Wang and Yuan (Proteins 2000 38, 165-175) (which publications are incorporated by reference for disclosure of individual proteins), including orthologs from other species and variants proteins that are at least 80% identical to the listed proteins. Exemplary sequences include those of apolipophorin-III, staphylococcal nuclease, RNAse sa, uteroglobin, xylanase II, glutaredoxin, myohemerythin, bacillus 1-3, 1-4-β-glucanase, orotate phosphoribosyltransferase, cytochrome b562, serine esterase, fructose permease, subunit IIb, fibritin, legume lectin, chloramphenicol acetyltransferase, cytochrome c oxidase, adenovirus fibre, flavodoxin, phospholipase a2, stnv coat protein, signal transduction protein, lysin, pseudoazurin, cutinase, retinoid-x receptor α, transthyretin, dihydropteridin reductase, cytochrome c3, picornavirus, ch-p21 ras, interleukin-10, cellular retinoic-acid-binding protein, retroviral integrase, catalytic domain, oncomodulin, 2 (hiv-2) protease, glutamate receptor ligand binding core, calcium-binding protein, histidine-containing phosphocarrier, cellulase e2, parvalbumin, ubiquitin, triosephosphate isomerase, myoglobin, 2fe-2s ferredoxin, endonuclease, glycera globin, lysozyme, goose, uracil-dna glycosylase, lamprey globin, lysozyme, chicken, lumazine synthase, hemoglobin (horse), profilin, hypothetical protein ybea, hemoglobin (human), ribosomal protein, d-tyr trnatyr deacylase, erythrocruorin, integrase, coagulation factor x, leukemia inhibitory factor, glycosylasparaginase, carboxypeptidase inhibitor, mitochondrial cytochrome c, astacin, mhc class II p41 invariantchain fragment, cytochrome c2, diphtheria toxin, methylamine dehydrogenase, phospholipase, nadh oxidase, ovomucoid iii domain, dna-binding protein, signal transduction protein, ldl receptor, pheromone, ferredoxin ii, peptostreptococcus, anti-platelet protein, phosphatidylinositol 3-kinase, ferredoxin ii, desulfovibrio gigas, crambin, α-spectrin, sh3 domain, 1c0ba ribonuclease a, heat-stable enterotoxin b, signal transduction protein, c-src tyrosine kinase, tgf-β3, seed storage protein 7 s vicillin, prion protein domain, rubredoxin, clostridium pasteurianum, immunoglobulin, abrin a-chain, rubredoxin, archaeon pyrococcus furiosus, cd2, first domain, platelet factor 4, fasciculin, macromycin, chemokine (growth factor), plasminogen, cohesin-2 domain, (pro)cathepsin b, ectothiorhodospira vacuolata, glucose-specific factor iii, actinidin, hipip, allochromatium vinosum, staphylococcal nuclease, chymotrypsin inhibitor CI-2, collagen type VI, dna-binding protein, fk-506 binding, and factor IX.

The amino acid sequences of a variety of exemplary GPCR fusion proteins that can be employed herein are set forth in FIG. 6. Given these sequences, suitable fusion proteins could be designed using other GPCR.

Nucleic Acids

A nucleic acid comprising a nucleotide sequence encoding a subject fusion protein is also provided. A subject nucleic acid may be produced by any method. Since the genetic code and recombinant techniques for manipulating nucleic acid are known, the design and production of nucleic acids encoding a subject fusion protein is well within the skill of an artisan. In certain embodiments, standard recombinant DNA technology (Ausubel, et al, Short Protocols in Molecular Biology, 3rd ed., Wiley & Sons, 1995; Sambrook, et al., Molecular Cloning: A Laboratory Manual, Second Edition, (1989) Cold Spring Harbor, N.Y.) methods are used.

For example, site directed mutagenesis and subcloning may be used to introduce/delete/substitute nucleic acid residues in a polynucleotide encoding GPCR. In other embodiments, PCR may be used. Nucleic acids encoding a polypeptide of interest may also be made by chemical synthesis entirely from oligonucleotides (e.g., Cello et al., Science (2002) 297:1016-8).

In certain embodiments, the codons of the nucleic acids encoding polypeptides of interest are optimized for expression in cells of a particular species, particularly a mammalian, e.g., human, species. Vectors comprising a subject nucleic acid are also provided. A vector may contain a subject nucleic acid, operably linked to a promoter.

A host cell (e.g., a host bacterial, mammalian, insect, plant or yeast cell) comprising a subject nucleic acid is also provided as well a culture of subject cells. The culture of cells may contain growth medium, as well as a population of the cells. The cells may be employed to make the subject fusion protein in a method that includes culturing the cells to provide for production of the fusion protein. In many embodiments, the fusion protein is directed to the plasma membrane of the cell, and is folded into its active form by the cell.

The native form of a subject fusion protein may be isolated from a subject cell by conventional technology, e.g., by precipitation, centrifugation, affinity, filtration or any other method known in the art. For example, affinity chromatography (Tilbeurgh et al., (1984) FEBS Lett. 16:215); ion-exchange chromatographic methods (Goyal et al., (1991) Biores. Technol. 36:37; Fliess et al., (1983) Eur. J. Appl. Microbiol. Biotechnol. 17:314; Bhikhabhai et al., (1984) J. Appl. Biochem. 6:336; and Ellouz et al., (1987) Chromatography 396:307), including ion-exchange using materials with high resolution power (Medve et al., (1998) J. Chromatography A 808:153; hydrophobic interaction chromatography (Tomaz and Queiroz, (1999) J. Chromatography A 865:123; two-phase partitioning (Brumbauer, et al., (1999) Bioseparation 7:287); ethanol precipitation; reverse phase HPLC; chromatography on silica or on a cation-exchange resin such as DEAE; chromatofocusing; SDS-PAGE; ammonium sulfate precipitation; or size exclusion chromatography using, e.g., Sephadex G-75, may be employed.

In particular embodiments, the GPCR, e.g., the N- or C-terminus of the GPCR or an external loop of the GPCR, may be tagged with an affinity moiety, e.g., a his tag, GST, MBP, flag tag, or other antibody binding site, in order to facilitate purification of the GPCR fusion protein by affinity methods. Before crystallization, a subject fusion protein may be assayed to determine if the fusion protein is active, e.g., can bind ligand and change in conformation upon ligand binding, and if the fusion protein is resistant to protease cleavage. Such assays are well known in the art.

In particular embodiments and illustrated in FIG. 3, the protein encoded by the nucleic acid contains, from N-terminus to C-terminus: a) a signal sequence; b) an affinity, e.g., epitope, tag; c) a protease cleavage site; d) an autonomously folding stable domain; and e) a GPCR. During secretion, the signal peptide is cleaved from the protein and the resulting protein can be purified using the affinity tag. The affinity tag can be cleaved from the GPCR fusion protein prior use.

Crystallization Methods

Prior to crystallization, the isolated fusion protein may optionally be combined with a variety of moieties (e.g., an antibody (see, e.g., US20090148510, Rasmusson et al Nature 2007 450: 383-388 and Day et al Nature Methods 2007 4:927-9), a modulator (such as an agonist, an antagonist, a native ligand, etc., as described in, e.g., Rosenbaum Science. 2007 318:1266-73 etc), another GPCR, the G protein to which the GPCR couples or another protein, e.g., Gs, Gi, or Gq), that bind to the GPCR, to produce a complex. The complex is then crystallized and the atomic coordinates of the complex can be obtained.

A subject fusion protein may be crystallized using any of a variety of crystallization methods, many of which are reviewed in Caffrey Membrane protein crystallization. J Struct. Biol. 2003 142:108-32, including those that employ detergent micelles, bicelles and lipidic cubic phase (LCP). In general terms, the methods are lipid-based methods that include adding lipid to the fusion protein prior to crystallization. Such methods have previously been used to crystallize other membrane proteins. Many of these methods, including the lipidic cubic phase crystallization method and the bicelle crystallization method, exploit the spontaneous self-assembling properties of lipids and detergent as vesicles (vesicle-fusion method), discoidal micelles (bicelle method), and liquid crystals or mesophases (in meso or cubic-phase method). Lipidic cubic phases crystallization methods are described in, for example: Landau et al, *Lipidic cubic phases: a novel concept for the crystallization of membrane proteins*. Proc. Natl. Acad. Sci. 1996 93:14532-5; Gouaux, It's not just a phase: crystallization and X-ray structure determination of bacteriorhodopsin in lipidic cubic phases. Structure. 1998 6:5-10; Rummel et al, *Lipidic Cubic Phases: New Matrices for the Three-Dimensional Crystallization of Membrane Proteins*. J. Struct. Biol. 1998 121:82-91; and Nollert et al *Lipidic cubic phases as matrices for membrane protein crystallization* Methods. 2004 34:348-53, which publications are incorporated by reference for disclosure of those methods. Bicelle crystallization methods are described in, for example: Faham et al *Crystallization of bacteriorhodopsin from bicelle formulations at room temperature*. Protein Sci. 2005 14:836-40. 2005 and Faham et al, *Bicelle crystallization: a new method for crystallizing membrane proteins yields a monomeric bacteriorhodopsin structure*. J Mol Biol. 2002 Feb. 8; 316(1):1-6, which publications are incorporated by reference for disclosure of those methods.

Computer Models and Computer Systems

In certain embodiments, the above-described computer readable medium may further comprise programming for displaying a molecular model of a GPCR or a complex of the same crystallized by the instant method, programming for identifying a compound that binds to the GPCR and/or a database of structures of known test compounds, for example. A computer system comprising the computer-readable medium is also provided. The model may be displayed to a user via a display, e.g., a computer monitor, for example.

The atomic coordinates may be employed in conjunction with a modeling program to provide a model of the a GPCR or a complex of the same. As used herein, the term "model" refers to a representation in a tangible medium of the three dimensional structure of the a GPCR or a complex of the same. For example, a model can be a representation of the three dimensional structure in an electronic file, on a display, e.g., a computer screen, on a piece of paper (i.e., on a two dimensional medium), and/or as a ball-and-stick figure. Physical three-dimensional models are tangible and include, but are not limited to, stick models and space-filling models. The phrase "imaging the model on a computer screen" refers to the ability to express (or represent) and manipulate the model on a computer screen using appropriate computer hardware and software technology known to those skilled in the art. Such technology is available from a variety of sources including, for example, Evans and Sutherland, Salt Lake City, Utah, and Biosym Technologies, San Diego, Calif. The phrase "providing a picture of the model" refers to the ability to generate a "hard copy" of the model. Hard copies include both motion and still pictures. Computer screen images and pictures of the model can be visualized in a number of formats including space-filling representations, backbone traces, ribbon diagrams, and electron density maps. Exemplary modeling programs include, but are not limited to PYMOL, GRASP, or O software, for example.

In another embodiment, the invention provides a computer system having a memory comprising the above-described atomic coordinates; and a processor in communication with the memory, wherein the processor generates a molecular model having a three dimensional structure representative of a GPCR or a complex of the same. The processor can be adapted for identifying a candidate compound having a structure that is capable of binding to the a GPCR or a complex of the same, for example.

In the present disclosure, the processor may execute a modeling program which accesses data representative of the GPCR structure. In addition, the processor also can execute another program, a compound modeling program, which uses the three-dimensional model of the GPCR or a complex of the same to identify compounds having a chemical structure that binds to the GPCR or a complex of the same. In one embodiment the compound identification program and the structure modeling program are the same program. In another embodiment, the compound identification program and the structure modeling program are different programs, which programs may be stored on the same or different storage medium.

A number of exemplary public and commercial sources of libraries of compound structures are available, for example the Cambridge Structural Database (CSD), the Chemical Directory (ACD) from the company MDL (US), ZINC (Irwin and Shoichet, J. Chem. Inf Model. (2005) 45:177-82) as well as various electronic catalogues of publicly available compounds such as the National Cancer Institute (NCI, US) catalogue, ComGenex catalogue (Budapest, Hungary), and Asinex (Moscow, Russia). Such libraries may be used to allow computer-based docking of many compounds in order to identify those with potential to interact with the GPCR using the atomic coordinates described herein.

In certain cases, the method may further comprise a testing a compound to determine if it binds and/or modulates the GPCR or a complex of the same, using the atomic coordinates provided herein. In some embodiments, the method may further comprise obtaining the compound (e.g., purchasing or synthesizing the compound) and testing the compound to determine if it modulates (e.g., activates or inhibits) the GPCR, e.g., acts an agonist, antagonist or inverse agonist of the GPCR).

In some embodiments, the method employs a docking program that computationally tests known compounds for binding to the GPCR or complex of the same. Structural databases of known compounds are known in the art. In certain cases, compounds that are known to bind and modulate the GPCR or complex of the same may be computationally tested for binding to GPCR or complex of the same, e.g., in order to identify a binding site and/or facilitate the identification of active variants of an existing compound. Such compounds include compounds that are known to be agonists of the GPCR. In other cases, the method may include designing a compound that binds to the GPCR, either de novo, or by modifying an existing compound that is known to bind to the GPCR.

A method that comprises receiving a set of atomic coordinates for the GPCR or complex of the same; and identifying a compound that binds to said GPCR or complex of the same using the coordinates is also provided, as is a method comprising: forwarding to a remote location a set of atomic coordinates for the GPCR or complex of the same; and receiving the identity of a compound that binds to the GPCR or complex of the same.

In certain embodiments, a computer system comprising a memory comprising the atomic coordinates of a GPCR or complex of the same is provided. The atomic coordinates are useful as models for rationally identifying compounds that bind to the GPCR or complex of the same. Such compounds may be designed either de novo, or by modification of a known compound, for example. In other cases, binding compounds may be identified by testing known compounds to determine if the "dock" with a molecular model of the GPCR. Such docking methods are generally well known in the art.

The structure data provided can be used in conjunction with computer-modeling techniques to develop models of ligand-binding sites on the GPCR or complex of the same selected by analysis of the crystal structure data. The site models characterize the three-dimensional topography of site surface, as well as factors including van der Waals contacts, electrostatic interactions, and hydrogen-bonding opportunities. Computer simulation techniques are then used to map interaction positions for functional groups including but not limited to protons, hydroxyl groups, amine groups, divalent cations, aromatic and aliphatic functional groups, amide groups, alcohol groups, etc. that are designed to interact with the model site. These groups may be designed into a candidate compound with the expectation that the candidate compound will specifically bind to the site.

The ability of a candidate compound to bind to a GPCR can be analyzed prior to actual synthesis using computer modeling techniques. Only those candidates that are indicated by computer modeling to bind the target with sufficient binding energy (i.e., binding energy corresponding to a dissociation constant with the target on the order of $10^{-2}$ M or tighter) may be synthesized and tested for their ability to bind to and modulate the GPCR. Such assays are known to those of skill in the art. The computational evaluation step thus avoids the unnecessary synthesis of compounds that are unlikely to bind the GPCR with adequate affinity.

A candidate compound may be computationally identified by means of a series of steps in which chemical entities or fragments are screened and selected for their ability to associate with individual binding target sites on the GPCR. One skilled in the art may use one of several methods to screen chemical entities or fragments for their ability to associate with the GPCR, and more particularly with target sites on the GPCR. The process may begin by visual inspection of, for example a target site on a computer screen, based on the coordinates, or a subset of those coordinates. Selected fragments or chemical entities may then be positioned in a variety of orientations or "docked" within a target site of the GPCR as defined from analysis of the crystal structure data. Docking may be accomplished using software such as Quanta (Molecular Simulations, Inc., San Diego, Calif.) and Sybyl (Tripos, Inc. St. Louis, Mo.) followed by energy minimization and molecular dynamics with standard molecular mechanics forcefields such as CHARMM (Molecular Simulations, Inc., San Diego, Calif.) and AMBER (University of California at San Francisco).

Specialized computer programs may also assist in the process of selecting fragments or chemical entities. These include but are not limited to: GRID (Goodford, P. J., "A Computational Procedure for Determining Energetically Favorable Binding Sites on Biologically Important Macromolecules," J. Med. Chem., 28, pp. 849-857 (1985)); GRID is available from Oxford University, Oxford, UK; MCSS (Miranker, A. and M. Karplus, "Functionality Maps of Binding Sites: A Multiple Copy Simultaneous Search Method," Proteins: Structure, Function and Genetics, 11, pp. 29-34 (1991)); MCSS is available from Molecular Simulations, Inc., San Diego, Calif.; AUTODOCK (Goodsell, D. S. and A. J. Olsen, "Automated Docking of Substrates to Proteins by Simulated Annealing," Proteins: Structure, Function, and Genetics, 8, pp. 195-202 (1990)); AUTODOCK is available from Scripps Research Institute, La Jolla, Calif.; DOCK (Kunts, I. D., et al. "A Geometric Approach to Macromolecule-Ligand Interactions," J. Mol. Biol., 161, pp. 269-288 (1982)); DOCK is available from University of California, San Francisco, Calif.; CERIUS II (available from Molecular Simulations, Inc., San Diego, Calif.); and Flexx (Raret, et al. J. Mol. Biol. 261, pp. 470-489 (1996)).

Also provided is a method of determining a crystal structure. This method may comprise receiving an above described fusion protein, crystallizing the fusion protein to produce a crystal; and obtaining atomic coordinates of the fusion protein from the crystal. The fusion protein may be received from a remote location (e.g., a different laboratory in the same building or campus, or from a different campus or city), and, in certain embodiments, the method may also comprise transmitting the atomic coordinates, e.g., by mail, e-mail or using the internet, to the remote location or to a third party.

In other embodiments, the method may comprise forwarding a fusion protein to a remote location where the protein may be crystallized and analyzed, and receiving the atomic coordinates of the fusion protein.

In some embodiments a method for displaying the three dimensional structure of a GPCR on a computer system is provided. This method may comprise: a) accessing a file containing atomic coordinates of a GPCR using a computer system that comprises a modeling program, wherein the atomic coordinates are produced by subjecting crystals of a GPCR fusion protein to X-ray diffraction analysis, wherein the GPCR fusion protein is described above, b) modeling the atomic coordinates on the computer system using the modeling program to produce a model of the three dimensional structure of at least a portion of the GPCR by; and c) displaying the model of the three dimensional structure on the computer system. The crystals also contain a ligand for the GPCR, and the method further comprises identifying the binding site for the ligand in the GPCR using the model. This method may further comprises identifying the amino acids in the binding site. This method may further comprise determining whether a test compound docks with the binding site using the model. This method may further comprise analyzing the packing between the test compound and surrounding amino acids in said binding site. In some embodiments, the analyzing may comprise calculating polar contacts between the ligand and the model.

In particular embodiments, a method for analyzing the three dimensional structure of a GPCR on a computer system is provided. This method may involve: a) accessing a file containing atomic coordinates of a GPCR using a computer system that comprises a modeling program, wherein the atomic coordinates are produced by subjecting crystals of a GPCR fusion protein to X-ray diffraction analysis, wherein the GPCR fusion protein is described above, b) modeling the atomic coordinates on the computer system using the modeling program to produce a model of the three dimensional structure of at least a portion of the GPCR.; and c) displaying the model of the three dimensional structure on the computer system. In certain cases, the crystals contain a ligand for the GPCR (e.g., a known inhibitor, natural ligand or agonist, etc.), and the method further comprises identifying the binding site for the ligand in the GPCR using the model. The analyzing step may comprise identifying amino acids that form polar contacts between the ligand and amino acids in the binding site, using the model. This method may further comprise determining whether a test compound, e.g., a candidate pharmaceutical, docks with the binding site using the model. The method may comprise analyzing the packing of the test compound and amino acids in the binding site, using the model. This method may further comprise making the modulator and testing it on the GPCR in the presence of a ligand for the GPCR.

In order to further illustrate the present invention, the following specific examples are given with the understanding that they are being offered to illustrate the present invention and should not be construed in any way as limiting its scope.

Materials, Methods and Results I

Molecular Biology for the Generation of N-T4L Fused β2AR Construct FLAAT

The previously generated construct $\beta_2$AR365 was used as the template for further modification to generate the N-T4L fused $\beta_2$AR construct FLAAT. In this $\beta_2$AR365 template construct, the coding sequence of human $\beta_2$AR encompassing Gly2 to Gly365 was cloned into the pFastbac1 Sf9 expression vector (Invitrogen). The HA signal peptide followed by FLAG epitope tag and tobacco etch virus (TEV) protease recognition sequence was directly added to the N-terminus of the receptor for expression and purification purpose. A point mutation of N187E was also introduced to the construct to disrupt this unwanted glycosylation site.

The DNA cassette encoding the full length T4L lysozyme (WT*, C54T, C97A) with 2 additional alanines attached at the C-terminus was made and amplified by PCR using previously described construct $\beta_2$AR-T4L (Rasmussen et al. Crystal structure of the human beta2 adrenergic G-protein-coupled receptor. Nature. 2007 450:383 and Cherezov et al High-resolution crystal structure of an engineered human beta2-adrenergic G protein-coupled receptor. Science. 2007 318: 1258-65) as the template and synthetic oligonucleotides as primers. This cassette was inserted into the $\beta_2$AR365 construct between the end of the TEV protease recognition sequence and Asp29 of the receptor by using the Quickchange multi protocol (Stratagene). Two point mutations M96T, M98T were also introduced into the construct based on the Quickchange multi protocol using synthetic oligonucleotides as mutation primers. The protein sequence of the entire fusion FLAAT is shown in FIG. 5.

The entire FLAAT gene described above was further cloned into the Best-Bac Sf9 expression vector pv11393 (expressionsystems) using the restriction enzyme digestion site XbaI and EcoRI. The final construct was confirmed by NDA sequencing.

Expression and Purification of FLAAT from Baculovirus-Infected Sf9 Cells

Recombinant baculovirus was made from pv11393-FLAAT using Best-Bac expression system, as described by the system protocol (expressionsystem). FLAAT was expressed by Sf9 cells that were infected by this baculovirus with 1:50 dilution at the cell density of 4 million/ml. 1 µM of receptor antagonist alprenolol was included to enhance the receptor stability and yield. The infected cells were harvested after 48 hs of incubation at 27° C.

The harvested cells were lysed by vigorous stifling in 10 times volume of lysis buffer (10 mM TRIS-Cl pH 7.5, 2 mM EDTA) complemented with protease inhibitor Leupeptin (2.5 µg/ml final concentration, Sigma) and Benzamindine (160 µg/ml final concentration, Sigma) for 15 minutes. The FLAAT protein was extracted from the cell membrane by thorough homogenization using solubilization buffer (100 mM NaCl, 20 mM TRIS-Cl, pH 7.5, 1% Dodecylmaltoside) complemented with Leupeptin and Benzamindine (2.5 µg/ml and 160 µg/ml final concentration, respectively). 10 ml of solubilization buffer was used for each gram of cell pellet. The Dodecylmaltoside (DDM)-solubilized FLAAT bearing the FLAG epitope was then purified by M1 antibody affinity chromatography (Sigma). Extensive washing using HLS buffer (100 mM NaCl, 20 mM HEPES pH 7.5, 0.1% DDM) was performed to get rid of alprenolol. The protein was then eluted with HLS buffer complemented with 5 mM EDTA, 200 µg free FLAG peptide and saturating concentration of cholesterol hemisuccinate.

The eluted FLAAT was further purified by affinity chromatography using Sepharose attached with Alprenolol as previously described (Cherezov et al High-resolution crystal structure of an engineered human beta2-adrenergic G protein-coupled receptor. Science 2007 318:1258-65) in order to selectively isolate functional FLAAT from non-functional protein. HHS buffer (350 mM NaCl, 20 mM HEPES pH 7.5, 0.1% DDM) complemented with 300 µM alprenolol and saturating concentration of cholesterol hemisuccinate was used to elute the protein. The eluted FLAAT bound with Alprenolol was then re-applied to M1 resin, allowing either washing off Alprenolol or exchanging Alprenolol with different ligand (for example, full agonist BI167107). Unliganded FLAAT or FLAAT bound with BI167107 was then eluted from M1 resin with HLS buffer complemented with 5 mM EDTA, 200 mg/ml free FLAG peptide and saturating concentration of cholesterol hemisuccinate. The FLAG epitope tag of FLAAT was removed by the treatment of tobacco etch virus (TEV) protease (invitrogen) for 3 hs at room temperature or overnight at 4° C. The purity of the final FLAAT is more than 90% according to the result of SDS-PAGE electrophoresis.

Crystallization of the FLAAT-BI167107-NB80 Ternary Complex

Nanobody80 (NB80) was expressed and purified as previously described (Rasmussen Structure of a nanobody-stabilized active state of the β(2) adrenoceptor. Nature. 2011 469: 175-80.). The untagged FLAAT bound with high affinity agonist BI167107 was purified as described above. The purified FLAAT-BI167107 and NB80 was mixed with a 1:2 molar ratio. The FLAAT-BI167107-NB80 ternary complex was then isolated from free NB80 by size exclusion chromatography (SEC) using sephacryl S-200 column (GE health care life sciences) equilibrated in 100 mM NaCl, 10 mM HEPES pH 7.5, 0.1% DDM and 10 µM BI167107. The same buffer was used as the running buffer for SEC.

The FLAAT-BI167107-NB80 complex after SEC was concentrated to a final concentration of 60 mg/ml using vivaspin concentrator (Sartorius-Stedim). The complex was crystallized using lipid cubic phase (LCP) method as previously described (Rosenbaum et al, GPCR engineering yields high-resolution structural insights into beta2-adrenergic receptor function. Science. 2007 318: 1266-73.). The protein complex was firstly mixed with lipid moloolein with a 1:1.5 mass ratio in room temperature. 0.1 µl of the protein-lipid mixture drop was put in each well of a 24-well glass sandwich plate. The drop was then overlaid with 0.80 of precipitant and the well was sealed by glass coverslip. By using this method, the FLAAT-BI167107-NB80 ternary complex was crystallized in 31%-35% PEG400 (v/v) and 0.1M Tris-Cl, pH8.0 after 4 days of incubation in 20° C.

Materials and Methods II

Expression and Purification of β2AR, Gs Heterotrimer, and Nanobody-35

Figure 16:
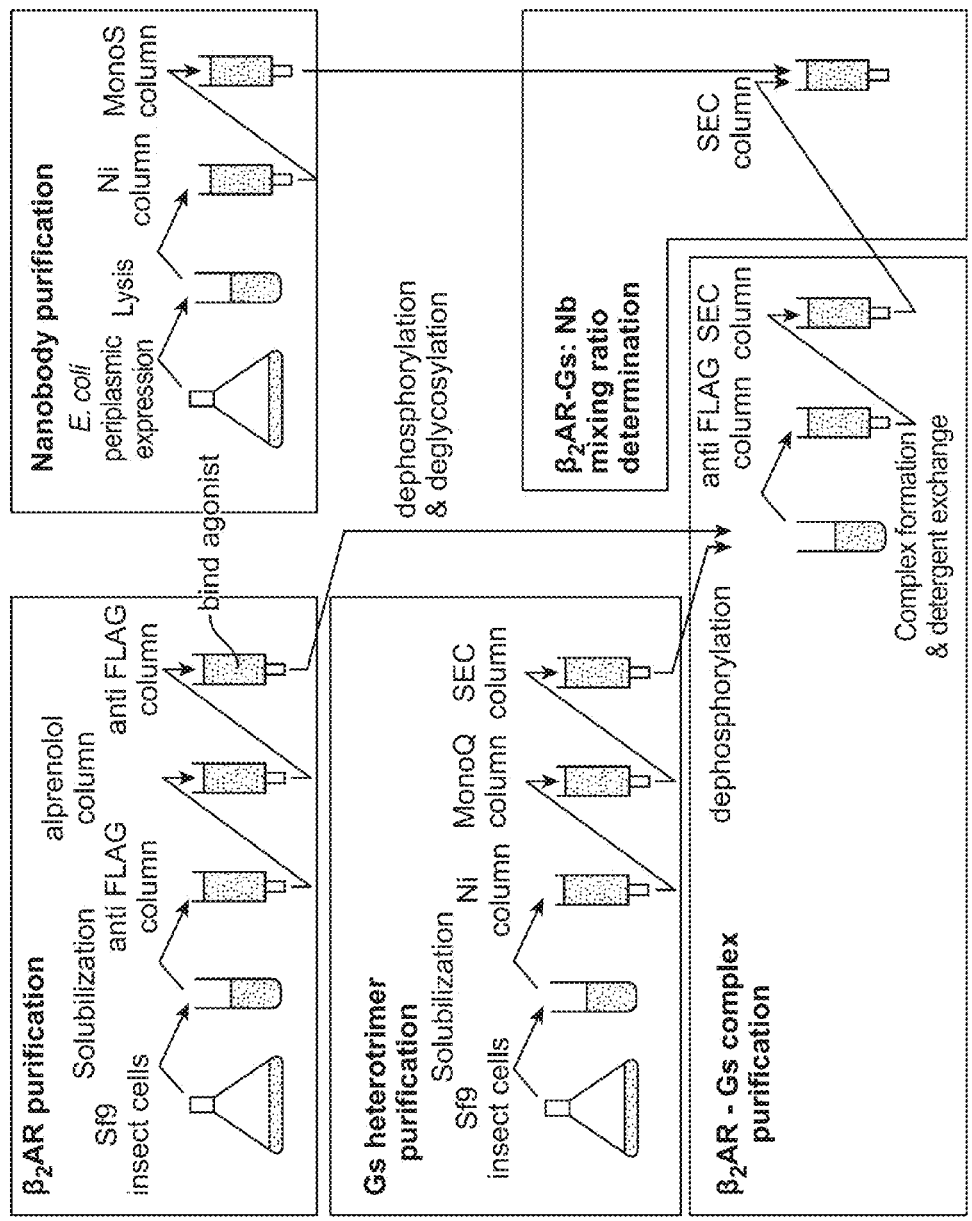
FIG. 16. Flow-chart of the purification procedures for preparing R:G complex with Nb35

An N-terminally fused T4 lysozyme-β2AR construct β2AR truncated in position 365 (T4L-β2AR, described in detail below) was expressed in Sf9 insect cell cultures infected with recombinant baculovirus (BestBac, Expression Systems), and solubilized in n-Dodecyl-β-D-maltoside (DDM) according to methods described previously Kobilka (Amino and carboxyl terminal modifications to facilitate the production and purification of a G protein-coupled receptor. Anal Biochem 1995 231, 269-271; see FIG. 16 for purification overview). A β2AR construct truncated after residue 365 (β2AR-365) was used for the majority of the analytical experiments and for deuterium exchange experiments. M1 Flag affinity chromatography (Sigma) served as the initial purification step followed by alprenolol-Sepharose chromatography for selection of functional receptor. A subsequent M1 Flag affinity chromatography step was used to exchange receptor-bound alprenolol for high-affinity agonist BI-167107. The agonist-bound receptor was eluted, dialyzed against buffer (20 mM HEPES, pH 7.5, 100 mM NaCl, 0.1% DDM and 10 µM BI-167107), treated with lambda phosphatase (New England Biolabs), and concentrated to approximately 50 mg ml$^{-1}$ with a 50 kDa molecular weight cut off (MWCO) Millipore concentrator. Prior to spin concentration, the β2AR-365 construct, but not T4L-β2AR, was treated with PNGaseF (New England Biolabs) to remove amino-terminal N-linked glycosylation. The purified receptor was routinely analyzed by SDS-PAGE/Coomassie brilliant blue staining (see FIG. 17a).

Bovine Gαs short, His6-bovine Gβ1, and bovine Gγ2 were expressed in HighFive insect cells (Invitrogen) grown in Insect Xpress serum-free media (Lonza). Cultures were grown to a density of 1.5 million cells per ml and then infected with three separate *Autographa californica* nuclear polyhedrosis virus each containing the gene for one of the G protein subunits at a 1:1 multiplicity of infection (the viruses were a generous gift from Dr. Alfred Gilman). After 40-48 hours of incubation the infected cells were harvested by centrifugation and resuspended in 75 ml lysis buffer (50 mM HEPES, pH 8.0, 65 mM NaCl, 1.1 mM MgCl$_2$, 1 mM EDTA, 1×PTT (35 µg/ml phenylmethanesulfonyl fluoride, 32 µg/ml tosyl phenylalanyl chloromethyl ketone, 32 µg/ml tosyl lysyl chloromethyl ketone), 1× LS (3.2 µg/ml leupeptin and 3.2 µg/ml soybean trypsin inhibitor), 5 mM β-mercaptoethanol (β-ME), and 10 µM GDP) per liter of culture volume. The suspension was pressurized with 600 psi N$_2$ for 40 minutes in a nitrogen cavitation bomb (Parr Instrument Company). After depressurization, the lysate was centrifuged to remove nuclei and unlysed cells, and then ultracentrifuged at 180,000×g for 40 minutes. The pelleted membranes were resuspended in 30 ml wash buffer (50 mM HEPES, pH 8.0, 50 mM NaCl, 100 µM MgCl$_2$, 1×PTT, 1× LS, 5 mM β-ME, 10 µM GDP) per liter culture volume using a Dounce homogenizer and centrifuged again at 180,000×g for 40 minutes. The washed pellet was resuspended in a minimal volume of wash buffer and flash frozen with liquid nitrogen.

The frozen membranes were thawed and diluted to a total protein concentration of 5 mg/ml with fresh wash buffer. Sodium cholate detergent was added to the suspension at a final concentration of 1.0%, MgCl$_2$ was added to a final concentration of 5 mM, and 0.05 mg of purified protein phosphatase 5 (prepared in house) was added per liter of culture volume. The sample was stirred on ice for 40 minutes, and then centrifuged at 180,000×g for 40 minutes to remove insoluble debris. The supernatant was diluted 5-fold with Ni-NTA load buffer (20 mM HEPES, pH 8.0, 363 mM NaCl, 1.25 mM MgCl$_2$, 6.25 mM imidazole, 0.2% Anzergent 3-12, 1×PTT, 1× LS, 5 mM β-ME, 10 µM GDP), taking care to add the buffer slowly to avoid dropping the cholate concentration below its critical micelle concentration too quickly. 3 ml of Ni-NTA resin (Qiagen) pre-equlibrated in Ni-NTA wash buffer 1 (20 mM HEPES, pH 8.0, 300 mM NaCl, 2 mM MgCl$_2$, 5 mM imidazole, 0.2% Cholate, 0.15% Anzergent 3-12, 1×PTT, 1×LS, 5 mM β-ME, 10 µM GDP) per liter culture volume was added and the sample was stirred on ice for 20 minutes. The resin was collected into a gravity column and washed with 4× column volumes of Ni-NTA wash buffer 1, Ni-NTA wash buffer 2 (20 mM HEPES, pH 8.0, 50 mM NaCl, 1 mM MgCl$_2$, 10 mM imidazole, 0.15% Anzergent 3-12, 0.1% DDM, 1×PTT, 1× LS, 5 mM β-ME, 10 µM GDP), and Ni-NTA wash buffer 3 (20 mM HEPES, pH 8.0, 50 mM NaCl, 1 mM MgCl$_2$, 5 mM imidazole, 0.1% DDM, 1×PTT, 1× LS, 5 mM β-ME, 10 µM GDP). The protein was eluted with Ni-NTA elution buffer (20 mM HEPES, pH 8.0, 40 mM NaCl, 1 mM MgCl2, 200 mM imidazole, 0.1% DDM, 1×PTT, 1× LS, 5 mM β-ME, 10 µM GDP). Protein-containing fractions were pooled and MnCl$_2$ was added to a final concentration of 100 µM. Fifty µg of purified lambda protein phosphatase (prepared in house) was added per liter of culture volume and the elute was incubated on ice with stifling for 30 minutes. The eluate was passed through a 0.22 µm filter and loaded directly onto a MonoQ HR 16/10 column (GE Healthcare) equilibrated in MonoQ buffer A (20 mM HEPES, pH 8.0, 50 mM NaCl, 100 µM MgCl$_2$, 0.1% DDM, 5 mM β-ME, 1×PTT). The column was washed with 150 ml buffer A at 5 ml/min and bound proteins were eluted over 350 ml with a linear gradient up to 28% MonoQ buffer B (same as buffer A except with 1 M NaCl). Fractions were collected in tubes spotted with enough GDP to make a final concentration of 10 µM. The Gs containing fractions were concentrated to 2 ml using a stirred ultrafiltration cell (Amicon) with a 10 kDa NMWL regenerated cellulose membrane (Millipore). The concentrated sample was run on a Superdex 200 prep grade XK 16/70 column (GE Healthcare) equilibrated in 5200 buffer (20 mM HEPES, pH 8.0, 100 mM NaCl, 1.1 mM MgCl$_2$, 1 mM EDTA, 0.012% DDM, 100 µM TCEP, 2 µM GDP). The fractions containing pure Gs were pooled, glycerol was added to 10% final concentration, and then the protein was concentrated to at least 10 mg/ml using a 30 kDa MWCO centrifugal ultrafiltration device (Millipore). The concentrated sample was then aliquoted, flash frozen, and stored at −80°. A typical yield of final, purified Gs heterotrimer from 8 liters of cell culture volume was 6 mg.

Figure 18:
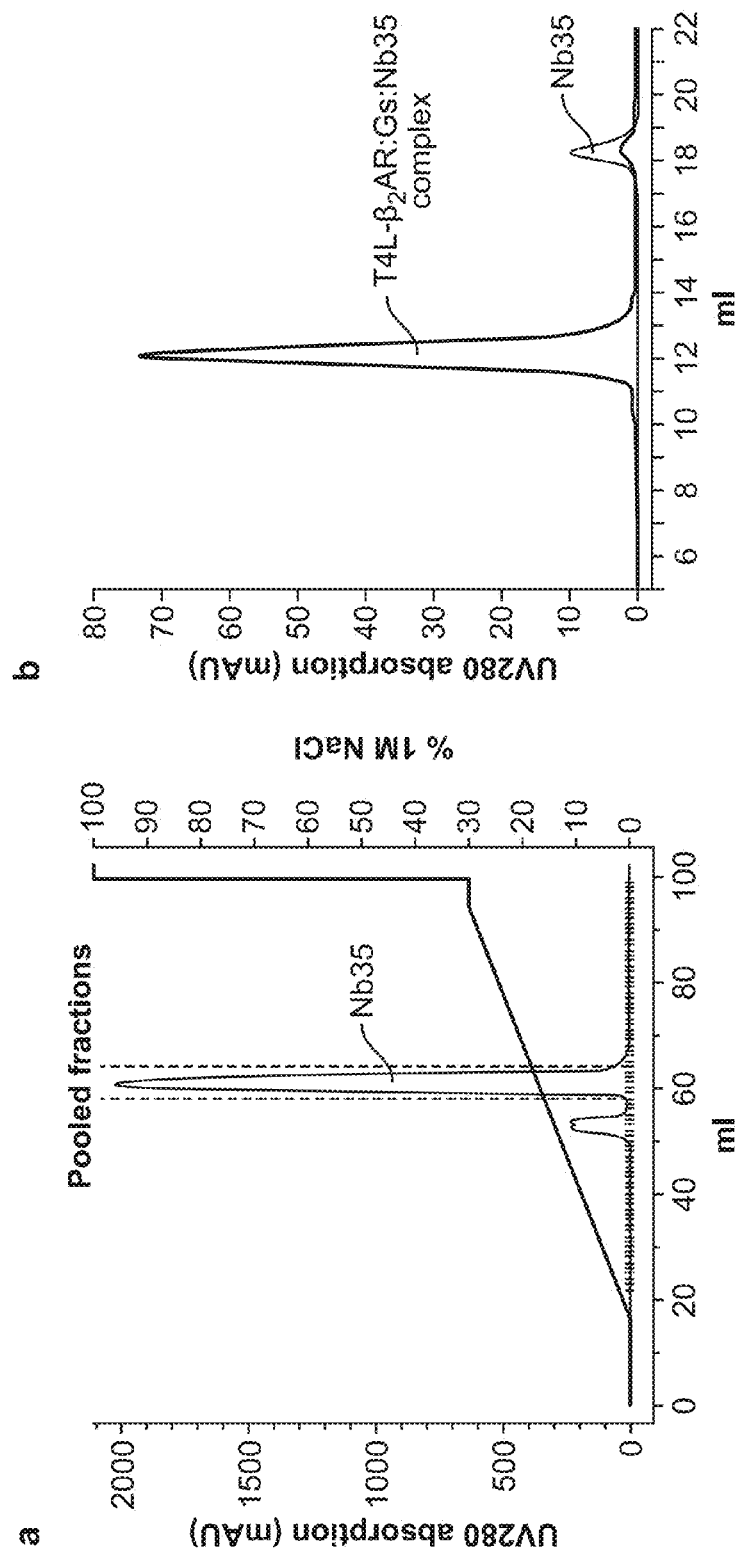
FIG. 18. Purification of Nb35 and determination of R:G:Nb mixing ratios a) Preparative ion exchange chromatography following nickel affinity chromatography purification of Nb35. The nanobody eluted in two populations (shown in red) as a minor peak and a major homogeneous peak which was collected, spin concentrated, and used for crystallography following determination of proper mixing ratio with the R:G complex as shown in (b). b) The R:G complex was mixed with slight excess of Nb35 (1 to 1.2 molar ratio of R:G complex to Nb35) on the basis of their protein concentrations and verified by analytical gel filtration.

Nanobody-35 (Nb35) was expressed in the periplasm of *E. coli* strain WK6, extracted, and purified by nickel affinity chromatography according to previously described methods (Rasmussen, S. G. et al. Structure of a nanobody-stabilized active state of the beta(2) adrenoceptor. Nature 2011 469, 175-180) followed by ion-exchange chromatography (FIG. 18a) using a Mono S 10/100 GL column (GE Healthcare). Selected Nb35 fractions were dialysis against buffer (10 mM HEPES, pH 7.5, 100 mM NaCl) and concentrated to approximately 65 mg ml-1 with a 10 kDa MWCO Millipore concentrator.

Complex Formation, Stabilization and Purification

Figure 19:
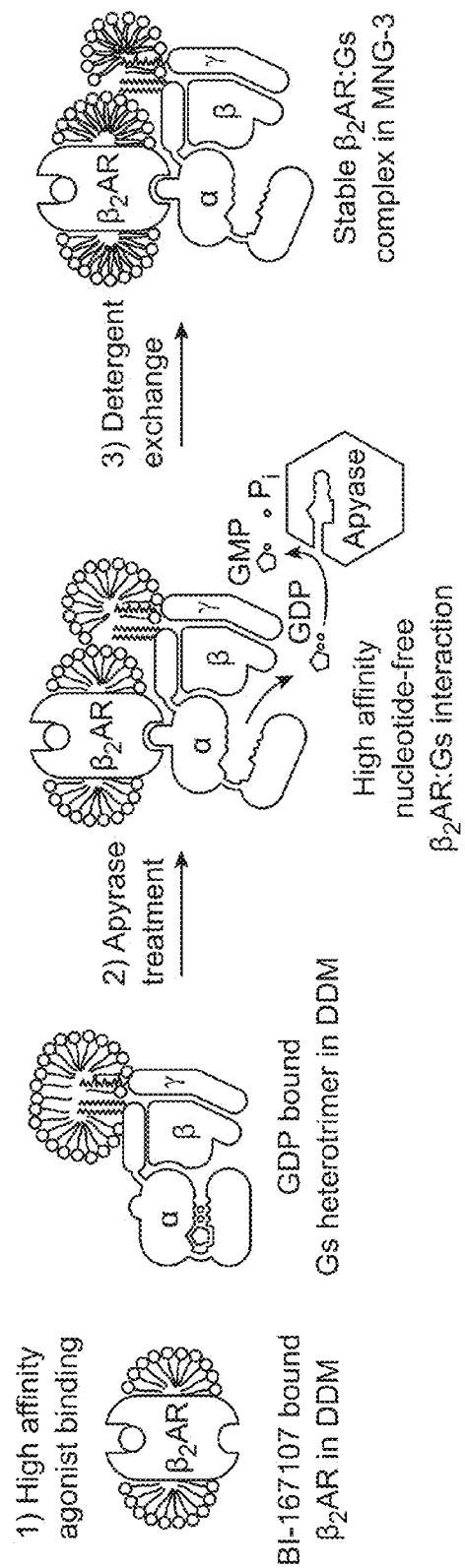
FIG. 19. Formation of a stable R:G complex. A stable complex was achieved by the combined effects of: 1) binding a high affinity agonist to the receptor with an extremely slow dissociation rate (as described in Rasmussen et al., 2011); 2) formation of a nucleotide free complex in the presence of apyrase that hydrolyses released GDP preventing it from rebinding and causing a less stable R:G interaction; and 3) detergent exchange of DDM for MNG-3 that stabilizes the complex.

Formation of a stable complex (see FIG. 19) was accomplished by mixing Gs heterotrimer at approximately 100 µM concentration with BI-167107 bound T4L-β$_2$AR (or β$_2$AR-365) in molar excess (approximately 130 µM) in 2 ml buffer (10 mM HEPES, pH 7.5, 100 mM NaCl, 0.1% DDM, 1 mM EDTA, 3 mM MgCl$_2$, 10 µM BI-167107) and incubating for 3 hrs at room temperature. BI-167107, which was identified from screening and characterizing approximately 50 different β$_2$AR agonists, has a dissociation half-time of approximately 30 hrs providing higher degree of stabilization to the active G protein-bound receptor than other full agonists such as isoproterenol (Rasmussen, S. G. et al. Structure of a nanobody-stabilized active state of the beta(2) adrenoceptor. Nature 2011 469, 175-180). To maintain the high-affinity nucleotide-free state of the complex, apyrase (25 mU/ml, NEB) was added after 90 min to hydrolyze residual GDP released from Gα upon binding to the receptor. GMP resulting from hydrolysis of GDP by apyrase has very poor affinity for the G protein in the complex. Rebinding of GDP can cause dissociation of the R:G complex (FIG. 13A).

Figure 20:
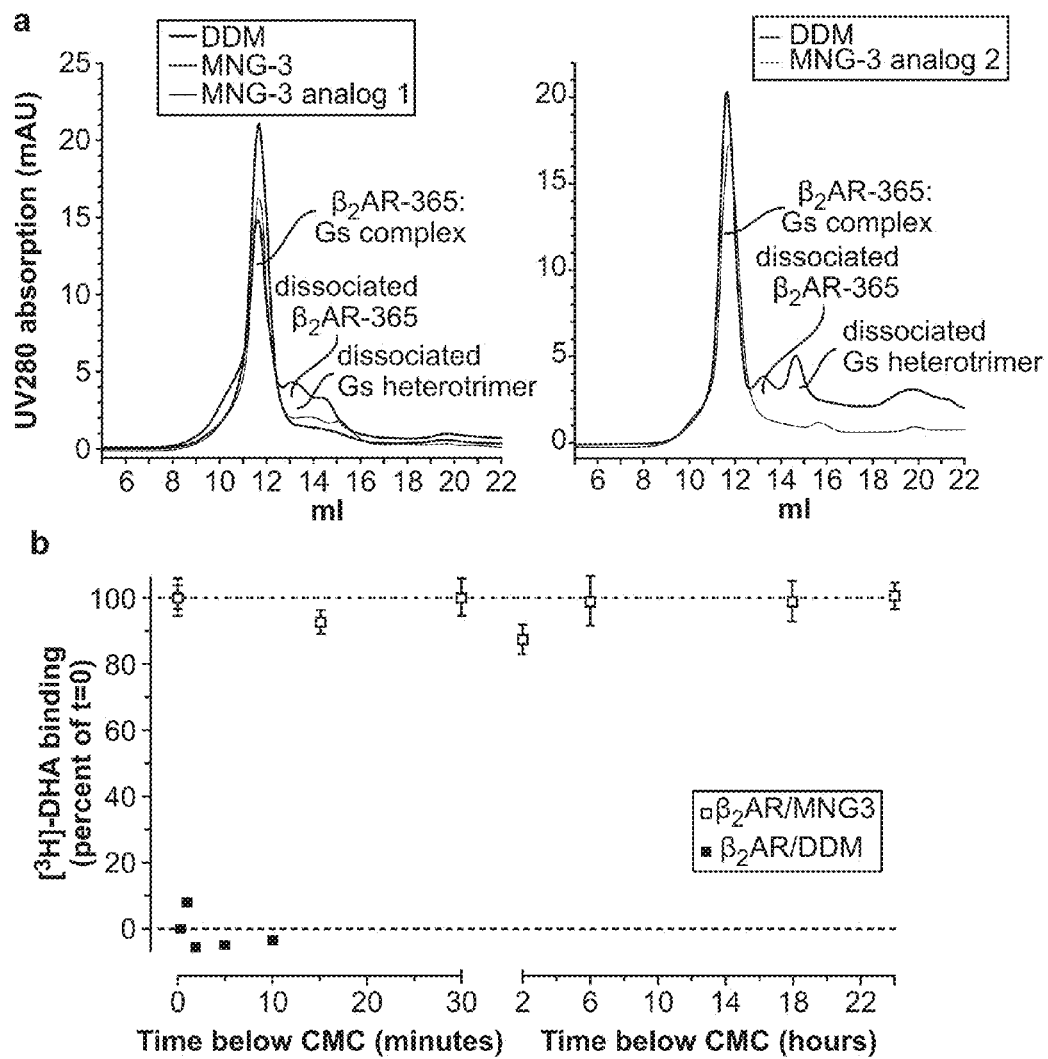
FIG. 20. Stabilizing effect of MNG-3 on the R:G complexes a) Analytical gel filtration of R:G complexes purified in DDM (in black), MNG-3 (in blue), or two MNG-3 analogs (in red and green) following incubation for 48 hrs at 4° C. In contrast to DDM, the R:G complexes are stable in the MNG detergents. b) Effect of diluting unliganded purified β2AR in either DDM or MNG-3 below the critical micelle concentration (CMC) of the detergent. Functional activity of the receptor was determined by 3H-dihydro alprenolol (3H-DHA) saturation binding. Diluting 2AR maintained in DDM by 1000-fold below the CMC cause loss in 3H-DHA binding (black data points) after 20 sec. In contrast, β2AR in MNG-3 diluted 1000-fold below the CMC maintained full ability to bind 3H-DHA after 24 hrs.

The R:G complex in DDM shows significant dissociation after 48 hours at 4° C. (FIG. 20A). Over 50 amphiphiles were screened and identified MNG-3 (Rasmussen, S. G. et al. Structure of a nanobody-stabilized active state of the beta(2) adrenoceptor. Nature 2011 469, 175-180; Chae, P. S. et al. Maltose-neopentyl glycol (MNG) amphiphiles for solubilization, stabilization and crystallization of membrane proteins. Nat Methods 7, 1003-1008; NG-310, Affymetrix-Anatrace) and its closely related analogs as detergents that substantially stabilize the complex (FIGS. 20A and B). The complex was exchanged into MNG-3 by adding the R:G mixture (2 ml) to 8 ml buffer (20 mM HEPES, pH 7.5, 100 mM NaCl, 10 μM BI-167107) containing 1% MNG-3 for 1 hr at room temperature.

Figure 17:
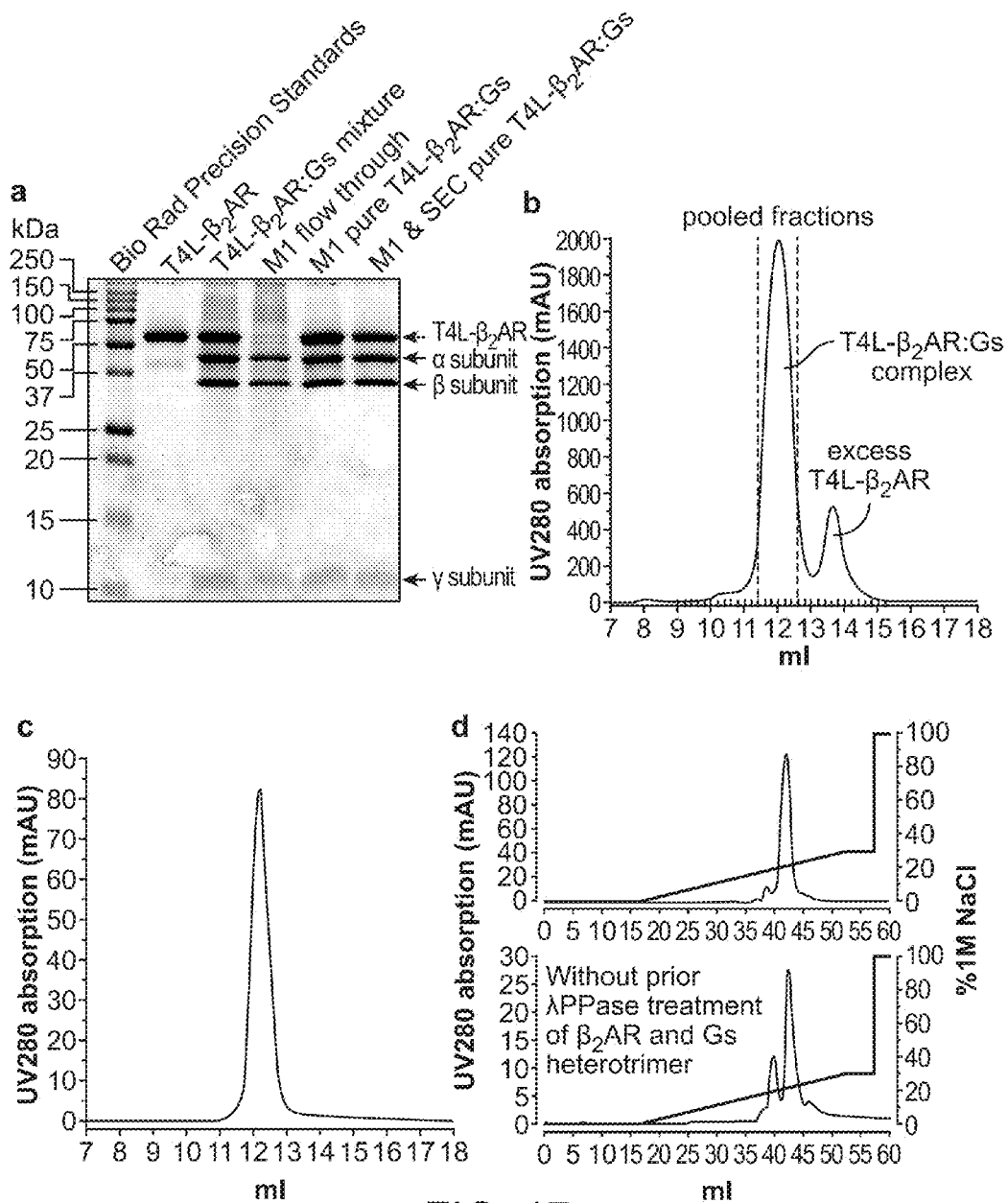
FIG. 17. Purity and homogeneity of the R:G complex: a) Analytical SDS-PAGE/Coomassie blue stain of samples obtained at various stages of receptor-G protein purification. BI167107 agonist bound, dephosphorylated, and deglycosylated receptor is used in excess of Gs heterotrimer for optimal coupling efficiency with the functional fraction of the G protein. Functional purification of Gs is archived through its interaction with the immobilized receptor on the M1 resin while non-functional/non-binding Gs is not retained. b) A representative elution profile of one of four consecutive preparative size exclusion chromatography (SEC) runs with fractionation indicated in red. SEC fractions containing the R:G complex (within the indicated dashed lines) were pooled, spin concentrated, and analyzed for purity and homogeneity by SDS-PAGE/Coomassie blue (a, lane 6), gel filtration (c), and by anion exchange chromotography (d). d) Upper panel shows elution proÿle from an analytical ion exchange chromatography (IEC) run of β2AR-365:Gs complex that was treated with λ phosphatase prior to complex formation. Lower panel shows IEC of complex which was not dephosphorylated resulting in a heterogeneous preparation. Off-peak fractions from the preparative SEC (b) were used for analytical gel filtration experiments shown in FIGS. 13 and 21.
Figure 21:
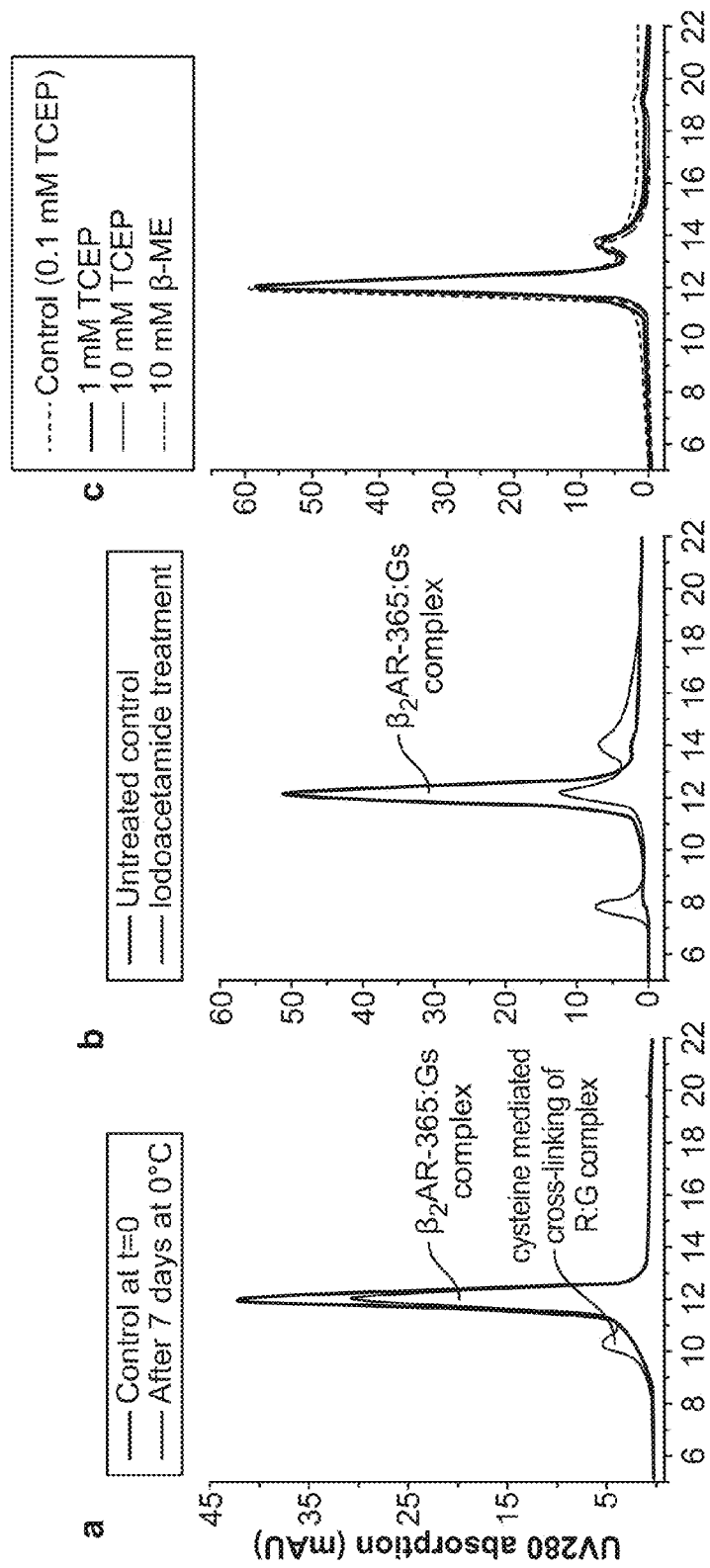
FIG. 21. Effect of alkylating and reducing agents on the stability and aggregation of the R:G complex. a) Disulfide-mediated aggregation of the R:G complex was observed by size exclusion chromatography (SEC) following incubation at 0° C. for 7 days in buffer containing 0.1 mM tris(2-carboxyethyl)phosphine (TCEP). b) Treatment of the complex with iodoacetamide (5 mM for 20 hrs at 20° C.) led to dissociation of the complex. Alkylating free cysteines with iodoacetic acid and cadmium chloride also led to dissociation. c) Disulfide-mediated aggregation of the complex could be prevented by higher concentrations of reducing agents. Shown are the effects of 0.1, 1, and 10 mM TCEP for 1 hr at 20° C., or 10 mM betamercaptoethanol (β-ME, 1 hr at 20° C.). Crystallization setups were performed using 1 to 5 mM TCEP, which was essential for optimal crystal growth.

At this stage the mixture contains the R:G complex, non-functional Gs, and an excess of β$_2$AR. To separate functional R:G complex from non-functional Gs, and to complete the detergent exchange, the R:G complex was immobilized on M1 Flag resin and washed in buffer (20 mM HEPES, pH 7.5, 100 mM NaCl, 10 μM BI-167107, and 3 mM CaCl$_2$) containing 0.2% MNG-3. To prevent cysteine bridge-mediated aggregation of R:G complexes, 100 μM TCEP was added to the eluted protein prior to concentrating it with a 50 kDa MWCO Millipore concentrator. Of note, it was discovered later that crystal growth improved at even higher TCEP concentrations (above 1 mM) compared to 100 μM TCEP, and that the integrity of the R:G complex in MNG-3 was stable to 10 mM TCEP as measured by gel filtration analysis (FIG. 21C). In contrast, DDM-solubilized β$_2$AR loses its ability to bind the high-affinity antagonist $^3$H-dihydroalprenolol in 10 mM TCEP (data not shown), probably due to disruption of extracellular disulfide bonds. Iodoacetamide could not be used to block reactive cysteines on G$_s$ alpha and beta subunits as it caused dissociation of the R:G complex (figure S9b). The final size exclusion chromatography procedure to separate excess free receptor from the R:G complex (FIG. 17b) was performed on a Superdex 200 10/300 GL column (GE Healthcare) equilibrated with buffer containing 0.02% MNG-3, 10 mM HEPES pH 7.5, 100 mM NaCl, 10 μM BI-167107, and 100 μM TCEP. Peak fractions were pooled (FIG. 17b) and concentrated to approximately 90 mg ml$^{-1}$ with a 100 kDa MWCO Viva-spin concentrator and analyzed by SDS-PAGE/Coomassie brilliant blue staining (FIG. 17a) and gel filtration (FIG. 17c). To confirm a pure, homogeneous, and dephosphorylated preparation, the R:G complex was routinely analyzed by ion exchange chromatography (FIG. 17d).

Protein Engineering

To increase the probability of obtaining crystals of the R:G complex two strategies were used to increase the polar surface area on the extracellular side of the receptor. The first approach, to generate extracellular binding antibodies, was not successful. The second approach was to replace the flexible and presumably unstructured N-terminus with the globular protein T4 lysozyme (T4L) used previously to crystallize and solve the carazolol-bound receptor (Rosenbaum, D. M. et al. GPCR engineering yields high-resolution structural insights into beta2-adrenergic receptor function. Science 2007 318, 1266-1273). The construct used here (T4L-β$_2$AR) contained the cleavable signal sequence followed by the M1 Flag epitope (DYKDDDDA; SEQ ID NO: 14), the TEV protease recognition sequence (ENLYFQG; SEQ ID NO: 15), bacteriophage T4 lysozyme from N2 through Y161 including C54T and C97A mutations, and a two residue alanine linker fused to the human β$_2$AR sequence D29 through G365. The PNGaseF-inaccessible glycosylation site of the β$_2$AR at N187 was mutated to Glu. M96 and M98 in the first extracellular loop were each replaced by Thr to increase the otherwise low expression level of T4L-β$_2$AR. The threonine mutations did not affect ligand binding affinity for $^3$H-dihydro-alprenolol, but caused a small, approximately two-fold decrease in affinity for isoproterenol.

The β$_2$AR-Gs peptide fusion construct used for [$^3$H]-DHA competition binding with isoproterenol was constructed from the receptor truncated at position 365 and fused to the last 21 amino acids of the Gαs subunit (amino acids 374-394, except for C379A). A Gly-Ser is inserted between the receptor and the peptide. Also an extended TEV protease site (SENLYFQGS; SEQ ID NO: 16) was introduced in the β$_2$AR between G360 and G361.

Stabilization of Gs with Nanobodies

From negative stain EM imaging, we observed that the alpha helical domain of Gαs was flexible and therefore possibly responsible for poor crystal quality. Targeted stabilization of this domain was addressed by immunizing two llamas (Llama glama) with the bis(sulfosuccinimidyl)glutarate (BS2G, Pierce) cross-linked β$_2$AR-Gs-BI-167107 ternary complex. Peripheral blood lymphocytes were isolated from the immunized animals to extract total RNA, prepare cDNA and construct a Nanobody phage display library according to published methods. Nb35 and Nb37 were enriched by two rounds of biopanning on the β$_2$AR-Gs-BI-167107 ternary complex embedded in biotinylated high-density lipoprotein particles (Whorton, et al. Proc Natl Acad Sci USA 2007 104, 7682-7687). Nb35 and Nb37 were selected for further characterization because they bind the β$_2$AR-Gs-BI-167107 ternary complex but not the free receptor in an ELISA assay. Nanobody binding to the R:G complex was confirmed by size exclusion chromatography (FIG. 13d), and it was noted that both nanobodies protected the complex from dissociation by GTPγS, suggestive of a stabilizing Gs:Nb interaction (FIG. 13d).

Crystallization

BI-167107 bound T4L-β$_2$AR:Gs complex and Nb35 were mixed in 1:1.2 molar ratio. The small molar excess of Nb35 was verified by analytical gel filtration (see FIG. 15b). The mixture incubated for 1 hr at room temperature prior to mixing with 7.7 MAG containing 10% cholesterol (C8667, Sigma) in 1:1 protein to lipid ratio (w/w) using the twin-syringe mixing method reported previously. The concentration of R:G:Nb complex in 7.7 MAG was approximately 25 mg ml$^{-1}$. The detergent MNG-3 may stabilize the T4L-β$_2$AR-Gs complex during its incorporation into the lipid cubic phase. This may be due to the high affinity of MNG-3 for the receptor. The β$_2$AR in MNG-3 maintains its structural integrity even when diluted below the CMC of the detergent, in contrast to β$_2$AR in DDM, which rapidly loses binding activity (FIG. 20b). Moreover, MNG-3 improved crystal size and quality, as previously reported. The protein:lipid mixture was delivered through an LCP dispensing robot (Gryphon, Art Robbins Instruments) in 40 nl drops to either 24-well or 96-well glass sandwich plates and overlaid en-bloc with 0.8 μl precipitant solution. Multiple crystallization leads were initially identified using in-house screens partly based on reagents from the StockOptions Salt kit (Hampton Research). Crystals for data collection were grown in 18 to 22% PEG 400, 100 mM MES pH 6.5 (FIG. 13c), 350 to 450 mM potassium nitrate, 10 mM foscarnet (FIG. 13b), 1 mM TCEP (FIG. 21c), and 10 μM BI-167107 Crystals reached full size within 3-4 days at 20° C. and were picked from a sponge-like mesophase and flash-frozen in liquid nitrogen without additional cryo-protectant.

Microcrystallography Data Collection and Processing.

Diffraction data were measured at the Advanced Photon Source beamline 23 ID-B. Hundreds of crystals were screened, and a final dataset was compiled using diffraction wedges of typically 10 degrees from 20 strongly diffracting crystals. All data reduction was performed using HKL2000 (Otwinowski. & Minor, W. Processing of x-ray diffraction data collected in oscillation mode. Methods Enzymol. 1997 276, 307-326). Although in many cases diffraction to beyond 3 Å was seen in initial frames, radiation damage and anisotropic diffraction resulted in low completeness in higher resolution shells. Analysis of the final dataset by the UCLA diffraction anisotropy server [31] indicated that diffraction along the a* axis was superior to that in other directions. On the basis of an F/σ (F) cutoff of 3 along each reciprocal space axis, reflections were subjected to an anisotropic truncation with resolution limits of 2.9, 3.2, and 3.2 Angstroms along a*, b*, and c* prior to use in refinement. The structure is reported to an overall resolution of 3.2 Å. Despite the low completeness in the highest resolution shells (Table 3) inclusion of these reflections gave substantial improvements in map quality and lower Rfree during refinement.

Structure Solution and Refinement

The structure was solved by molecular replacement using Phaser. In order, the search models used were: the β and γ subunits from a Gi heterotrimer (PDB ID: 1GP2), the Gs alpha ras-like domain (PDB ID: 1AZT), the active-state β2 adrenergic receptor (PDB ID: 3P0G), a $β_2AR$ binding nanobody (PDB ID: 3P0G), T4 lysozyme (PDB ID: 2RH1), and the Gs alpha helical domain (PDB ID: 1AZT). Following the determination of the initial structure by molecular replacement, rigid body refinement and simulated annealing were performed in Phenix and BUSTER, followed by restrained refinement and manual rebuilding in Coot. After iterative refinement and manual adjustments, the structure was refined in CNS using the DEN method. Although the resolution of this structure exceeds that for which DEN is typically most useful, the presence of several poorly resolved regions indicated that the incorporation of additional information to guide refinement could provide better results. The DEN reference models used were those used for molecular replacement, with the exception of NB35, which was well ordered and for which no higher resolution structure is available. Side chains were omitted from 52 residues for which there was no electron density past Cβ below a low contour level of 0.7σ in a 2Fo-Fc map. Figures were prepared using PyMOL (The PyMOL Molecular Graphics System, Version 1.3, Schrödinger, LLC.). MolProbity was used to determine Ramachandran statistics.

Competition Binding

Membranes expressing the $β_2AR$ or the $β_2AR$-Gs peptide fusion were prepared from baculovirus-infected Sf9 cells and [$^3$H]-dihydroalprenolol ([$^3$H]-DHA) binding performed as previously described (Swaminath et al Mol Pharmacol 2002 61, 65-72). For competition binding, membranes were incubated with [$^3$H]-DHA (1.1 nM final) and increasing concentrations of (−)-isoproterenol (ISO) for 1 hr before harvesting onto GF/B filters. Competition data were fitted to a two-site binding model and ISO high and low Ki's and fractions calculated using GraphPad prism.

Results II

Crystallization of the β2AR-Gs Complex

One challenge for crystallogenesis was to prepare a stable $β_2AR$-Gs complex in detergent solution. The $β_2AR$ and Gs couple efficiently in lipid bilayers, but not in detergents used to solubilize and purify these proteins. We found that a relatively stable $β_2AR$-Gs complex could be prepared by mixing purified GDP-Gs (approximately 100 μM final concentration) with a molar excess of purified $β_2AR$ bound to a high affinity agonist (BI-167107, Boehringer Ingelheim) in dodecylmaltoside solution. Apyrase, a non-selective purine pyrophosphatase, was added to hydrolyze GDP released from Gs on forming a complex with the $β_2AR$. The complex was subsequently purified by sequential antibody affinity chromatography and size exclusion chromatography. The stability of the complex was enhanced by exchanging it into a recently developed maltose neopentyl glycol detergent (NG-310, Anatrace). The complex could be incubated at room temperature for 24 hrs without any noticeable degradation; however, initial efforts to crystallize the complex using sparse matrix screens in detergent micelles, bicelles and lipidic cubic phase (LCP) failed.

To further assess the quality of the complex, the protein was analyzed by single particle electron microscopy (EM). The results confirmed that the complex was monodispersed, and revealed two potential problems for obtaining diffraction of quality crystals. First, the detergent used to stabilize the complex formed a large micelle, leaving little polar surface on the extracellular side of the $β_2AR$-Gs complex for the formation of crystal lattice contacts. The initial approach to this problem, which was to generate antibodies to the extracellular surface, was not successful. As an alternative approach, we replaced the amino terminus of the $β_2AR$ with T4 lysozyme (T4L). Several different amino-terminal fusion proteins were prepared and single particle EM was used to identify a fusion with a relatively fixed orientation of T4L in relation to the $β_2AR$.

Figure 7:
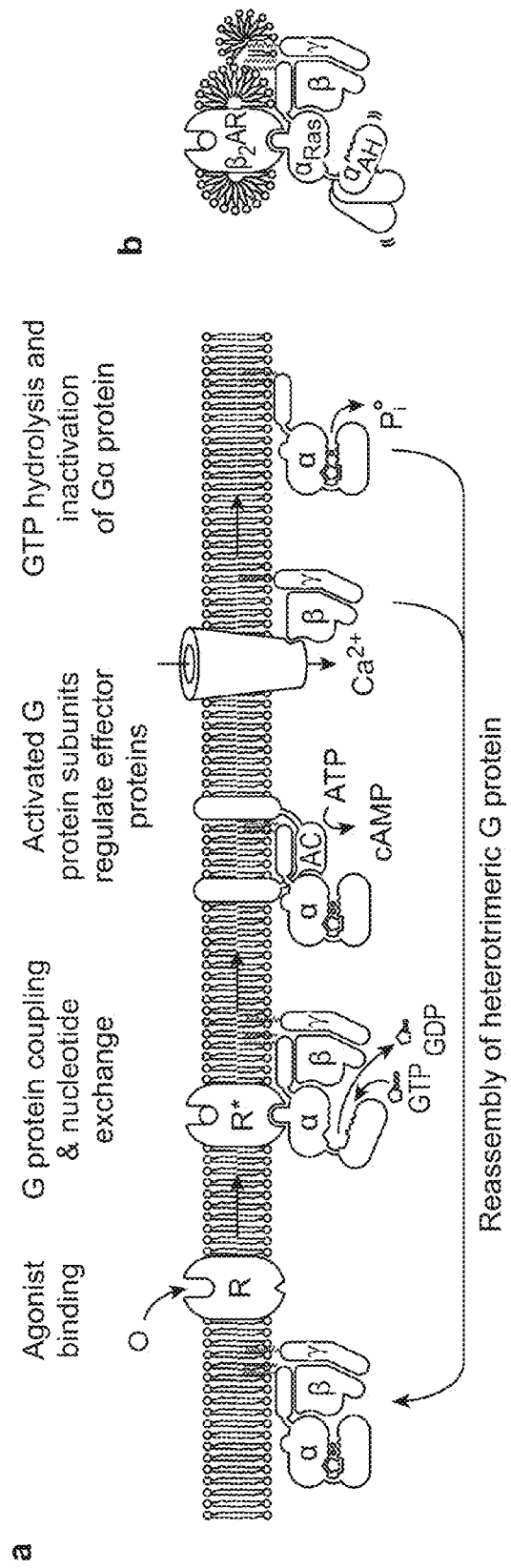
FIG. 7. G protein cycle for the $β_2AR$-Gs complex. a, Extracellular agonist binding to the $β_2AR$ leads to conformational rearrangements of the cytoplasmic ends of transmembrane segments that enable the $G_s$ heterotrimer (α, β, and γ) to bind the receptor. GDP is released from the α subunit upon formation of R:G complex. The GTP binds to the nucleotide-free α subunit resulting in dissociation of the α and βγ subunits from the receptor. The subunits regulate their respective effector proteins adenylyl cyclase (AC) and $Ca^{2+}$ channels. The $G_s$ heterotrimer reassembles from α and βγ subunits following hydrolysis of GTP to GDP in the α subunit. b, The purified nucleotide-free $β_2AR$-Gs protein complex maintained in detergent micelles. The Gsα subunit consists of two domains, the Ras domain (αRas) and the α-helical domain (αAH). Both are involved in nucleotide binding. In the nucleotide-free state, the αAH domain has a variable position relative the αRas domain.

The second problem revealed by single particle EM analysis was increased variability in the positioning of the α-helical component of the Gαs subunit. Gαs consists of two domains, the ras-like GTPase domain (GαsRas), which interacts with the $β_2AR$ and the Gβ subunit, and the α-helical domain (GαsAH). The interface of the two Gαs subdomains forms the nucleotide-binding pocket (FIG. 7), and EM 2D averages and 3D reconstructions show that in the absence of guanine nucleotide, GαsAH has a variable position relative to the complex of T4L-$β_2AR$-GαsRAS-Gβγ (FIG. 7b).

Figure 13:
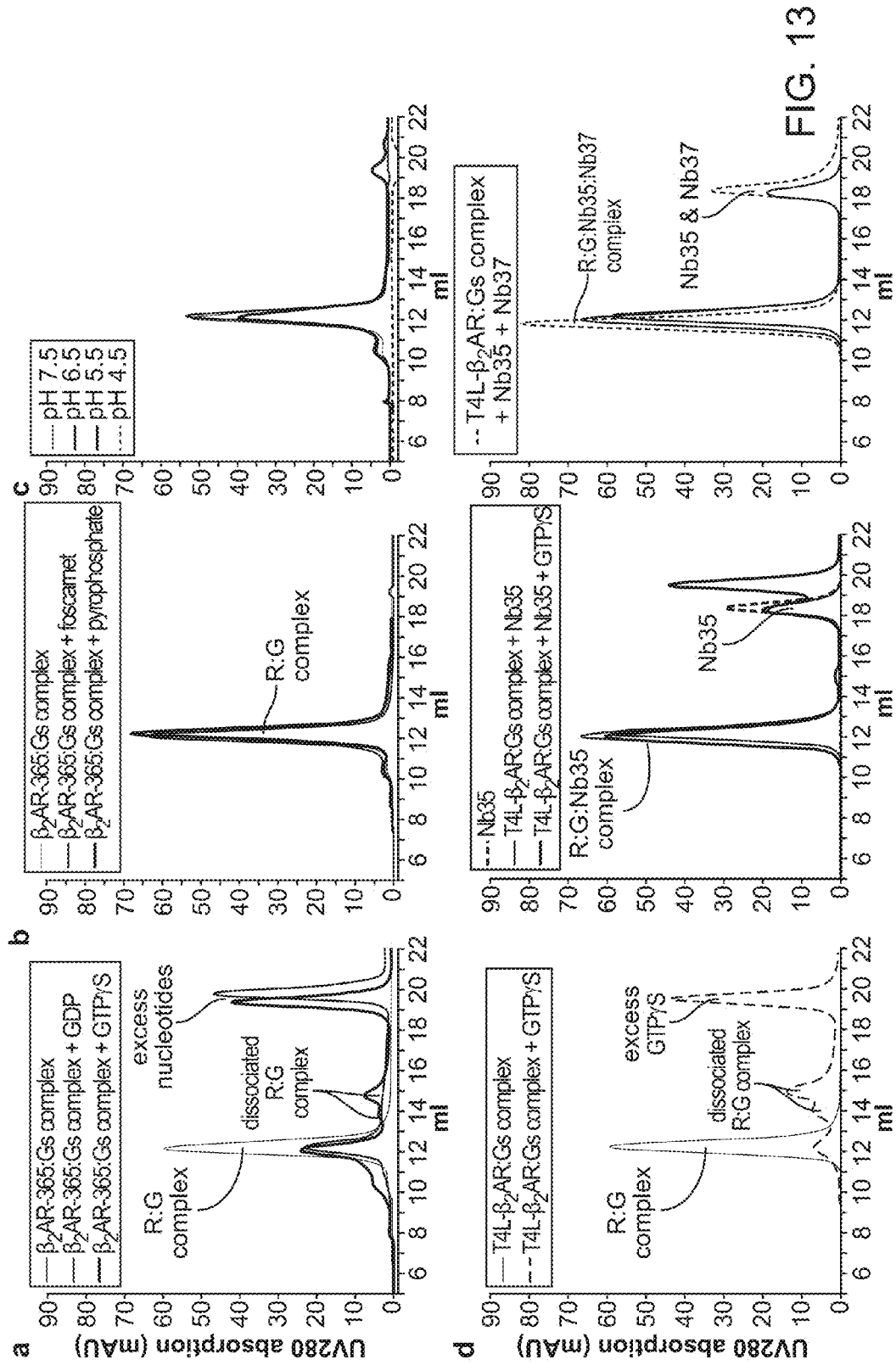
FIG. 13. Effect of nucleotide analogs, pH, and nanobodies on the stability of the R:G complex. a) Analytical gel filtration showing that nucleotides GDP and GTPγS (0.1 mM) cause dissociation of the R:G complex. b) The phosphates pyrophosphate and foscarnet (used at 5 mM) resemble the nucleotide phosphate groups, but do not cause disruption of the complex. When used as additives they improved crystal growth of both the T4L-β2AR:Gs complex (without nanobodies), T4L-β2AR:Gs:Nb37, and T4L-β2AR:Gs:Nb35. c) The pH limit was determined to guide the preparation of crystallization screens. For the same purpose the effect of ionic strength (data not shown) was determined using NaCl at various concentrations. The complex is stable in 20, 100, and 500 mM but dissociates at 2.5 M NaCl. d) Nanobody 35 (Nb35, broken line) binds to the R:G complex (solid line) to form the R:G:Nb35 complex (red solid line) which is insensitive to GTP°S treatment (solid line) in contrast to the treated R:G complex alone (broken line). Nb35 and Nb37 binds separate epitopes on the Gs heterotrimer to form a R:G:Nb35:Nb37 complex (solid line). Nb37 binding also prevents GTP°S from dissociating the R:G complex (data not shown).

The variable position of GαsAH was attributed to the empty nucleotide-binding pocket. However, both GDP and nonhydrolyzable GTP analogs disrupt the $β_2AR$-Gs complex (FIG. 13). The addition of pyrophosphate and its analog phosphonoformate (foscarnet) led to a significant increase in stabilization of GαsAH as determined by EM analysis of the detergent solubilized complex. Crystallization trials were carried out in Lipidic Cubic Phase (LCP) using a modified monolein designed to accommodate the large hydrophilic component of the T4L-β2AR-Gs complex (Misquitta, L. V. et al. Membrane protein crystallization in lipidic mesophases with tailored bilayers. Structure 2004 12, 2113-2124). Although we were able to obtain small crystals that diffracted to 7 Å, we were unable to improve their quality through the use of additives and other modifications.

Figure 14:
FIG. 14. Crystals of the T4L-β2AR:Gs:Nb35 complex in sponge-like mesophase

In an effort to generate an antibody that would further stabilize the complex and facilitate crystallogenesis, β2AR and the Gs heterotrimer were crosslinked with a small, homobifunctional amine-reactive crosslinker and used this stabilized complex to immunized llamas. Llamas and other camelids produce antibodies devoid of light chains. The single domain antigen binding fragments of these heavy chain only antibodies, known as nanobodies, are small (15 kDa), rigid and are easily cloned and expressed in E. coli. A nanobody (Nb35) was obtained that binds to the complex and prevents dissociation of the complex by GTPγS (FIG. 13). The T4L-β2AR-Gs-Nb35 complex was used to obtain crystals that grew to 250 microns (FIG. 14) in LCP (monoolein 7.7) and diffracted to 2.9 Å. A 3.2 Å data set was obtained from 20 crystals and the structure was determined by molecular replacement.

Figure 8:
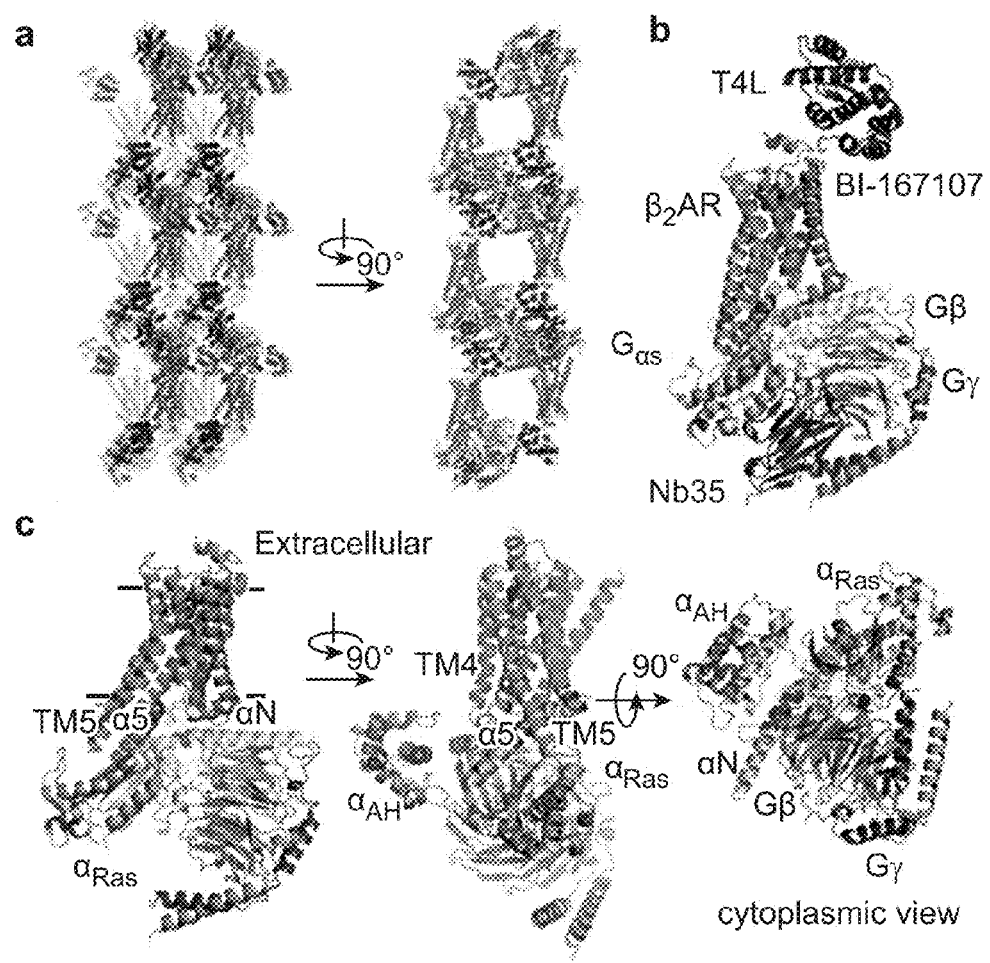
FIG. 8. Overall structure of the $β_2AR$ Gs complex. a, Lattice packing of the complex shows alternating layers of receptor and G protein within the crystal. Abundant contacts are formed among proteins within the aqueous layers. b, The overall structure of the asymmetric unit contents shows the $β_2AR$ bound to an agonist (spheres) and engaged in extensive interactions with Gsα. Gαs together with Gβ and Gγ constitute the heterotrimeric G protein Gs. A Gs binding nanobody binds the G protein between the α and β subunits. The nanobody (Nb35) facilitates crystallization, as does T4 lysozyme fused to the amino terminus of the $β_2AR$. c, The biological complex omitting crystallization aids, showing its location and orientation within a cell membrane.

The $β_2AR$-Gs complex crystallized in space group P2$_1$, with a single complex in each asymmetric unit. FIG. 8a shows the crystallographic packing interactions. Complexes are arrayed in alternating aqueous and lipidic layers with lattice contacts formed almost exclusively between soluble components of the complex, leaving receptor molecules suspended between G protein layers and widely separated from one another in the plane of the membrane. Extensive lattice contacts were formed among all the soluble proteins, likely accounting for the strong overall diffraction and remarkably clear electron density for the G protein. Nb35 and T4L facilitated crystal formation. Nb35 packs at the interface of Gβ and Gα subunits with complementarity determining region (CDR) 1 interacting primarily with Gβ and a long CDR3 loop interacting with both Gβ and Gα subunits. The framework regions of Nb35 from one complex also interact with Gα subunits from two adjacent complexes. T4L forms relatively sparse interactions with the amino terminus of the receptor, but packs against the amino terminus of the Gβ subunit of one complex, the carboxyl terminus of the Gβ subunit of another complex, and the Gβ subunit of yet another complex. FIG. 8b shows the structure of the complete complex including T4L and Nb35, and FIG. 8c shows the $β_2$AR-Gs complex alone.

Structure of the Active-State β2AR

Figure 9:
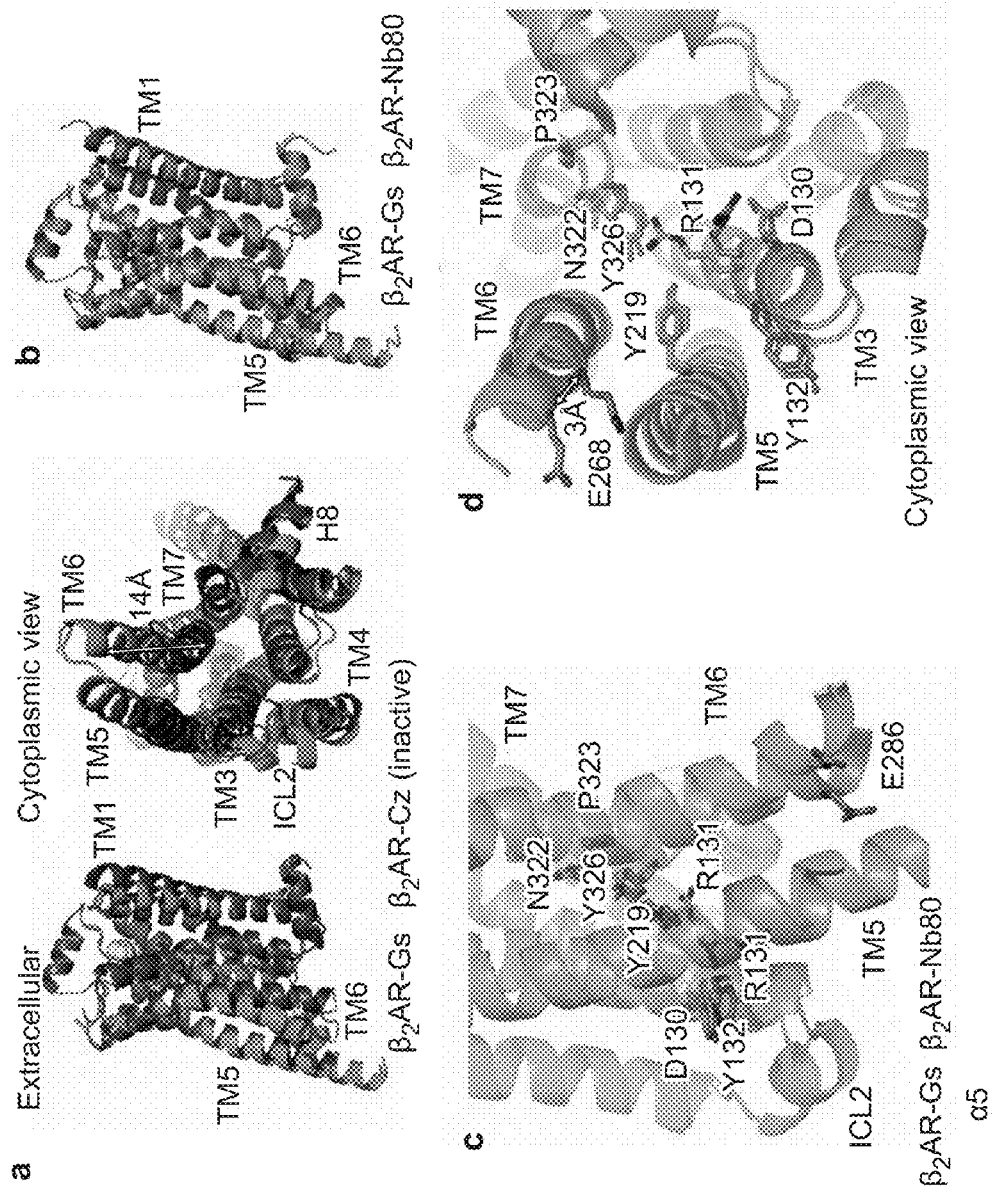
FIG. 9. Comparison of active and inactive $β_2AR$ structures. a, Side and cytoplasmic views of the $β_2AR$-Gs structure compared to the inactive carazolol-bound $β_2AR$ structure (blue). Significant structural changes are seen for the intracellular domain of TM5 and TM6. TM5 is extended by two helical turns while TM6 is moved outward by 14 Å as measured at the α-carbons of Glu268 in the two structures. b, $β_2AR$-Gs compared with the nanobody-stabilized active state $β_2AR$-Nb80 structure [12]c and d, The positions of residues in the E/DRY and NPxxY motifs and other key residues of the $β_2AR$-Gs and $β_2AR$-Nb80 structures as seen from the cytoplasmic side. All residues occupy very similar positions except Arg131 which in the $β_2AR$-Nb80 structure interacts with the nanobody.

The $β_2$AR-Gs structure provides the first high-resolution insight into the mechanism of signal transduction across the plasma membrane by a GPCR, and the structural basis for the functional properties of the ternary complex. FIG. 9a compares the structures of the agonist-bound receptor in the $β_2$AR-Gs complex and the inactive carazolol-bound $β_2$AR. The largest difference between the inactive and active structures is a 14 Å outward movement of TM6 when measured at the Cα carbon of E268. There is a smaller outward movement and extension of the cytoplasmic end of the TM5 helix by 7 residues. A stretch of 26 amino acids in the third intracellular loop (ICL3) is disordered. Another notable difference between inactive and active structures is the second intracellular loop (ICL2), which forms an extended loop in the inactive $β_2$AR structure and an α-helix in the $β_2$AR-Gs complex. This helix is also observed in the $β_2$AR-Nb80 structure (FIG. 9b); however, it may not be a feature that is unique to the active state, since it is also observed in the inactive structure of the highly homologous avian $β_1$AR.

The quality of the electron density maps for the $β_2$AR is highest at this $β_2$AR-GαsRas interface, and much weaker for the extracellular half, possibly due to the lack of crystal lattice contacts with the extracellular surface (FIG. 8a). As a result, we cannot confidently model the high-affinity agonist (BI-167107) in the ligand-binding pocket. However, the overall structure of the $β_2$AR in the T4L-$β_2$AR-Gs complex is very similar to our recent active-state structure of $β_2$AR stabilized by a G protein mimetic nanobody (Nb80). These structures deviate primarily at the cytoplasmic ends of TMs 5 and 6 (FIG. 9b), possibly due to the presence of T4L that replaces ICL3 in the $β_2$AR-Nb80 structure. Nonetheless, the $β_2$AR-Nb80 complex exhibits the same high affinity for the agonist isoproterenol as does the $β_2$AR-Gs complex, consistent with high structural homology around the ligand binding pocket. The electron density maps for the $β_2$AR-Nb80 crystals provide a more reliable view of the conformational rearrangements of amino acids around the ligand-binding pocket and between the ligand-binding pocket and the Gs-coupling interface.

Figure 15:
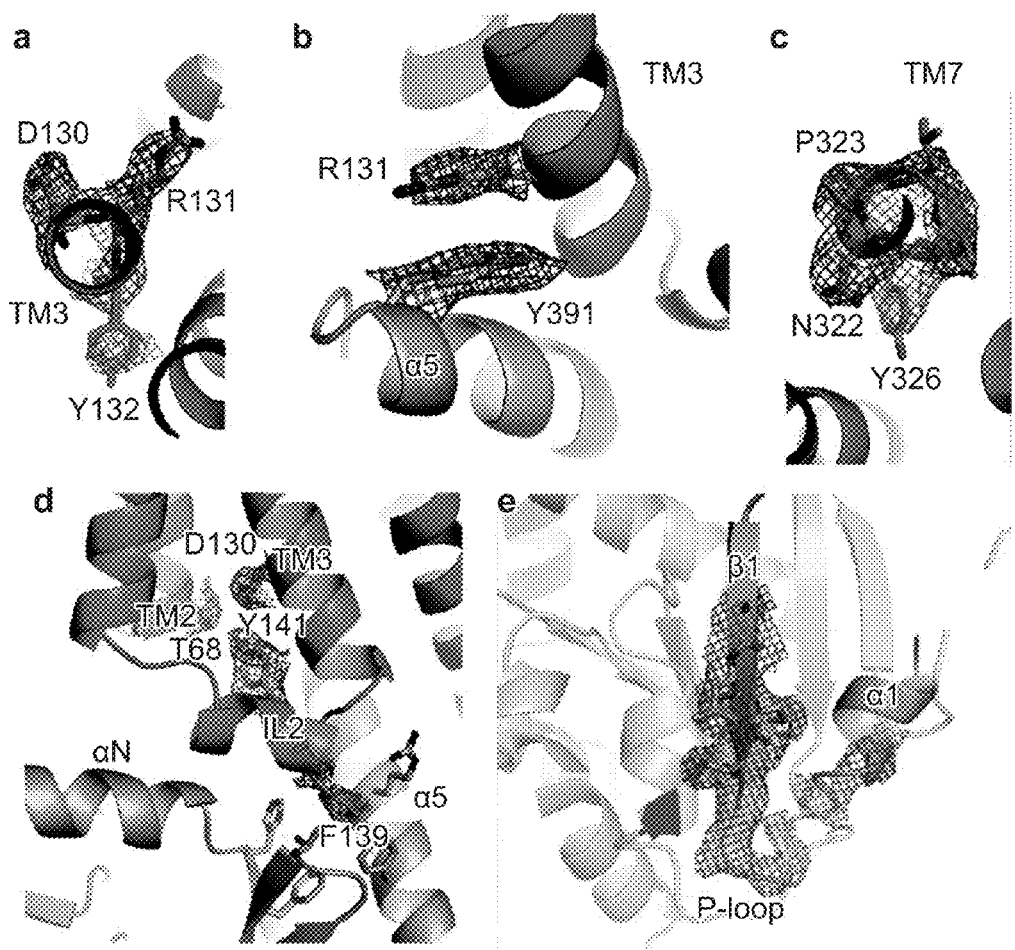
FIG. 15. Views of electron density for residues in the R:G interface. a) The D/ERY motif at the cytoplasmic end of TM3. b) Packing interaction between Arg131 of the E/DRY motif and Tyr391 of C-terminal Gsα. c) The NPxxY in the cytoplasmic end of TM7. d) Interactions of Thr68 and Tyr141 with Asp130 of the E/DRY motif. Phe139 of IL2 is buried in a hydrophobic pocket in Gsα. e) The β1-α1 loop (P-loop) of Gsα involved in nucleotide binding. Electron density maps are 2Fo-Fc maps contoured at 1 sigma.

FIG. 9c shows the position of the highly conserved sequence motifs including D/ERY and NPxxY in the $β_2$AR-Gs complex compared with the $β_2$AR-Nb80 complex (see also Fig. S3). These conserved sequences have been proposed to be important for activation or for maintaining the receptor in the inactive state. The positions of these amino acids are essentially identical in these two structures demonstrating that Nb80 is a very good G protein surrogate. Only Arg131 differs between these two structures. In the $β_2$AR-Nb80 structure Arg131 interacts with Nb80, whereas in the $β_2$AR-Gs structure Arg131 packs against Tyr391 of Gαs (FIG. 15).

Figure 10:
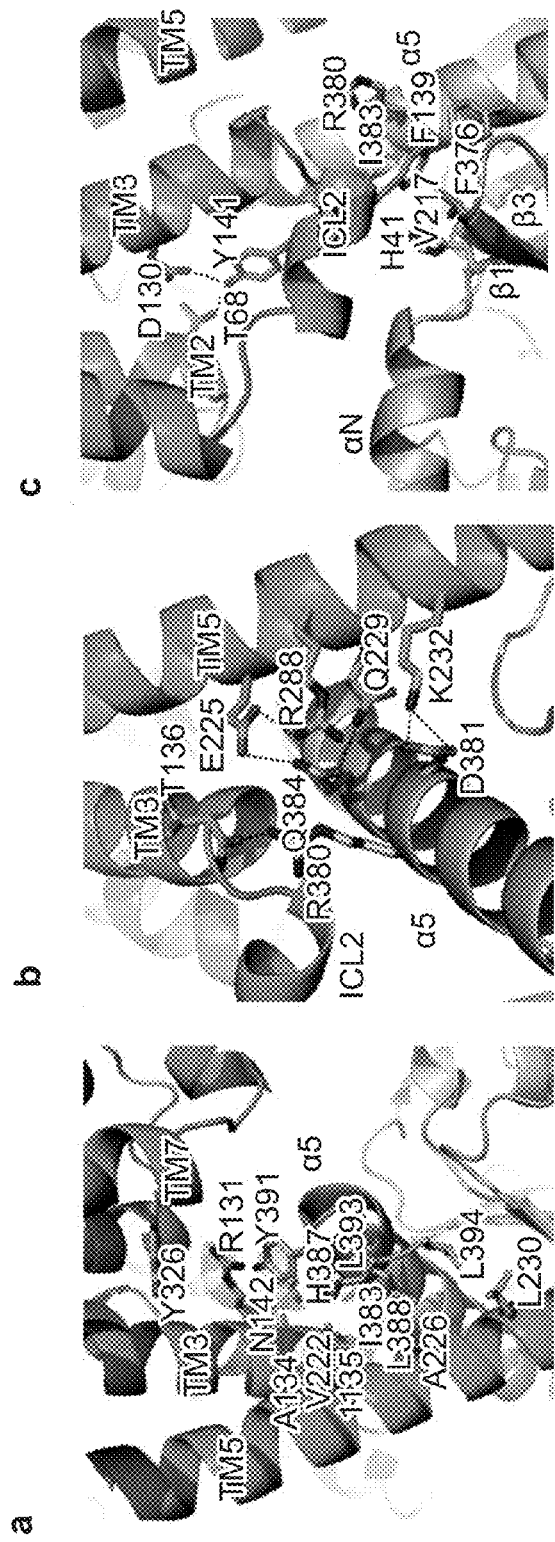
FIG. 10. Receptor-G protein interactions. a, b The α5-helix of Gαs docks into a cavity formed on the intracellular side of the receptor by the opening of transmembrane helices 5 and 6. a. Within the transmembrane core, the interactions are primarily non-polar. An exception involves packing of Tyr391 of the α5-helix against Arg131 of the conserved DRY sequence in TM3 (see also FIG. 15). Arg131 also packs against Tyr of the conserved NPxxY sequence in TM7. b. As α5-helix exits the receptor it forms a network of polar interactions with TM5 and TM3. c, Receptor residues Thr68 and Asp 130 interact with the IL2 helix of the $β_2AR$ via Tyr141, positioning the helix so that Phe139 of the receptor docks into a hydrophobic pocket on the G protein surface, thereby structurally linking receptor-G protein interactions with the highly conserved DRY motif of the $β_2AR$.

The active state of the $β_2$AR is stabilized by extensive interactions with (GαsRas) (FIG. 10). There are no direct interactions with Gβ or Gγ subunits. The total buried surface of the $β_2$AR-G⟨sRas interface is 2576 Å$^2$ (1300 Å$^2$ for G⟨sRas and 1276 Å$^2$ for the $β_2$AR). This interface is formed by ICL2, TM5 and TM6 of the $β_2$AR, and by α5-helix, the αN-β1 junction, the top of the β3-strand, and the α4-helix of GαsRas (see Table 1 below for specific interactions). The $β_2$AR sequences involved in this interaction have been shown to play a role in G protein coupling; however, there is no clear consensus sequence for Gs-coupling specificity when these segments are aligned with other GPCRs. Perhaps this is not surprising considering that the $β_2$AR also couples to Gi and that many GPCRs couple to more than one G protein isoform. The structural basis for G protein coupling specificity must therefore involve more subtle features of the secondary and tertiary structure. Nevertheless, a noteworthy interaction involves Phe139, which is located at the beginning of the ICL2 helix and sits in a hydrophobic pocket formed by Gαs His41 at the beginning of the β1-strand, Val213 at the start of the β3-strand and Phe376, Arg380 and Ile383 in the α5-helix (FIG. 4c). The $β_2$AR mutant F139A displays severely impaired coupling to Gs. The residue corresponding to Phe139 is a Phe or Leu on almost all Gs coupled receptors, but is more variable in GPCRs known to couple to other G proteins. Of interest, the ICL2 helix is stabilized by an interaction between Asp130 of the conserved DRY sequence and Tyr141 in the middle of the ICL2 helix (FIG. 10c). Tyr141 has been shown to be a substrate for the insulin receptor tyrosine kinase; however, the functional significance of this phosphorylation is currently unknown.

Structure of Activated Gs

One surprising observation in the $β_2$AR-Gs complex is the large displacement of the GαsAH relative to GαsRas (an approximately 127° rotation about the junction between the domains) (FIG. 11a). In the crystal structure of Gαs, the nucleotide-binding pocket is formed by the interface between GαsRas and GαsAH. Guanine nucleotide binding stabilizes the interaction between these two domains. The loss of this stabilizing effect of guanine nucleotide binding is consistent with the high flexibility observed for GαsAH in single particle EM analysis of the detergent solubilized complex. It is also in agreement with the increase in deuterium exchange at the interface between these two domains upon formation of the complex. Recently Hamm, Hubbell and colleagues, using double electron-electron resonance (DEER) spectroscopy, documented large (up to 20 Å) changes in distance between nitroxide probes positioned on the Ras and α-helical domains of Gi upon formation of a complex with light-activated rhodopsin. Therefore, it is perhaps not surprising that G⟨sAH is displaced relative to GαsRas; however, its location in this crystal structure most likely reflects only one of an ensemble of conformations that it can adopt under physiological conditions, but has been stabilized by crystal packing interactions.

Figure 11:
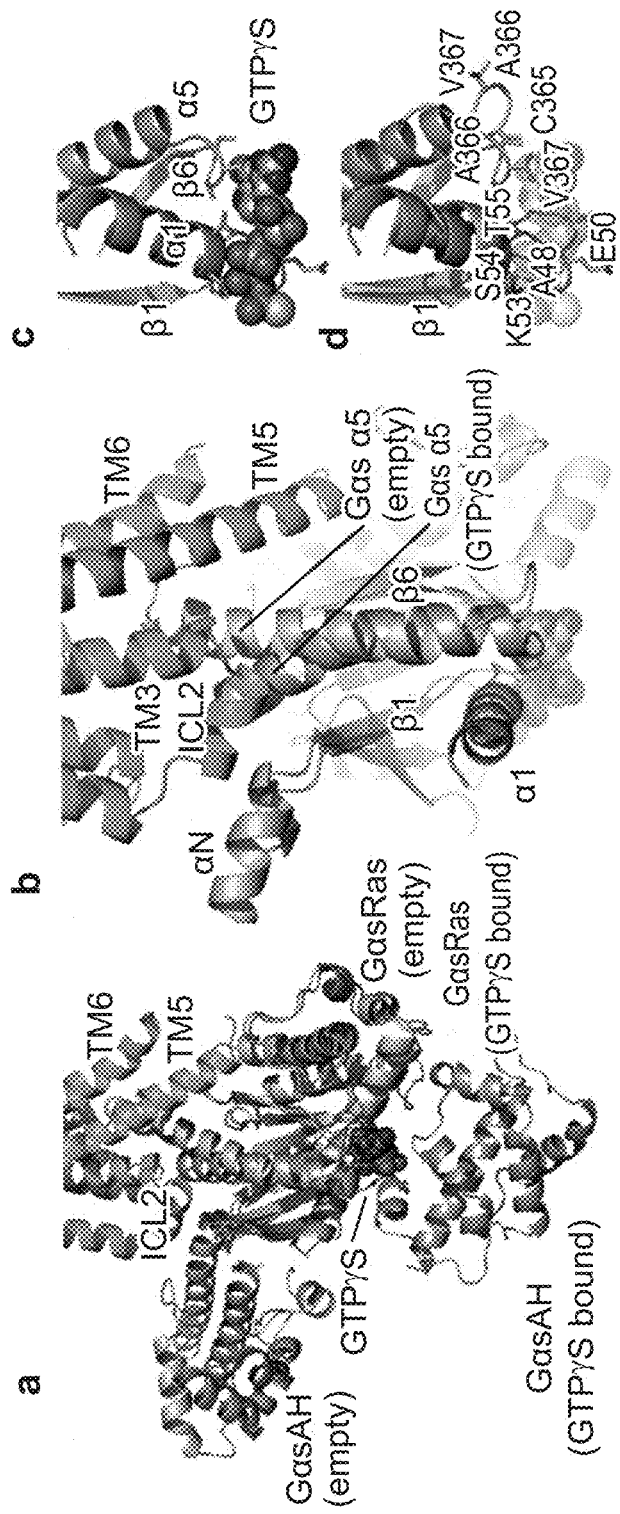
FIG. 11. Conformational changes in Gαs. a, A comparison of G⟨s in the $β_2AR$-Gs complex with the GTPγS-bound Gαs (PDB ID: 1AZT). GTPγS is shown as spheres. The helical domain of Gαs (GαsAH) exhibits a dramatic displacement relative to its position in the GTPγS-bound state. b, The α5-helix of Gαs is rotated and displaced toward the $β_2AR$, perturbing the β6-α5 loop which otherwise forms part of the GTPγS binding pocket. c, The β1-α1 loop (P-loop) and β6-α5 loop of Gαs interact with the phosphates and purine ring, respectively, of GTPγS in the GTPγS-G⟨s structure. d, The β1-α1 and β6-α5 loops are rearranged in the nucleotide-free $β_2AR$-Gs structure.

The conformational links between the $β_2$AR and the nucleotide-binding pocket primarily involve the amino and carboxyl terminal helices of Gαs (FIG. 10). FIG. 11b focuses on the region of GαsRas that undergoes the largest conformational change when comparing the structure of GαsRas from the Gs-$β_2$AR complex with that from the Gαs-GTPγS complex. The largest difference is observed for the α5-helix, which is displaced 6 Å towards the receptor and rotated as the carboxyl terminal end projects into transmembrane core of the β₂AR. Associated with this movement, the β6-α5 loop, which interacts with the guanine ring in the Gαs-GTPγS structure, is displaced outward, away from the nucleotide-binding pocket (FIG. 11b-d). The movement of α5-helix is also associated with changes in interactions between this helix and the β6-strand, the αN-β1 loop, and the α1-helix. The β1-strand forms another link between the β₂AR and the nucleotide-binding pocket. The C-terminal end of this strand changes conformation around Gly47, and there are further changes in the β1-α1 loop (P-loop) that coordinates the γ-phosphate in the GTP-bound form (FIG. 11 b-d). The observations in the crystal structure are in agreement with deuterium exchange experiments where there is enhanced deuterium exchange in the β1-strand and the amino terminal end of the α5-helix upon formation of the nucleotide-free β₂AR-Gs complex. The DXMS studies provide additional insights into the dynamic nature of these conformational changes in Gs upon complex formation.

The structure of a GDP-bound Gs heterotrimer has not been determined in this study, so it is not possible to directly compare the Gαs-Gβγ interface before and after formation of the β₂AR-Gs complex. Based on the structure of the GDP-bound Gi heterotrimer, large changes in interactions between GαsRas and Gβγ upon formation of the complex with β₂AR are not observed. This is also consistent with deuterium exchange studies. It should be noted that Nb35 binds at the interface between GαsRas and Gβ (FIG. 8b). Therefore, we cannot exclude the possibility that Nb35 may influence the relative orientation of the GαsRas-Gβγ interface in the crystal structure. However, single particle EM studies provide evidence that Nb35 does not disrupt interactions between GαsAH and GαsRas.

Assembly of the β2AR-Gs Complex

Figure 12:
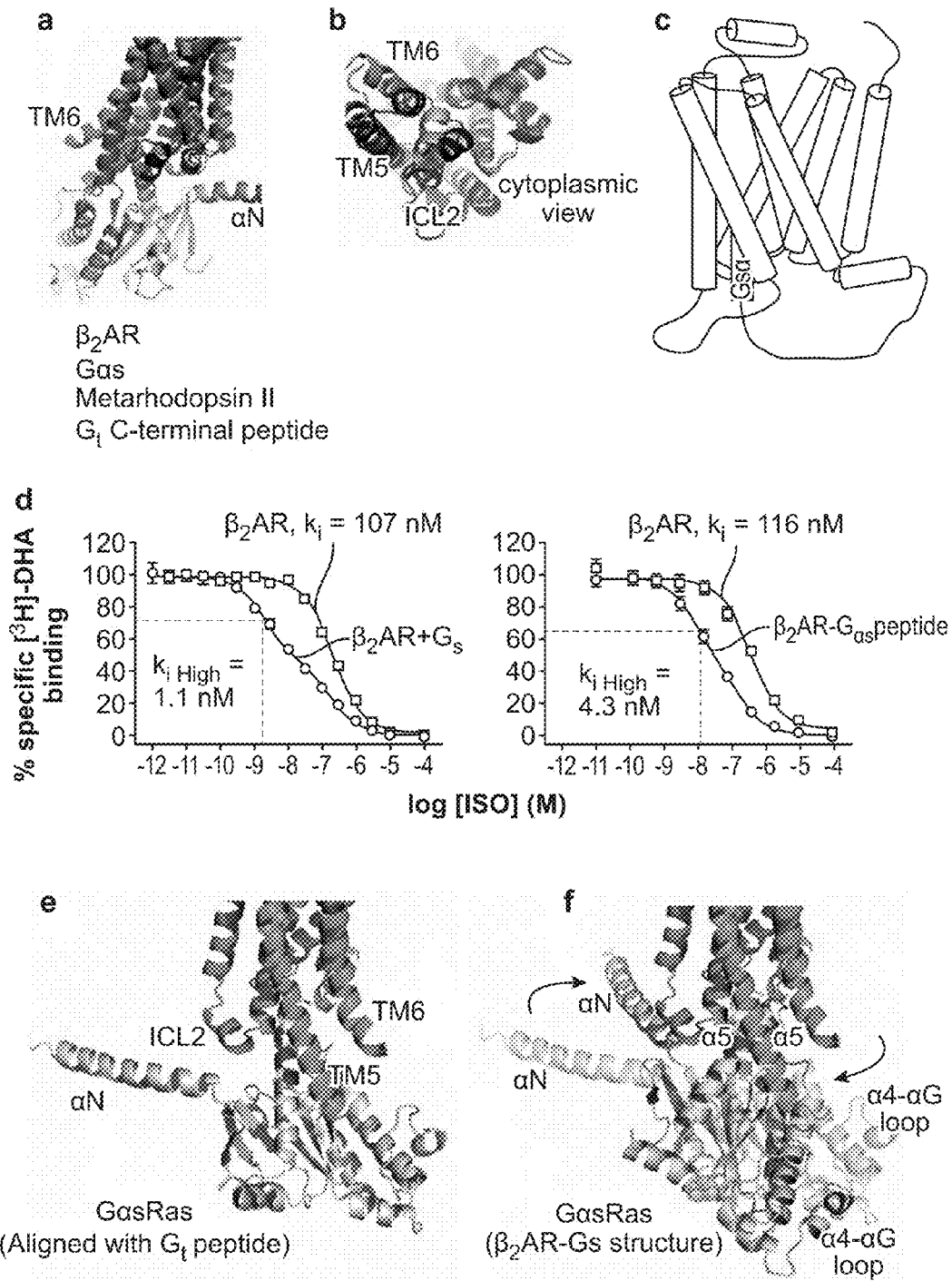
FIG. 12. Proposed model for structural changes causing GDP release from the R:G complex. a, Alignment of the TM segments of $β_2AR$ in the $β_2AR$-Gs structure and metarhodopsin II [24](PDB ID: 3PQR) (purple) bound with the C-terminal peptide of transducin (blue). b, The C-terminal end of G⟨sRas domain from the GTPγS bound Gs structure [22] (PDB ID: 1AZT) is aligned with the C-terminal peptide of transducin. The C-terminal end of the α5-helix was moved away from the rest of the G⟨sRas domain to avoid clashes with the $β_2AR$. c, Cartoon of the $β_2AR$-G⟨s peptide fusion construct used in the binding experiments (d). d, Competition binding experiments between [$^3$H]-DHA and full agonist isoproterenol. Top panel shows binding data (reproduced from Rasmussen et al., 2011) on $β_2AR$ reconstituted in HDL particles with and without Gs heterotrimer. The fraction of $β_2AR$ in the $K_{i\ high}$ state for the β$_2$AR with Gs is 0.55. Bottom panel shows binding to β$_2$AR and a β$_2$AR-Gαs peptide fusion expressed in Sf9 cell membranes. The fraction of β$_2$AR in the K$_{i\ high}$ state for the β$_2$AR-Gαs peptide fusion is 0.68. e, Same view as (b) but with metarhodopsin II structure and the C-terminal peptide removed. f, Comparison of G⟨sRas domains of the transducin peptide aligned GTPγS bound Gs structure and the nucleotide-free Gs heterotrimer of the β$_2$AR-Gs complex.

Clues to the initial stages of complex formation may come from the recent active state structures of rhodopsin. FIGS. 12a and b compare the active-state structure of β₂AR in the β₂AR-Gs complex with the recent structure of metarhodopsin II bound to the transducin peptide. The conformational changes in TM5 and TM6 are smaller in metarhodopsin II, and the position of the carboxyl terminal alpha helix of transducin is tilted by approximately 30° relative to the position of the homologous region of Gs. These may represent fundamental differences in the receptor-G protein interactions between these two proteins, but given the strong conservation of the G-protein binding pocket, the changes more likely reflect the extensive contacts formed with the intact G protein. The position of the transducin peptide in metarhodopsin II may represent the initial interaction between a GDP-bound G protein and a GPCR. We have attempted to reproduce a similar complex between the β₂AR and a synthetic peptide representing the carboxyl terminal 20 amino acids of Gs, but did not observe any effect of this peptide on receptor function, possibly due to the solubility and behavior of the peptide in solution. However, when the carboxyl terminal 20 amino acids of Gs are fused to the carboxyl terminus of the β₂AR (FIG. 12c), we observe a 27-fold increase in agonist affinity (FIG. 12d). This effect is only 3.5-fold smaller than the effect we observe on agonist binding affinity in the β₂AR-Gs complex, and demonstrates that there is a functional interaction between the peptide and receptor that may represent an initial stage in β₂AR-Gs complex formation. FIG. 12 e, f presents a possible sequence of interactions of β₂AR and Gs when forming the nucleotide free complex. The initial interaction of the β₂AR with Gs would require an outward movement of the carboxyl terminus of the α5-helix away from the β6-strand to permit interactions with the β₂AR similar to those observed in metarhodopsin II. The dynamic character of the carboxyl terminal end of α5 is supported by deuterium exchange studies and the relatively loose packing of α5 with the rest of GαsRas in the structure of Gαs alone. The subsequent formation of more extensive interactions between the β₂AR ICL 2 and the amino terminus of Gαs requires a rotation of Gαs-Ras relative to the receptor and would be associated with further conformational changes in both β₂AR and GαsRas (FIG. 12f). This binding model is in agreement with deuterium exchange experiments.

The coordinates and structure factors for the β₂AR-Gs complex are deposited in the Protein Data Bank as accession number 3SN6, which is incorporated by reference herein.

TABLE 1

Potential intermolecular interaction within the R:G interface

| | atom in β2AR | atom in Gsα | | distance (Å) |
|---|---|---|---|---|
| TM3 | [ ARG 131 CG ] | [ TYR 391 CE2 ] | | 3.6 |
| | [ ALA 134 O ] | [ HIS 387 ND1 ] | | 3.1 |
| | [ ALA 134 CB ] | [ HIS 387 ND1 ] | | 3.8 |
| | [ ALA 135 CB ] | [ HIS 387 CG ] | | 3.8 |
| | [ ILE 135 O ] | [ GLN 384 NE2 ] | | 2.9 |
| | [ ILE 135 CD1 ] | [ LEU 388 CD1 ] | α5 | 3.5 |
| | [ ILE 135 CD1 ] | [ LEU 393 CD1 ] | | 3.5 |
| | [ THR 136 O ] | [ ARG 380 NH2 ] | | 3.0 |
| IL2 | [ PRO 138 O ] | [ ILE 383 CD1 ] | | 3.4 |
| | [ PRO 138 CG ] | [ GLN 384 CG ] | | 3.3 |
| | [ PHE 139 CD2 ] | [ HIS 41 NE2 ] | −β1 | 3.6 |
| | [ PHE 139 CB ] | [ VAL 217 CG2 ] | −α4 | 3.7 |
| | [ PHE 139 CE1 ] | [ PHE 376 CZ ] | | 3.3 |
| | [ PHE 139 CZ ] | [ CYS 379 C ] | | 3.9 |
| | [ PHE 139 CZ ] | [ ARG 380 N ] | α5 | 3.2 |
| | [ TYR 141 CD2 ] | [ HIS 387 NE2 ] | | 3.9 |
| | [ GLN 142 OE1 ] | [ HIS 387 NE2 ] | | 3.5 |
| | [ SER 143 OG ] | [ ALA 39 CB ] | −αN | 3.6 |
| TM5 | [ VAL 222 CG1 ] | [ LEU 393 CD1 ] | | 3.7 |
| | [ GLU 225 OE2 ] | [ GLN 384 NE2 ] | | 3.0 |
| | [ ALA 226 CA ] | [ LEU 388 CD2 ] | | 3.6 |
| | [ ALA 226 CB ] | [ LEU 393 O ] | | 3.8 |
| | [ GLN 229 NE2 ] | [ ASP 381 OD1 ] | | 3.6 |
| | [ GLN 229 NE2 ] | [ GLN 384 OE1 ] | α5 | 2.8 |
| | [ GLN 229 OE1 ] | [ ARG 385 NE ] | | 3.4 |
| | [ GLN 229 CG ] | [ LEU 388 CD2 ] | | 3.9 |
| | [ LEU 230 CG ] | [ LEU 394 CD1 ] | | 3.5 |
| | [ LYS 232 NZ ] | [ ASP 381 OD1 ] | | 3.1 |
| | [ ILE 233 CD1 ] | [ TYR 358 OH ] | −β6 | 3.4 |
| | [ ILE 233 CG1 ] | [ ARG 385 NH1 ] | −α5 | 3.5 |
| | [ ARG 239 NE ] | [ THR 350 OG1 ] | −α4 | 3.5 |
| TM6 | [ ALA 271 CB ] | [ LEU 393 O ] | | 3.0 |
| | [ THR 274 CG2 ] | [ GLU 392 O ] | α5 | 3.4 |
| | [ THR 274 OG1 ] | [ LEU 393 CD2 ] | | 3.3 |
| | [ LEU 275 CD2 ] | [ LEU 393 CD2 ] | | 3.6 |

TABLE 2

Data collection and refinement statistics

Data collection*

| | |
|---|---|
| Number of crystals | 20 |
| Space group | P 2$_1$ |
| Cell dimensions | |
| a, b, c (Å) | 119.3, 64.6, 131.2 |
| α, β, γ (°) | 90.0, 91.7, 90.0 |
| Resolution (Å) | 41-3.2 (3.26-3.20) |
| R$_{merge}$ (%) | 15.6 (553) |
| <I>/<σI> | 10.8 (1.8) |
| Completeness (%) | 91.2 (53.9) |
| Redundancy | 6.5 (5.0) |
| Refinement | |
| Resolution (Å) | 41-3.2 |
| No. reflections | 31075 (1557 in test set) |
| R$_{work}$/R$_{free}$ (%) | 22.5/27.7 |
| No. atoms | 10277 |
| No. protein residues | 1318 |
| Anisotropic B tensor | B$_{11}$ = −7.0/B$_{22}$ = 4.7/B$_{33}$ = 2.3/B$_{13}$ = 2.1 |
| Unmodelled sequences* | |
| β$_2$ adrenergic receptor | 29$^b$, 176-178, 240-264, 342-365 |
| G$_s$α, ras domain | 1-8, 60-88, 203-204, 256-262 |
| G$_s$γ | 1-4, 63-68 |
| T4 lysozyme | 161$^c$ |
| Average B-factors (Å$^2$) | |
| β$_2$ adrenergic receptor | 133.5 |
| G$_s$α, ras domain | 82.8 |
| G$_s$α, helical domain | 123.0 |
| G$_s$β | 64.2 |
| G$_s$γ | 85.2 |
| Nanobody 35 | 60.7 |
| T4 lysozyme | 113.7 |
| R.m.s. deviation from ideality | |
| Bond length (Å) | 0.007 |
| Bond angles (°) | 0.72 |
| Ramachandran statistics$^d$ | |
| Favored regions (%) | 95.8 |
| Allowed regions (%) | 4.2 |
| Outliers (%) | 0 |

*Highest shell statistics are in parentheses.
$^a$These regions were omitted from the model due to poorly resolved electron density. Unmodelled purification tags are not included in these residue ranges.
$^b$Residues 1-28 of the β2AR were omitted from the construct and T4L was fused to the amino terminus of transmembrane helix 1 to facilitate crystallization.
$^c$Residue 1 of T4L was omitted from the construct
$^d$As defined by MolProbity$^{38}$.

TABLE 3

Data collection statistics by resolution shell

| Resolution Shell (Å) | <I>/<σI> | R$_{merge}$ (%) | Completeness (%) |
|---|---|---|---|
| 41-8.67 | 18.8 | 06.6 | 97.1 |
| 8.67-6.89 | 16.9 | 09.2 | 99.5 |
| 6.89-6.02 | 14.4 | 13.0 | 99.7 |
| 6.02-5.47 | 12.8 | 16.7 | 99.9 |
| 5.47-5.08 | 13.4 | 15.9 | 99.9 |
| 5.08-4.78 | 13.4 | 16.9 | 99.8 |
| 4.78-4.54 | 12.2 | 18.2 | 99.6 |
| 4.54-4.34 | 11.6 | 20.1 | 99.8 |
| 4.34-4.18 | 9.5 | 22.9 | 99.4 |
| 4.18-4.03 | 7.7 | 26.2 | 99.1 |
| 4.03-3.91 | 6.6 | 27.9 | 98.7 |
| 3.91-3.79 | 5.3 | 30.2 | 98.7 |
| 3.79-3.69 | 3.8 | 36.6 | 96.7 |
| 3.69-3.60 | 4.6 | 36.9 | 94.6 |
| 3.60-3.52 | 2.3 | 45.7 | 90.3 |
| 3.52-3.45 | 2.2 | 47.9 | 86.3 |
| 3.45-3.38 | 2.4 | 45.6 | 80.5 |
| 3.38-3.31 | 2.1 | 47.3 | 69 |
| 3.31-3.26 | 2.2 | 49.8 | 59.4 |
| 3.26-3.20 | 1.8 | 55.3 | 53.9 |
| Overall | 10.8 | 15.6 | 91.2 |

Materials and Methods III

Generation of N-T4L Fused β2AR Constructs

Figure 22:
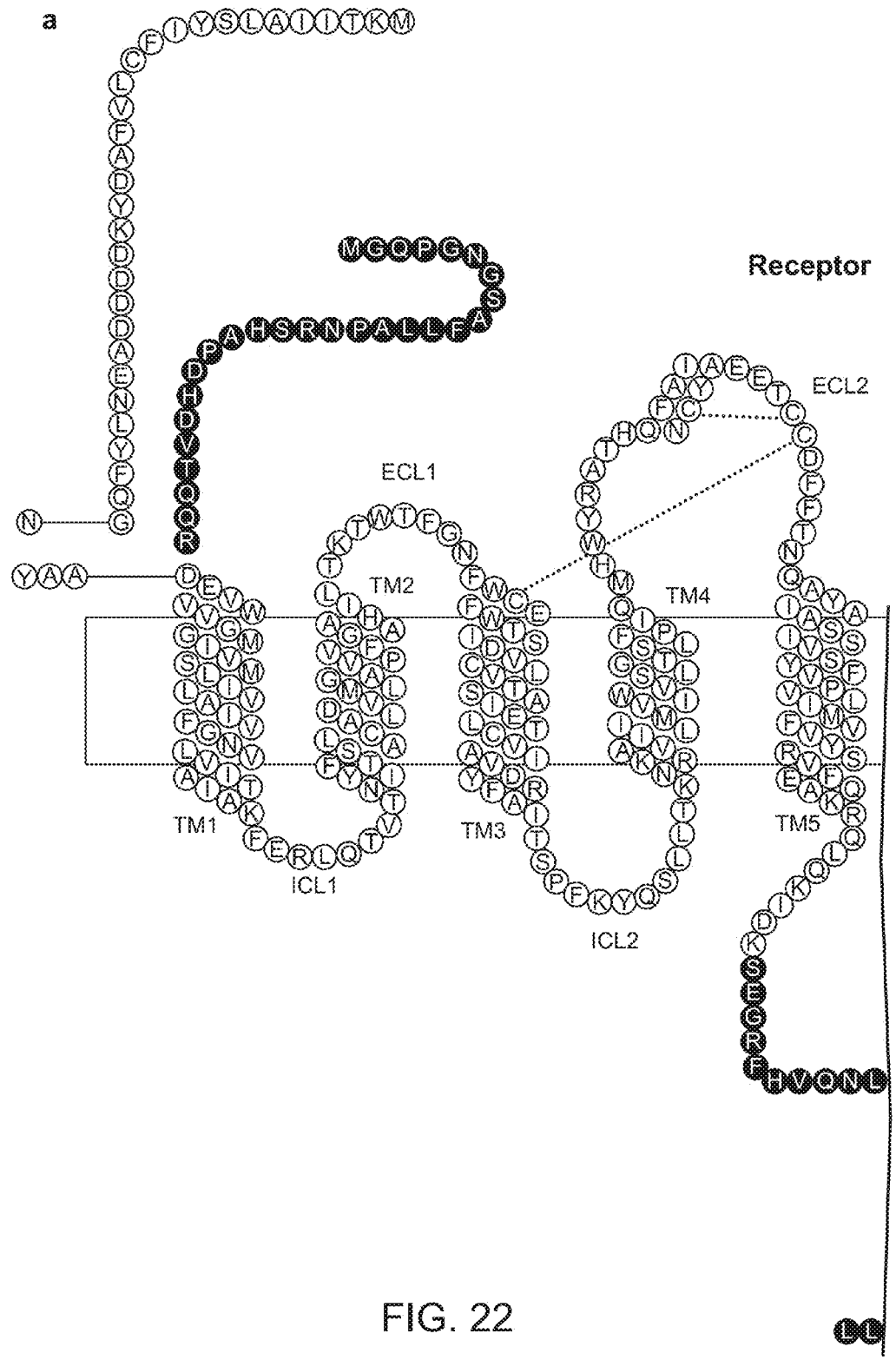
FIG. 22. a. shows a schematic diagram of T4L-β$_2$AR-ΔICL3 fusion protein used for crystallography, in including the β$_2$AR residues, the wild type β$_2$AR sequence, the HA signal peptide, the FLAG tag, the TEV recognition site the M96T, M98T mutations, the cysteines involved in disulfide bonds, disulfide bond linkages, the N187E mutation, and the 2-Ala linker. b. shows a chematic diagram of all of the T4L-β$_2$AR-ΔICL3 constructs that were generated and evaluated for expression of functional receptor protein in insect cells. SEQ ID NOS: 18-29.

The human β$_2$AR in the pFastbac1 Sf9 expression vector truncated at amino acid 365 in the cytoplasmic tail (β$_2$AR365) was used as the starting template for generating the N-T4L fused β$_2$AR constructs. The HA signal peptide followed by FLAG epitope tag and tobacco etch virus (TEV) protease recognition sequence were added to the N-terminus of the receptor to facilitate expression and purification. A point mutation of N187E was also introduced in the second extracellular loop to remove a glycosylation site (FIG. 22).

DNA cassettes encoding two different versions of T4L lysozyme (full length or with truncated C-terminus) with different numbers of additional alanines attached to the C-terminus were generated and amplified by PCR using the original β$_2$AR-T4L $^3$ as the template and synthetic oligonucleotides as primers. These different cassettes were inserted into the β$_2$AR365 construct between the end of the TEV protease recognition sequence and Asp29, Glu30 or Val31 of the receptor as shown in (FIG. 22) by using the Quickchange multi protocol (Stratagene). Two point mutations M96T, M98T were also introduced into the β$_2$AR sequence. Residues from Ser235 to Lys263 in the third intracellular loop were deleted with the Quickchange multi protocol using synthetic oligonucleotides as mutation primers. All the constructs were confirmed by DNA sequencing. The protein sequence of T4L-β$_2$AR-Δ-ICL3 is shown below:

(SEQ ID NO: 17)
*MKTIIALSYIFCLVFA*DYKDDDDA`ENLYFQ*G`NIFEMLRIDEGLRLKIYK

DTEGYYTIGIGHLLTKSPSLNAAKSELDKAIGRNTNGVITKDEAEKLFNQ

DVDAAVRGILRNAKLKPVYDSLDAVRRAALINMVFQMGETGVAGFTNSLR

MLQQKRWDEAAVNLAKSRWYNQTPNRAKRVITTFRTGTWDAYAADEVWVV

GMGIVMSLIVLAIVFGNVLVITAIAKFERLQTVTNYFITSLACADLVMGL

AVVPFGAAHILTKTWTFGNFWCEFWTSIDVLCVTASIETLCVIAVDRYFA

ITSPFKYQSLLTKNKARVIILMVWIVSGLTSFLPIQMHWYRATHQEAINC

YAEETCCDFFTNQAYAIASSIVSFYVPLVIMVFVYSRVFQEAKROLOKID

KFCLKEHKALKTLGIIMGTFTLCWLPFFIVNIVHVIQDNLIRKEVYILLN

WIGYVNSGFNPLIYCRSPDFRIAFQELLCLRRSSLKAYGNGYSSNGNTGE

QSG.

The HA signal peptide is shown in italic letters; the FLAG epitope tag is shown in letters with underscore; the TEV recognition sequence is marked with a box and the cleavage site is shown with an asterisk; the full length T4L is shown in bold; the β₂AR sequence from Asp29 to Gly365 excluding Ser235 to K263 is shown in bold underline, the 2-Ala linker is underlined).

The entire T4L-β₂AR-Δ-ICL3 gene described above was further cloned into the Best-Bac Sf9 expression vector pv11393 (expression systems) using the restriction enzyme digestion site XbaI and EcoRI. This version of T4L-β₂AR-Δ-ICL3 construct was also confirmed by DNA sequencing.

Whole Cell Binding to Assess the Expression Yield of Each Construct.

Recombinant baculovirus was made from the pFastbac1 Sf9 expression vector for each of the constructs illustrated in FIG. 22 using the Invitrogen protocol. Sf9 cells at a density of 4 million/ml were infected with second passage virus at different ratios of virus stock to cell culture (1:20, 1:50, and 1:100). After 48 hours, 5 μl of the infected cells were incubated with 10 nM of [³H]-dihydroalprenolol (DHA) in 500 μl of binding buffer (75 mM Tris, 12.5 mM MgCl2, 1 mM EDTA, pH 7.4, supplemented with 5 mg/ml BSA). Cells were harvested and washed with cold binding buffer using a Brandel harvester. Bound [³H]DHA was measured with scintillation counter (Beckman). Non-specific binding of [³H]DHA was assessed by including 10 μM of alprenolol (Sigma) in the same binding reaction. The expression level of each construct was determined using the specific activity of the bound [³H] DHA. Each experiment was performed in triplicate.

Saturation and Competition Binding Assays.

Membranes from Sf9 cells expressing either wild-type β2AR or T4L-β₂AR-Δ-ICL3 were prepared based on a previously describe protocol[12]. In each reaction for the saturation binding assay, membranes containing approximately 0.2 pmol receptor were incubated with concentrations of [³H] DHA ranging from 5 pM to 10 nM in 500 μl of buffer (75 mM Tris, 12.5 mM MgCl2, 1 mM EDTA, pH 7.4, supplemented with 0.5 mg/ml BSA) at room temperature with shaking at 230 rpm for 1 hour. Membranes were isolated from free [³H]DHA using a Brandel harvester and washed three times with cold buffer. The amount of receptor bound [³H]DHA was measured using a scintillation counter (Beckman). Non-specific binding of the [³H]DHA in each reaction was assessed by including 1 μM alprenolol (Sigma) in the same reaction. In each reaction for the competition binding assay, membrane containing approximately 0.2 pmol receptor was incubated with 1 nM [³H]DHA and different concentrations of (-)-isoproterenol (Sigma) ranging from 1 nM to 1 mM. Membranes were harvested and washed three times with cold buffer. The bound [³H]DHA was counted as described above. Non-specific [³H]DHA was assessed by replacing (-)-isoproterenol with 1 μM alprenolol. All the binding data was analyzed by non-linear regression method using Graphpad Prism. Each experiment was performed in triplicate.

Expression and Purification of T4L-β₂AR-Δ-ICL3 from Baculovirus-Infected Sf9 Cells Recombinant baculovirus was made from pv11393-T4L-β₂AR-Δ-ICL3 using Best-Bac expression system, as described by the system protocol (Expression Systems). T4L-β₂AR-Δ-ICL3 was expressed by infecting Sf9 cells at a density of 4 million/ml with a second passage baculovirus stock at a virus to cell ratio of 1:50. 1 μM of the antagonist alprenolol was included to enhance the receptor stability and yield. The infected cells were harvested after 48 hs of incubation at 27° C.

Cell pellets were lysed by vigorous stirring in lysis buffer (10 mM TRIS-Cl pH 7.5, 2 mM EDTA, 10 ml of buffer per gram of cell pellet) supplemented with protease inhibitor Leupeptin (2.5 μg/ml final concentration, Sigma) and Benzamindine (160 μg/ml final concentration, Sigma) for 15 minutes. The T4L-β₂AR-Δ-ICL3 protein was extracted from the cell membrane by dounce homogenization in solubilization buffer (100 mM NaCl, 20 mM TRIS-Cl, pH 7.5, 1% Dodecylmaltoside) supplemented with Leupeptin and Benzamindine (2.5 μg/ml and 160 μg/ml final concentration, respectively). 10 ml of solubilization buffer was used for each gram of cell pellet. The Dodecylmaltoside (DDM)-solubilized T4L-β₂AR-Δ-ICL3 bearing the FLAG epitope was then purified by M1 antibody affinity chromatography (Sigma). Extensive washing using HLS buffer (100 mM NaCl, 20 mM HEPES pH 7.5, 0.1% DDM) was performed to get rid of alprenolol. The protein was then eluted with HLS buffer supplemented with 5 mM EDTA, 200 μg/ml free FLAG peptide and a saturating concentration of cholesterol hemisuccinate.

The eluted T4L-β₂AR-Δ-ICL3 was further purified by affinity chromatography using alprenolol-Sepharose as previously described [3] in order to isolate functional T4L-β₂AR-Δ-ICL3 from non-functional protein. HHS buffer (350 mM NaCl, 20 mM HEPES pH 7.5, 0.1% DDM) supplemented with 300 μM alprenolol and a saturating concentration of cholesterol hemisuccinate was used to elute the protein. The eluted T4L-β₂AR-Δ-ICL3 bound with alprenolol was then re-applied to M1 resin, allowing exchanging alprenolol with carazolol in HHS buffer supplemented with 30 nM carazolol. T4L-β₂AR-Δ-ICL3 bound with carazolol was then eluted from M1 resin with HHS buffer supplemented with 5 mM EDTA, 200 μg/ml free FLAG peptide and saturating concentration of cholesterol hemisuccinate. The FLAG epitope tag of T4L-β₂AR-Δ-ICL3 was removed by the treatment of tobacco etch virus (TEV) protease (invitrogen) for 3 hs at room temperature or overnight at 4° C. The untagged T4L-β₂AR-Δ-ICL3-cazazolol complex was then further purified by chromatography (SEC) using S200 column (GE healthcare) equilibrated in 100 mM NaCl, 10 mM HEPES pH 7.5, 0.1% DDM and 1 nM carazolol. The same buffer was used as the running buffer for SEC. The purity of the final T4L-β₂AR-ΔICL3 is more than 90% according to the result of SDS-PAGE electrophoresis.

Crystallization of the T4L-β₂AR-ΔICL3-Carazolo Complex

The purified T4L-β₂AR-Δ-ICL3-carazolol complex was concentrated to a final concentration of 60 mg/ml using centricon Vivaspin (GE healthcare). The complex was crystallized using the lipid cubic phase (LCP) method as previously described[3]. The protein complex was mixed with lipid moloolein with a 1:1.5 mass ratio at room temperature. 0.03 μl of the protein-lipid mixture drop was deposited in each well of a 96-well glass sandwich plate (Molecular Dimensions). The drop was then overlaid with 0.65 μl of precipitant and the well was sealed by glass coverslip. By using this method, the T4L-β₂AR-Δ-ICL3-carazolol complex was crystallized in 37% PEG300 (v/v), 0.1M Bis-Tris propane, pH 6.5, 0.1 M ammonium phosphate after 2 days of incubation in 20° C.

Data Collection and Structure Determination

The crystals were harvested and frozen in liquid nitrogen directly without using additional cryo-protectant. Diffraction data from 15 different crystals was collected using the GM/CA-CAT minibeam at 23-ID-D, Advance Photon Source, Argonne National Labs. The data was processed with HKL2000 and the structure was solved by molecular replacement using Molrep. Further model rebuilding was performed by using coot and the structure was refined with Phenix. The validation of the final structural model was performed using Molprobity. Data processing and refinement statistics are shown in Table 4.

Results III

T4 lysozyme was fused to the N-terminus of the $\beta_2$ adrenergic receptor ($\beta_2$AR), a G-protein coupled receptor (GPCR) for catecholamines. The N-terminally fused T4L is sufficiently rigid relative to the receptor to facilitate crystallogenesis without thermostabilizing mutations or the use of a stabilizing antibody, G protein, or protein fused to the 3rd intracellular loop. This approach adds to the protein engineering strategies that enable crystallographic studies of GPCRs alone or in complex with a signaling partner.

The N terminus of the $\beta_2$AR was replaced with T4 lysozyme to produce a T4L-GPCR fusion. To have a T4L-$\beta_2$AR construct suitable for crystallization, the link between T4L and the receptor should be relatively short and rigid, yet not interfere with receptor function. Several different constructs were generated and examined for expression levels and binding properties (FIG. 22). In an effort to generate a rigid interaction between T4L and the $\beta_2$AR, we removed the relatively flexible C-terminus of the T4L and attempted to fuse the remaining C terminal helix of T4L with the extracellular end of TM1 of the $\beta_2$AR. None of these constructs gave sufficient amounts of functional receptor.

In the second approach, we fused the carboxyl terminus of T4L to D29, the first amino acid of the extracellular helical extension of TM 1. Four constructs were generated and examined: direct fusion of T4L to D29, and the inclusion of 1-3 Ala residues between T4L and the $\beta_2$AR (FIG. 22). The highest level of expression was obtained from the fusion with a 2-Ala linker. The fusion protein had normal pharmacology and G protein coupling. To improve expression, two additional point mutations M96T and M98T were made in the $\beta_2$AR component of the fusion protein. We have previously observed that mutation of these residues, which are located in the first extracellular loop and face away from the protein, had no effect on receptor function, but enhanced expression by up to two-fold. We were able to produce 1.5 mg of pure, functional protein from 1 liter of Sf9 cells.

Figure 24:
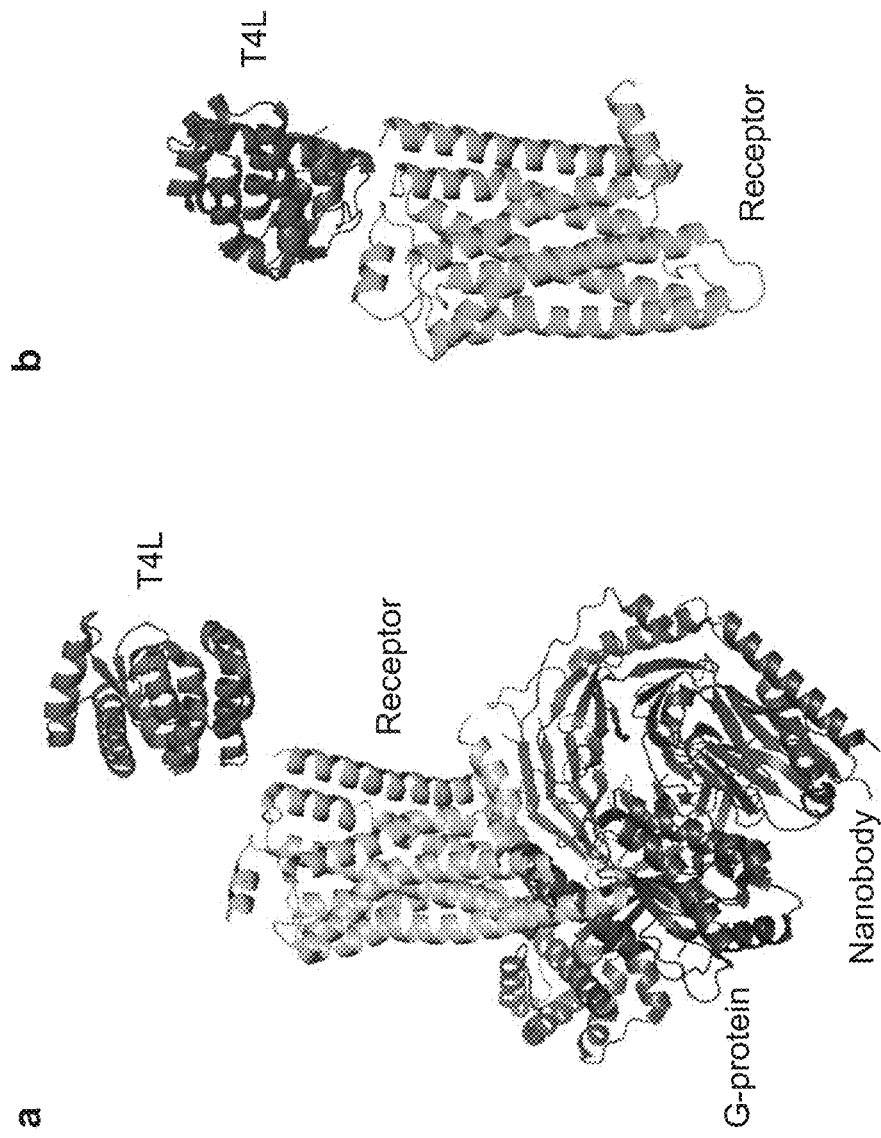
FIG. 24. a. The crystal structure of the β₂AR-Gs complex. The T4L, β₂AR and the G-protein heterotrimer are shown in grey, as is the stabilizing nanobody. There is no packing interaction between the T4L and its fused β₂AR. b. The crystal structure of T4L-β₂AR-ΔICL3. The T4L is shown in red and its fused β₂AR-ΔICL3 is shown. In contrast to the β₂AR-Gs complex structure, there are packing interactions between the T4L and its fused receptor β₂AR-ΔICL3.

This version of T4L-$\beta_2$AR was recently used to obtain the crystal structure of the $\beta_2$AR-Gs complex. However, in this structure most of the lattice contacts in this crystal are mediated by Gs, and the N terminal fused T4L does not pack against the extracellular surface of its fused $\beta_2$AR (FIG. 24). The lack of interactions between T4L and the extracellular surface of the $\beta_2$AR in the $\beta_2$AR-Gs complex suggested that T4L fused to the N terminus of the $\beta_2$AR might not be sufficiently constrained to facilitate crystallogenesis in the absence of the cytoplasmic G protein. The amino terminal T4L facilitated crystallogenesis in the absence of a soluble protein bound or fused to the third intracellular loop. Additional modifications were made to minimize unstructured sequence in the third intracellular loop and carboxyl terminus (FIG. 22). The C-terminus was truncated after amino acid 365. The $3^{rd}$ intracellular loop (ICL3) of $\beta_2$AR is another flexible region and it is subject to proteolysis. This loop was truncated in the fusion protein by removing residues 235 to 263. The final construct T4L-$\beta_2$AR-$\Delta$-ICL3 is illustrated in FIG. 22.

Figure 25:
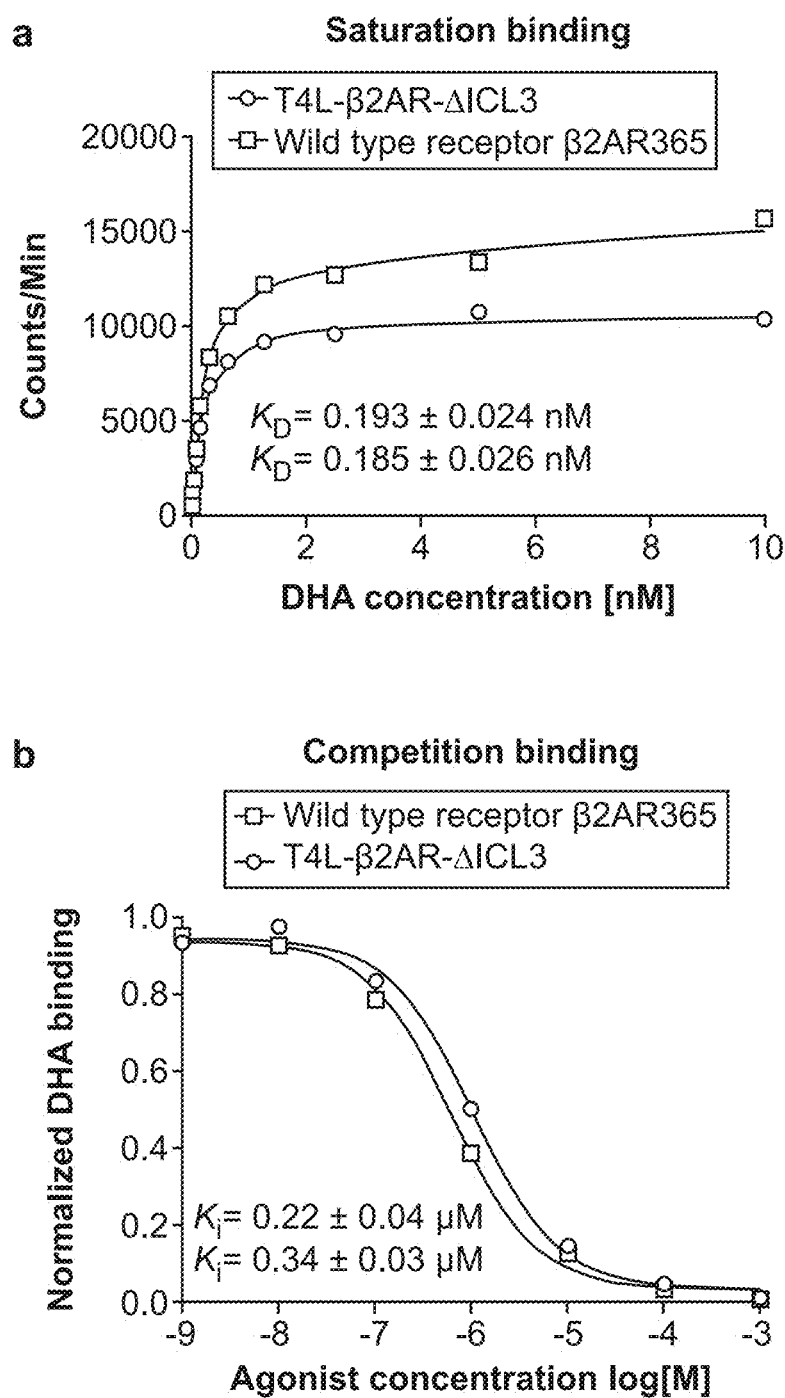
FIG. 25. a. Saturation binding curves for antagonist dihydroalprenolol (DHA) binding to T4L-β₂AR-ΔICL3 and the wild type β₂AR365. b. Competition binding curves for agonist isopreterenol binding to T4L-β₂AR-ΔICL3 and the wild type β₂AR365.

To determine the functional integrity of T4L-$\beta_2$AR-$\Delta$-ICL3, agonist and antagonist binding affinities were determined. The ligand binding pocket is formed by amino acids from four transmembrane domains and is therefore very sensitive to any perturbation of the receptor structure. T4L-$\beta_2$AR-$\Delta$-ICL3 exhibits ligand binding affinities for the antagonist [3H]-Dihydroalprenolol and the agonist isopreterenol that are comparable to those of the wild type receptor (FIG. 25).

Figure 23:
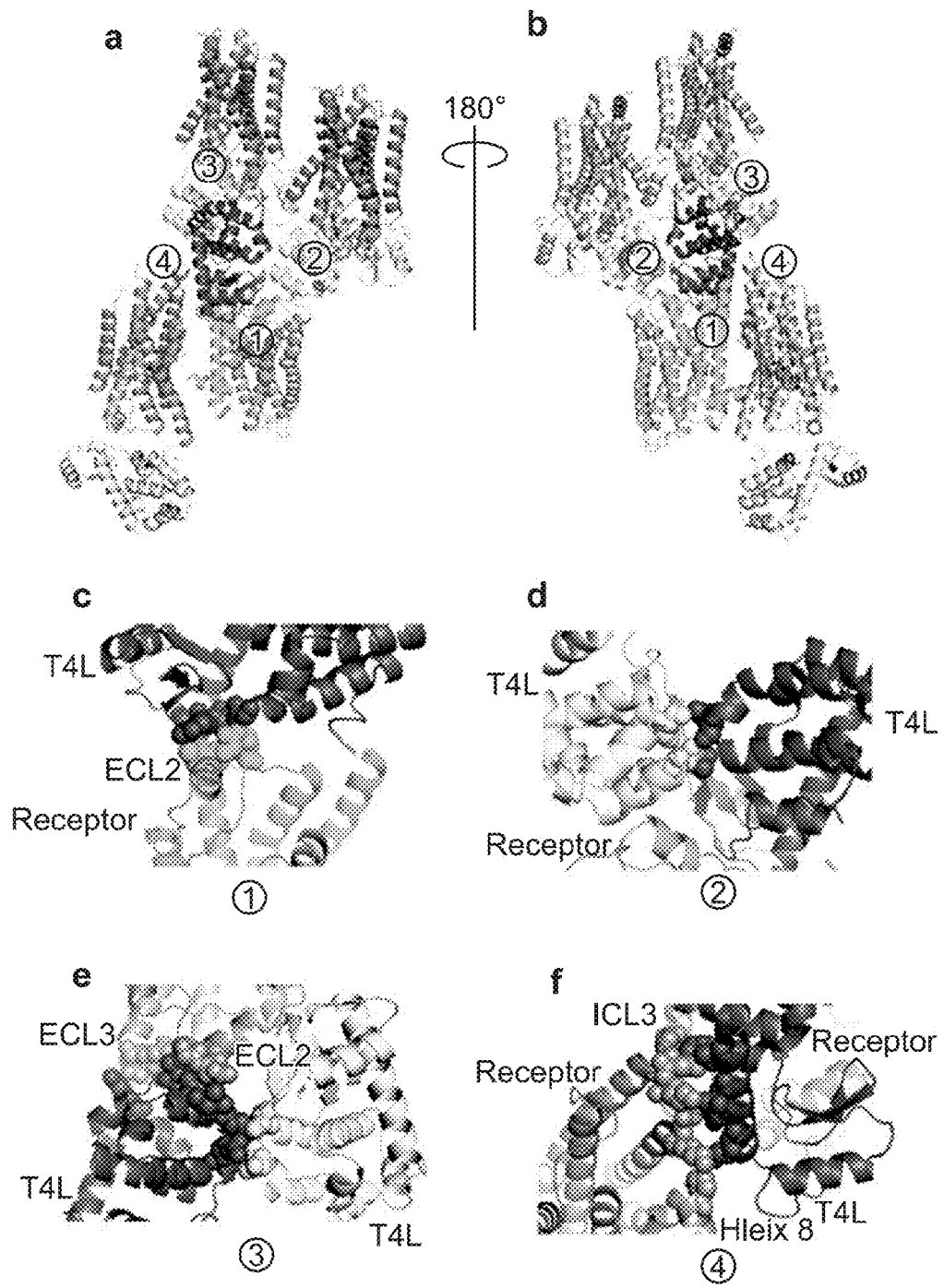
FIG. 23. a, b. Packing interactions mediated by T4L. Each T4L packs against three adjacent T4L-β$_2$AR-ΔICL3 molecules and is involved in 4 packing interactions. The T4L and β$_2$AR-Δ-ICL3 from the reference molecule are shown. The T4L and β$_2$AR-Δ-ICL3 from the three adjacent molecules are shown. c-f. Close-up few of packing interactions 1-4. The residues involved in interactions are shown as spheres c. In interaction 1 the reference T4L packs against ECL2 of its fused β₂AR-Δ-ICL3. d. In interaction 2 the reference T4L packs against T4L of an adjacent T4L-β₂AR-Δ-ICL3. e. In interaction 3 the reference T4L packs against T4L, ECL2 and ECL3 of a second adjacent T4L-β₂AR-Δ-ICL3. f. In interaction 4 the reference T4L packs against ICL3 and helix 8 of a third T4L-β₂AR-Δ-ICL3.
Figure 26:
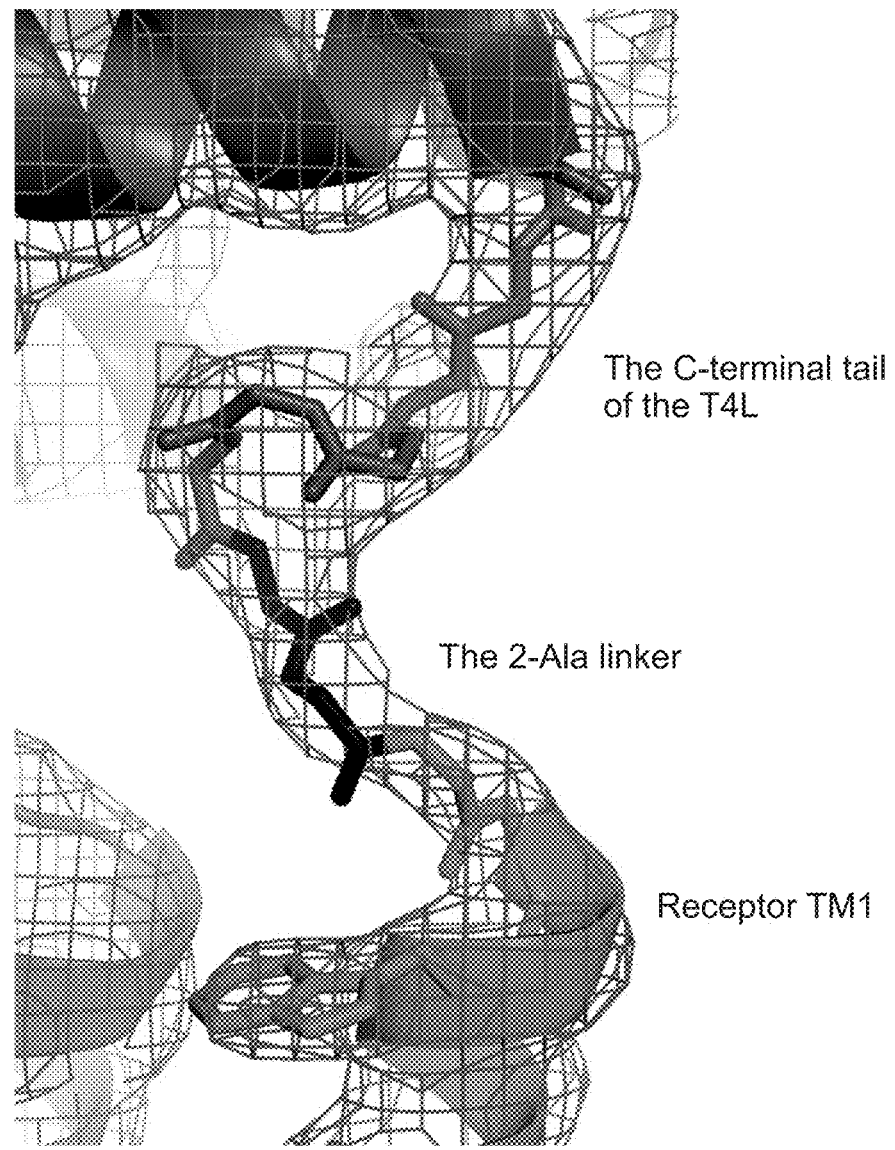
FIG. 26. 2Fo-Fc map around the 2-Ala linker between T4L and the β₂AR. The main chain of the fusion junction is shown in sticks. The electron density is shown in green mesh (1σ). The T4L and β₂AR-ΔICL3 are shown in grey, as is the 2-Ala linker.

Purified T4L-$\beta_2$AR-$\Delta$-ICL3 bound to the inverse agonist carazolol crystallized as small rods in lipid cubic phase (37% PEG300 (v/v), 0.1M Bis-Tris propane, pH 6.5, 0.1 M ammonium phosphate). Crystals diffracted to a resolution of 3.3 Å; however, due to radiation damage, our dataset was limited to 4.0 (Table 4). Nevertheless, the dataset allowed us to solve the structure by molecular replacement. The interaction between the $\beta_2$AR and T4L is sufficiently rigid to detect electron density for the 2 Ala link between these two proteins (FIG. 26). This link was not detectable in the electron density map of the $\beta_2$AR-Gs structure (FIG. 24). In the T4L-$\beta_2$AR-$\Delta$-ICL3 crystal lattice, the packing interactions are primarily mediated by T4L and there are no contacts between adjacent receptors (FIG. 23), indicating the important role of the T4L in facilitating GPCR crystallization. Each T4L has four packing interactions: 1-against ECL1 and ECL2 of its fused $\beta_2$AR-$\Delta$-ICL3, 2-against T4L of one adjacent T4L-$\beta_2$AR-$\Delta$-ICL3, 3-against T4L, ECL2 and ECL3 of a second T4L-$\beta_2$AR-$\Delta$-ICL3, and 4-against ICL3 and Helix 8 of a third T4L-$\beta_2$AR-$\Delta$-ICL3 (FIG. 23).

The structures of the $\beta_2$AR in T4L-$\beta_2$AR-$\Delta$-ICL3 and $\beta$2AR-T4L (pdb 2RH1) are very similar to each other (FIG. 27), with an overall root mean square deviation of 0.48 Å. Only minor differences can be observed in these two structures, presumably due to different crystal packing patterns. The similarity of the structures determined independently through different strategies further validates the fusion protein approach, demonstrating that structural distortions due to protein engineering or crystal packing are unlikely.

Figure 27:
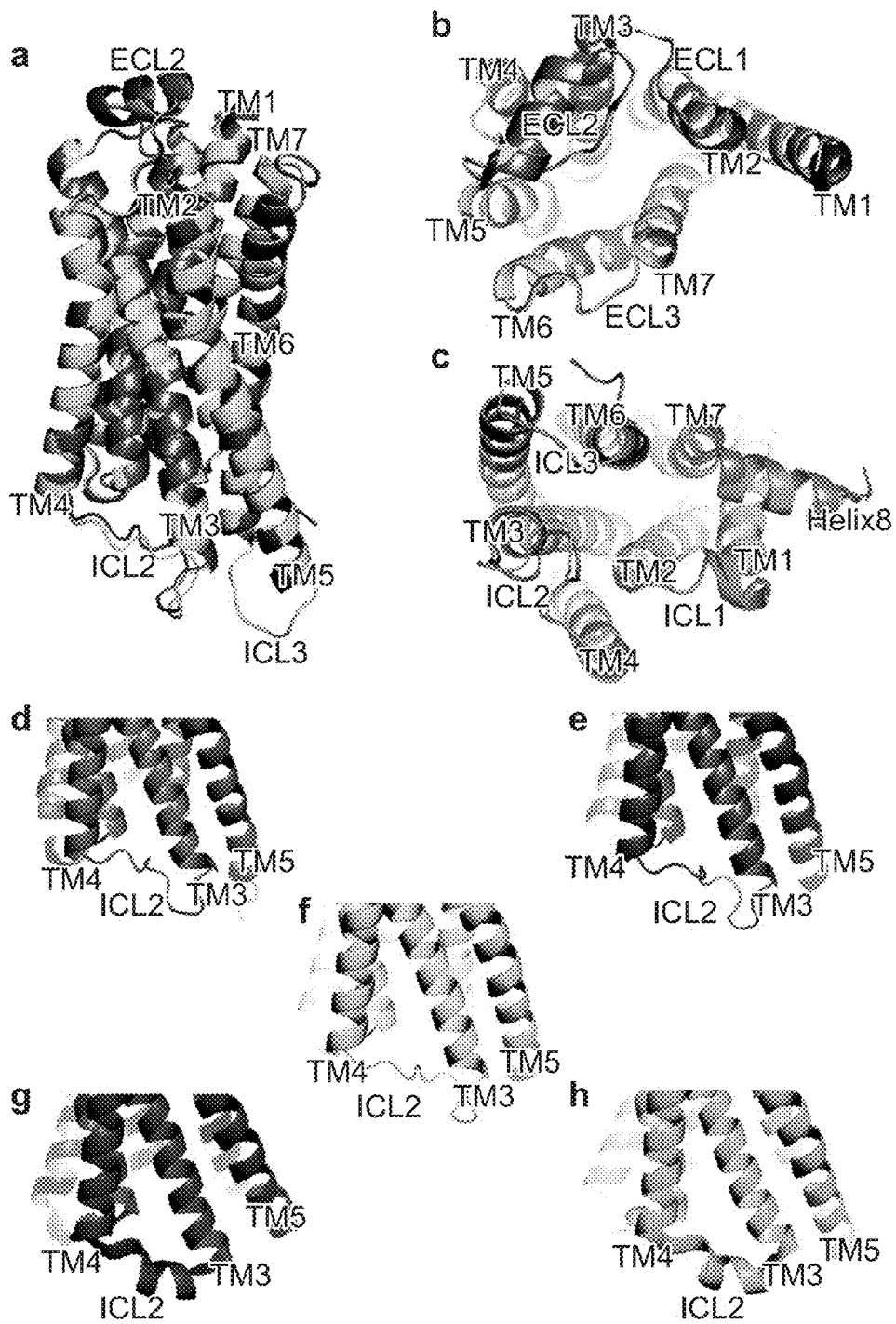
FIG. 27. a. The superposed structures of the T4L-β₂AR-ΔICL3 and the β₂AR-T4L (pdb 2RH1). The T4L-β₂AR-ΔICL3 and the β₂AR-T4L are shown in grey. b. The extracellular side view of the superposed structures. c. The intracellular side view of the superposed structures. d. ICL2 in the β₂AR-Fab5 structure (pdb 2R4R). e. ICL2 in the β₂AR-T4L structure (pdb 2RH1). f. ICL2 in the T4L-β₂AR-ΔICL3 structure. g. ICL2 in the structure of β₂AR stabilized by Nb80 (pdb 3P0G) and h. ICL2 in the β₂AR-Gs structure (pdb 3SN6)

Of interest, ICL2 in the two inactive structures of $\beta_2$AR-Fab5 and $\beta_2$AR-T4L is in an extended loop while it is an alpha helix in both active structures: the $\beta_2$AR-Gs complex and the $\beta_2$AR stabilized by Nb80. In both of the inactive structures ($\beta_2$AR-Fab5 and $\beta_2$AR-T4L), ICL2 participates in lattice contacts that may influence its conformation. However, in the T4L-$\beta$2AR-$\Delta$-ICL3 structure ICL2 is not involved in packing interactions, yet is an extended loop is nearly identical to that observed in the other inactive state $\beta_2$AR structures (FIG. 27). Thus, this extended loop structure may reflect an inactive state.

In conclusion, fusion of T4L to the amino terminus of a GPCR can facilitate crystallogenesis. This approach can also facilitate the formation of crystals of a GPCR in complex with a cytoplasmic signaling protein.

Figure 28:
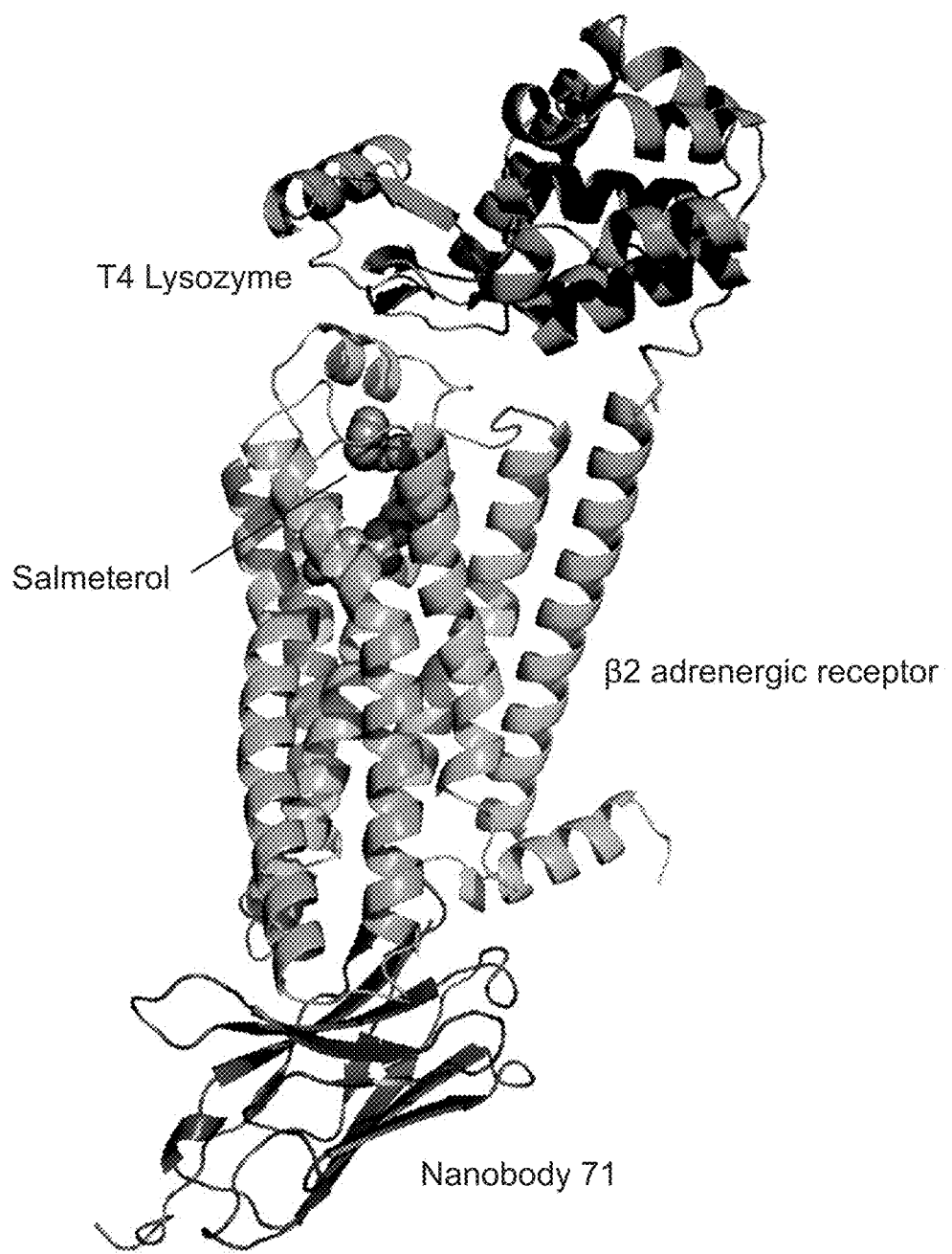
FIG. 28. Shows a model of β2AR bound to salmeterol, a partial agonist that is used to treat asthma. The partial-active state is stabilized by nanobody 71.

FIG. 28 illustrates shows the structure of T4L-$\beta$2AR fusion bound to salmeterol, a partial agonist used to treat asthma. In this structure, the partial-active state is stabilized by a nanobody (nanobody 71). This structure was obtained using similar methods to those described above.

TABLE 4

| Data collection | |
| --- | --- |
| Space group | $P2_12_12_1$ |
| Unit cell dimensions | |
| a, b, c (Å) | 51.4, 71.4, 161.4 |
| Resolution (Å) | 50-4.0 (4.07-4.00)* |
| $R_{merge}$ | 0.199 (0.799) |
| <I/σI> | 8.4 (1.5) |
| Completeness (%) | 84.3 (71.2) |
| Multiplicity | 4.7 (3.7) |
| Refinement | |
| Resolution (Å) | 30-3.99 |
| No. reflections work/free | 4547/691 |
| $R_{work}/R_{free}$ | 0.267/0.293 |
| No. atoms | 3623 |

TABLE 4-continued

Data collection

| Average B values (Å$_2$) | |
|---|---|
| Receptor | 197 |
| T4L | 177 |
| Carazolol | 160 |
| Overall anisotropic B (Å$_2$) | |
| B11/B22/B33 | −21.2/59.3/−38.0 |
| R.m.s deviations | |
| Bond lengths (Å) | 0.004 |
| Bond angles (°) | 0.6764 |

TABLE 4-continued

Data collection

| Ramachandran plot** | |
|---|---|
| % favored | 96.4 |
| allowed | 3.6 |
| generously allowed | 0.0 |
| disallowed | 0.0 |

*High resolution shell in parenthesis.
**As defined by Molprobity
$R_{merge} = \Sigma_{hkl}\Sigma_i|I_i - <I>|/\Sigma_{hkl}\Sigma_i I_i$

---

What is claimed is:

1. A method for designing, selecting and/or optimizing an agonist of a GPCR, comprising:
   (a) employing on a computer the structural coordinates of an active-state GPCR by accessing a file containing atomic coordinates of said GPCR using a computer system that comprises a modeling program to generate a three-dimensional model of said active-state GPCR, wherein said atomic coordinates are produced by subjecting crystals of a GPCR fusion protein to X-ray diffraction analysis, wherein said GPCR fusion protein comprises,
   (i) a G-protein coupled receptor (GPCR); and,
   (ii) an autonomously folding stable domain;
      wherein said autonomously folding stable domain is heterologous to said GPCR and fused to said GPCR within 10 amino acids of the TM1 region of the GPCR; and
      wherein (i) the GPCR fusion protein is complexed with one or more of: a ligand for the GPCR, an antibody and a G protein; and/or (ii) the GCR fusion protein comprises one or more stabilizing amino acid substitutions in addition to the autonomously folding stable domain;
   (b) identifying an active-state GPCR structure characterized by an alpha-helix formation of ICL2 and identifying an agonist binding pocket; and
   (c) determining whether a test compound docks with said binding pocket, wherein a test compound that docks with said binding site is a GPCR activator.

2. The method of claim 1, wherein said autonomously folding stable domain comprises the amino acid sequence of lysozyme or cytochrome b562.

3. The method of claim 1, wherein said GPCR is naturally occurring.

4. The method of claim 1, wherein said GPCR is non-naturally occurring.

5. The method of claim 1, wherein the crystals comprise a G-protein complexed with said GPCR fusion protein.

6. The method of claim 1, wherein the crystals comprises an antibody that is bound to said GPCR.

7. The method of claim 6, wherein said antibody is a nanobody.

8. The method of claim 1, wherein the GPCR fusion protein is complexed with a ligand for the GPCR.

9. The method of claim 8, wherein said ligand an agonist of said GPCR.

10. The method of claim 1, wherein the GPCR fusion protein comprise a second heterologous autonomously folding stable domain between the TM5 and TM6 regions of said GPCR.

11. The method of claim 1, wherein the autonomously folding stable domain is fused to said GPCR within 5 amino acids of the TM1 region of the GPCR.

12. The method of claim 1, wherein the GPCR is a family A GPCR, a family B GPCR or a family C GCPR.

13. The method of claim 1, wherein the GPCR has an amino acid sequence that is at least 95% identical to a wild type GPCR.

14. The method of claim 1, wherein the GCPR is a biogenic amine receptor, a dopamine receptor, a seratonin receptor, an adrenergic receptor, a β2-adrenergic receptor, a melanocortin receptor, a ghrelin receptor, a metabotropic glutamate receptor or a chemokine receptor.

15. The method of claim 1, wherein the autonomously folding stable domain comprises an amino acid sequence that is at least 95% identical to a wild type protein.

16. The method of claim 1, wherein the GPCR has a truncated C-terminus.

17. The method of claim 1, wherein said method further comprises making said test compound.

* * * * *